US012774332B2

(12) United States Patent
Chen et al.

(10) Patent No.: US 12,774,332 B2
(45) Date of Patent: Oct. 27, 2026

(54) ANTI-CD8 ANTIBODIES AND USES THEREOF

(71) Applicant: Genentech, Inc., South San Francisco, CA (US)

(72) Inventors: Yvonne M. Chen, San Mateo, CA (US); Eugene Yu-Chuan Chiang, Menlo Park, CA (US); Jane Louise Grogan, San Francisco, CA (US); Simon-Peter Williams, Redwood City, CA (US); Matthew Lawrence Albert, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 651 days.

(21) Appl. No.: 18/346,128

(22) Filed: Jun. 30, 2023

(65) Prior Publication Data

US 2024/0018241 A1 Jan. 18, 2024

Related U.S. Application Data

(60) Division of application No. 16/788,003, filed on Feb. 11, 2020, now Pat. No. 11,739,150, which is a (Continued)

(51) Int. Cl.
*C07K 16/28* (2006.01)
*A61K 35/17* (2025.01)
(Continued)

(52) U.S. Cl.
CPC .......... *C07K 16/2815* (2013.01); *A61K 35/17* (2013.01); *A61K 39/0011* (2013.01);
(Continued)

(58) Field of Classification Search
None
See application file for complete search history.

(56) References Cited

U.S. PATENT DOCUMENTS 4,816,567 A 3/1989 Cabilly
5,208,020 A 5/1993 Chari
(Continued)

FOREIGN PATENT DOCUMENTS

EP 1317476 B1 1/2008
EP 1930728 A1 6/2008
(Continued)

OTHER PUBLICATIONS

Bates, D. et al. (2014, e-pub. May 12, 2014) "Development and Characterization of an Antibody-Labeled Super-Paramagnetic Iron Oxide Contrast Agent Targeting Prostate Cancer Cells for Magnetic Resonance Imaging," PloS One 9(5) e97220, pp. 1-11.
(Continued)

*Primary Examiner* — Joanne Hama
*Assistant Examiner* — Rudolph E. Sloup, Jr. IV
(74) *Attorney, Agent, or Firm* — Roberto K. Rodriguez

(57) ABSTRACT

Provided are anti-CD8 antibodies that bind human CD8 and do not stimulate or inhibit the activation of $CD8^+$ T cells. Also provided are nucleic acids encoding such anti-CD8 antibodies, vectors comprising such nucleic acids, host cells comprising same, and methods of making such anti-CD8 antibodies. Also provided are anti-CD8 antibodies conjugated to a detectable label. Provided are methods of using such anti-CD8 antibodies to detect $CD8^+$ T cells in a subject, monitor disease progress in a subject having cancer, and monitor treatment progress in a subject having cancer.

20 Claims, 36 Drawing Sheets

Specification includes a Sequence Listing.

Related U.S. Application Data continuation of application No. PCT/US2018/046332, filed on Aug. 10, 2018.

(60) Provisional application No. 62/597,337, filed on Dec. 11, 2017, provisional application No. 62/544,671, filed on Aug. 11, 2017.

(51) Int. Cl.
*A61K 38/00* (2006.01)
*A61K 39/00* (2006.01)
*A61K 45/06* (2006.01)
*A61K 47/65* (2017.01)

(52) U.S. Cl.
CPC .............. *A61K 47/65* (2017.08); *A61K 38/00* (2013.01); *A61K 45/06* (2013.01); *C07K 2317/24* (2013.01); *C07K 2317/52* (2013.01); *C07K 2317/565* (2013.01); *C07K 2317/92* (2013.01)

(56) References Cited

U.S. PATENT DOCUMENTS

| | | | |
|---|---|---|---|
| 5,500,362 | A | 3/1996 | Robinson |
| 5,571,894 | A | 11/1996 | Wels |
| 5,587,458 | A | 12/1996 | King |
| 5,624,821 | A | 4/1997 | Winter |
| 5,641,870 | A | 6/1997 | Rinderknecht |
| 5,648,237 | A | 7/1997 | Carter |
| 5,648,260 | A | 7/1997 | Winter |
| 5,731,168 | A | 3/1998 | Carter |
| 5,789,199 | A | 8/1998 | Pettit et al. |
| 5,821,337 | A | 10/1998 | Carter |
| 5,840,523 | A | 11/1998 | Simmons et al. |
| 5,869,046 | A | 2/1999 | Presta et al. |
| 5,959,177 | A | 9/1999 | Hein et al. |
| 6,040,498 | A | 3/2000 | Stomp et al. |
| 6,096,315 | A | 8/2000 | Zimmerman |
| 6,171,586 | B1 | 1/2001 | Lam |
| 6,267,958 | B1 | 7/2001 | Andya |
| 6,417,429 | B1 | 7/2002 | Hein et al. |
| 6,420,548 | B1 | 7/2002 | Vezina et al. |
| 6,461,825 | B1 | 10/2002 | Carriere |
| 6,737,056 | B1 | 5/2004 | Presta |
| 7,125,978 | B1 | 10/2006 | Vézina et al. |
| 7,332,581 | B2 | 2/2008 | Presta |
| 7,371,826 | B2 | 5/2008 | Presta |
| 7,387,772 | B1 | 6/2008 | Hansen |
| 7,695,936 | B2 | 4/2010 | Carter |
| 8,119,101 | B2 | 2/2012 | Byrd |
| 8,343,460 | B2 | 1/2013 | Mcbride |
| 8,841,271 | B2 | 9/2014 | Tabatadze |
| 8,846,002 | B2 | 9/2014 | Byrd |
| 2005/0014934 | A1 | 1/2005 | Hinton |
| 2005/0260186 | A1 | 11/2005 | Bookbinder et al. |
| 2006/0104968 | A1 | 5/2006 | Bookbinder et al. |
| 2008/0155704 | A1 | 6/2008 | Panayi |
| 2009/0182127 | A1 | 7/2009 | Kjaergaard |
| 2009/0215053 | A1 | 8/2009 | Galon |
| 2011/0311443 | A1 | 12/2011 | Schubert |
| 2014/0147382 | A1 | 5/2014 | Goldenberg |
| 2014/0271462 | A1 | 9/2014 | Ho |
| 2014/0329704 | A1 | 11/2014 | Melton |
| 2020/0172620 | A1 | 6/2020 | Chen et al. |

FOREIGN PATENT DOCUMENTS

| | | | |
|---|---|---|---|
| EP | 0939796 | B1 | 5/2009 |
| EP | 1546203 | B1 | 6/2012 |
| EP | 2216342 | B1 | 4/2015 |
| JP | 2011172585 | A | 9/2011 |
| JP | 2016520514 | A | 7/2016 |
| KR | 20130139342 | A | 12/2013 |
| WO | 199316185 | A2 | 8/1993 |
| WO | 199316185 | A3 | 9/1993 |
| WO | 199429351 | A2 | 12/1994 |
| WO | 199429351 | A3 | 2/1995 |
| WO | 2003076948 | A1 | 9/2003 |
| WO | 2004058298 | A1 | 7/2004 |
| WO | 2005063816 | A2 | 7/2005 |
| WO | 2005100402 | A1 | 10/2005 |
| WO | 2006029879 | A2 | 3/2006 |
| WO | 2006044908 | A2 | 4/2006 |
| WO | 2006044908 | A3 | 8/2006 |
| WO | 2006029879 | A3 | 9/2006 |
| WO | 2007045996 | A1 | 4/2007 |
| WO | 2009089004 | A1 | 7/2009 |
| WO | 2010009918 | A1 | 1/2010 |
| WO | 2012130831 | A1 | 10/2012 |
| WO | 2014025828 | A1 | 2/2014 |
| WO | 2014164553 | A1 | 10/2014 |
| WO | 2016196605 | A1 | 12/2016 |
| WO | 2018064165 | A2 | 4/2018 |
| WO | 2018115519 | A1 | 6/2018 |

OTHER PUBLICATIONS

Boerman, O.C. et al. (Aug. 2011) "Immuno-PET of Cancer: a Revival of Antibody Imaging," J. Nucl. Med. 52(8):1171-1172.

Brennan, M. et al. (Jul. 5, 1985). "Preparation of Bispecific Antibodies by Chemical Recombination of Monoclonal Immunoglobulin G1 Fragments," Science 229:81-83.

Brüggemann, M. et al. (Nov. 1, 1987). "Comparison of the Effector Functions of Human Immunoglobulins Using a Matched Set of Chimeric Antibodies," J. Exp. Med. 166:1351-1361.

Carter, P. (2001). "Bispecific Human IgG by Design," Immunol. Methods 248:7-15.

Carter, P. et al. (Feb. 1992). "High Level *Escherichia coli* Expression and Production of a Bivalent Humanized Antibody Fragment," Bio/Technology 10:163-167.

Chari, R.V.J. et al. (Jan. 1, 1992). "Immunoconjugates Containing Novel Maytansinoids: Promising Anticancer Drugs," Cancer Res. 52:127-131.

Charlton, K.A. (2004). "Expression and Isolation of Recombinant Antibody Fragments in *E. coli*," Methods Mol Biol 248:245-254.

Chothia, C. et al. (1987), "Canonical Structures for the Hypervariable Regions of Immunoglobulins," J. Mol. Biol, 196:901-917.

Chowdhury, P.S. (2008). "Engineering Hot Spots for Affinity Enhancement of Antibodies," Methods Mol. Biol. 207:179-196.

Cillers, C. et al. (May 1, 2017, e-pub. May 31, 2017). "Tracking Antibody Distribution with Near-Infrared Fluorescent Dyes: Impact of Dye Structure and Degree of Labeling on Plasma Clearance," Mol Pharmaceuticals 14(5):1623-1633.

Clackson, T. et al. (Aug. 15, 1991). "Making Antibody Fragments Using Phage Display Libraries," Nature 352:624-628.

Clement, M. et al.. (Jun. 15, 2011). "Anti-CD8 Antibodies Can Trigger CD8+ T Cell Effector Function in the Absence of TCR Engagement and Improve Peptide-MHCI Tetramer Staining," The Journal of Immunology 187(2):654-663.

Clynes, R. et al. (Jan. 1998). "Fc Receptors Are Required in Passive and Active Immunity to Melanoma," Proc. Natl. Acad. Sci. USA 95:652-656.

Cockburn, I.A. et al. (May 28, 2013, e-pub. May 14, 2013). "In Vivo Imaging of CD8+ T Cell-Mediated Elimination of Malaria Liver Stages," PNAS 110(22):9090-9095.

Cragg, M.S. et al. (Apr. 1, 2004, e-pub. Oct. 9, 2003). "Antibody Specificity Controls In Vivo Effector Mechanisms of Anti-CD20 Reagents," Blood 103(7):2738-2743, 7 pages.

Cragg, M.S. et al. (Feb. 1, 2003). "Complement-Mediated Lysis By Anti-CD20 Mab Correlates With Segregation Into Lipid Rafts," Blood 101(3):1045-1052.

Cunningham, B.C. et al. (Jun. 2, 1989). "High-Resolution Epitope Mapping of hGH-Receptor Interactions by Alanine-Scanning Mutagenesis," Science 244:1081-1085.

De Grand, A.M. et al. (Dec. 2003) "An Operational Near-Infrared Fluorescence Imaging System Prototype for Large Animal Surgery," Technol Cancer Res Treat. 2(6):553-562.

(56) References Cited

OTHER PUBLICATIONS

Duncan, A.R. et al. (Apr. 21, 1988). "The Binding Site for C1q on IgG," Nature 322:738-740.
Gazzano-Santoro, H. et al. (1997). "A Non-Radioactive Complement-Dependent Cytotoxicity Assay Anti-CD20 Monoclonal Antibody," J. Immunol. Methods 202:163-171.
Gerngross, T.U. (Nov. 2004). "Advances in the Production of Human Therapeutic Proteins in Yeasts and Filamentous Fungi," Nature Biotechnology 22(11):1409-1414.
Goodman, J.W. et al. (1994). "Immunoglobulin Proteins," Chapter 6 in Basic And Clinical Immunology, Eighth Edition, Appleton & Lange: Norwalk, Conneticut, pp. 66-79.
Gopalakrishnan, V. et al. (Feb. 24, 2017). "Association of Diversity and Composition of the Gut Microbiome With Differential Responses to 95-104 PD-1 Based Therapy in Patients With Metastatic Melanoma," ASCO 2 pages.
Gopalakrishnan, V. et al. (Jan. 5, 2018). "Gut Microbiome Modulates Response to Anti-PD-1 Immunotherapy in Melanoma Patients," Science 359:97-103, 20 pages.
Graham, F.L. et al. (1977). "Characteristics of a Human Cell Line Transformed by DNA from Human Adenovirus Type 5," J. Gen Virol. 36:59-72.
Grootendorst, M.R. et al. (2016, e-pub. May 24, 2016). "Cerenkov Luminescence Imaging (CLI) for Image-Guided Cancer Surgery," Clin. Transl. Imaging. 4(5):353-366.
Guus, A.M.S. et al. (2007) "Immuno-PET: A Navigator in Monoclonal Antibody Development and Applications," The Oncologist 12:1379-1389.
Guyer, R.L. et al. (Aug. 1976). "Immunoglobulin Binding By Mouse Intestinal Epithelial Cell Receptors," J. Immunol. 117(2):587-593.
Hellstrom, I. et al. (Mar. 1985). "Strong Antitumor Activities of IgG3 Antibodies to a Human Melanoma-associated Ganglioside," Proc. Natl. Acad. Sci. USA 82:1499-1502.
Hellstrom, I. et al. (Sep. 1986). "Antitumor Effects of L6, an IgG2a Antibody That Reacts With Most Human Carcinomas," Proc. Natl. Acad. Sci. USA 83:7059-7063.
Hickson, J. (2009). "In Vivo Optical Imaging: Preclinical Applications and Considerations," Urol. Oncol Semin Orig Invest. 27:295-297.
Hilderbrand et al. (2010, E-pub. Oct. 30, 2009)."Near-Infrared Fluorescence: Application to In Vivo Molecular Imaging," Curr. Opin. Chem. Biol. 14(1):71-79.
Hong, G. et al. (Jan. 10, 2017). "Near-Infrared Fluorophores for Biomedical Imaging," Nat. Biomed. Eng. 1(0010):1-22.
Hoogenboom, H.R. et al. (2001). "Overview of Antibody Phage-Display Technology and Its Applications," Methods Mol Biol 178:1-37.
Hudson, P.J. et al. (Jan. 2003). "Engineered Antibodies," Nature Medicine 9(1):129-134.
International Preliminary Report on Patentability for PCT Application No. PCT/US2018/046332, issued on Feb. 11, 2020, filed on Aug. 18, 2018, 14 pages.
International Search Report and Written Opinion for PCT Application No. PCT/US2018/046332, mailed on Mar. 22, 2019, filed on Aug. 18, 2018, 26 pages.
Jones, P.T. et al. (May 29, 1986). "Replacing the Complementarity-Determining Regions in a Human Antibody With Those From a Mouse," Nature 321:522-525.
Kabat, E.A. et al. (1991). Sequences of Proteins of Immunological Interest, 5th ed., Public Health Service, National Institutes of Health, Bethesda, MD. TOC, 21 pages.
Kam, N.W.S. et al. (Aug. 16, 2005). "Carbon Nanotubes as Multifunctional Biological Transporters and Near-Infrared Agents for Selective Cancer Cell Destruction," PNAS 102(33):11600-11605, 6 pages.
Kim, J-K. et al. (1994). "Localization of the Site of the Murine IgGI Molecule That is Involved in Binding to the Murine Intestinal Fc Receptor," Eur. J. Immunol. 24:2429-2434.
Kindt, T.J. et al. (2007). "Antigens and Antibodies," in Chapter 4 of Kuby Immunology, 6th ed., W.H. Freeman and Co., N.Y, pp. 91, 14 pages.
Kontermann, R.E. (Jan. 2005). "Recombinant Bispecific Antibodies for Cancer Therapy," Acta Pharacol. Sinc. 26(1):1-9.
Laverman, P. et al. (May 2015). "Immuno-PET and Immuno-SPECT of Rheumatoid Arthritis with Radiolabeled Anti-Fibroblast Activation Protein Antibody Correlates with Severity of Arthritis," J. Nucl. Med. 56(5):778-783.
Li, H. et al. (Feb. 2006, e-published on Jan. 22, 2006). "Optimization of Humanized IgGs in Glycoengineered Pichia Pastoris," Nature Biotechnology 24(2):210-215.
Liu, T-M. et al. (Aug. 5, 2016). "Revisiting the Classification Of Nir-Absorbing/Emitting Nanomaterials for in Vivo Bioapplications," NPG Asia Materials 8(e295):1-25.
Lo, M. et al. (Mar. 3, 2017). "Effector-Attenuating Substitutions That Maintain Antibody Stability and Reduce Toxicity in Mice," Journal of Biological Chemistry 292(9):3900-3908.
Luker, G.D. et al. (2008, e-pub. Dec. 12, 2007). "Optical Imaging: Current Applications and Future Directions," J. Nucl. Med. 49:1-4.
Lütje, S. et al. (Nov. 1, 2014, e-pub. Sep. 24, 2014). "Pretargeted Dual-Modality Immuno-SPECT and Near-Infrared Fluorescence Imaging for Image-Guided Surgery of Prostate Cancer," Cancer Res. 74(21):6216-6223.
Maccallum, R.M. et al. (Oct. 1996). "Antibody-Antigen Interactions: Contact Analysis and Binding Site Topography," J. Mol. Biol. 262(5):732-745.
Marvin, J.S. et al. (Jun. 2005). "Recombinant Approaches to IgG-Like Bispecific Antibodies," Acta Pharmacol. Sin. 26(6):649-658.
Mather, J.P. (1980). "Establishment and Characterization of Two Distinct Mouse Testicular Epithelial Cell Lines," Biology of Reproduction 23:243-252.
Mather, J.P. et al. (1982). "Culture of Testicular Cells in Hormone-Supplemented Serum-Free Medium," Annals New York Academy of Sciences pp. 44-68.
Matson, V. et al. (Jan. 5, 2018). "The Commensal Microbiome Is Associated With Anti-PD-1 Efficacy in Metastatic Melanoma Patients," Science 359(6371):104-108.
Merchant, M. et al. (Jul. 23, 2013) "Monovalent Antibody Design and Mechanism of Action of Onartuzumab, a MET Antagonist with Anti-Tumor Activity as a Therapeutic Agent," PNAS, E2987-E2996.
Morimoto, K. et al. (1992). "Single-Step Purification of F(AB')2 Fragments of Mouse Monoclonal Antibodies (Immunoglobulins G1) By Hydrophobic Interaction High Performance Liquid Chromatography Using TSKgel Phenyl-5PW," J. Biochem. Biophys. Method 24:107-117.
Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.
Murakami, M.S. et al. (1995). "Cell Cycle Regulation, Oncogenes, and Antineoplastic Drugs," Chapter 1 in The Molecular Basis of Cancer, W.B. Saunders Company, Philadelphia, pp. 3-17.
Muselaers, C.H.J. et al. (2013, e-pub. Feb. 21, 2013). "Indium-111-Labeled Girentuximab ImmunoSPECT as a Diagnostic Tool in Clear Cell Renal Cell Carcinoma," Eur. Urology 64(4):1101-1106.
Nakayama, A. et al. (Oct. 2002). "Functional Near-Infrared Fluorescence Imaging for Cardiac Surgery and Targeted Gene Therapy," Molecular Imaging 1(4):365-377.
Ntziachristos, V. et al. (2003, e-pub. Jul. 19, 2002). "Fluorescence Imaging With Near-Infrared Light: New Technological Advances That Enable in Vivo Molecular Imaging," Eur. Radiol. 13:195-208.
Ott, P.A. et al. (Jul. 13, 2017). "An Immunogenic Personal Neoantigen Vaccine for Melanoma Patients," Nature 547:217-221, 34 pages total.
Pansare, V. et al. (Mar. 13, 2012). "Review of Long-Wavelength Optical and NIR Imaging Materials: Contrast Agents, Fluorophores and Multifunctional Nano Carriers," Chem. Mater. 24(5):812-827, 44 pages total.
Paul, W.E. (1993). "Structure and Function of Immunoglobulins," Chapter 9 in Fundamental Immunology, 3rd Edition, pp. 292-295.
Petkova, S.B. et al. (2006, e-pub. Oct. 31, 2006). "Enhanced Half-Life of Genetically Engineered Human IgG1 Antibodies in a

(56) References Cited

OTHER PUBLICATIONS

Humanized FcRn Mouse Model: Potential Application in Humorally Mediated Autoimmune Disease," Int'l. Immunol. 18(12):1759-1769.
Petrelli, A. et al. (Jul. 2016, e-pub. Jun. 3, 2016). "CD8+ T Cells in Human Autoimmune Arthritis: The Usual Suspects," Nature Reviews Rheumatology 12:421-428.
Plückthun, A. (1994). "Antibodies from *Escherichia coli*," in Chapter 11 The Pharmacology of Monoclonal Antibodies, vol. 113, Rosenburg and Moore eds., Springer-Verlag, New York, pp. 269-315, 48 pages.
Pool, M. et al. (2017, e-pub. Mar. 19, 2017). "89Zr-Onartuzumab PET Imaging of c-MET Receptor Dynamics," Eur. J. Nucl. Med. Mol Imaging 44:1328-1336.
Portolano, S. et al. (Feb. 1, 1993). "Lack of Promiscuity in Autoantigen-Specific H and L Chain Combinations as Revealed by Human H and L Chain 'Roulette'," The Journal of Immunology 150(3):880-887.
Presta, L.G. (1992). "Antibody Engineering," Current Opinion in Structural Biology, 2:593-596.
Quek, C-H. et al. (2012) "Near-Infrared Fluorescent Nanoprobes for in VivoOptical Imaging," Nanomaterials. 2: 92-112.
Ravetch, J.V. et al. (1991). "Fc Receptors," Annu. Rev. Immunol. 9:457-492.
Reddy, S. et al. (May 2010) "Immuno-Positron Emission Tomography In Cancer Models," Semin. Nucl. Med. 40(3):182-189, 16 pages total.
Remington's Pharmaceutical Sciences. (1980). 16th edition, Osol, A. Ed, pp. 1-2, (Table of Contents Only).
Ridgway, J.B.B. et al. (1996). "'Knobs-Into-Holes' Engineering of Antibody CH3 Domains for Heavy Chain Heterodimerization," Protein Engineering 9(7):617-621.
Riechmann, L. et al. (Mar. 24, 1988). "Reshaping Human Antibodies for Therapy," Nature 332:323-327.
Routy, B. et al. (Jan. 5, 2018). "Gut Microbiome Influences Efficacy of PD-1-Based Immunotherapy Against Epithelial Tumors," Science 359(6371):91-97.
Rudd, S.E. et al. (Oct. 14, 2016). "A Desferrioxamine B Squaramide Ester for the Incorporation of Zirconium-89 Into Antibodies," Chem. Commun. 52(80):11889-11892.
Sahin, U. et al. (Jul. 13, 2017) "Personalized RNA Mutanome Vaccines Mobilize Poly-Specific Therapeutic Immunity Against Cancer," Nature 547:222-226, 19 pages.
Santangelo, P.H. et al. (May 2015, e-pub. Mar. 9, 2015). "Whole-Body ImmunoPET Reveals Active Si V Dynamics in Viremic and Antiretroviral Therapy-Treated Macaques," Nature Methods 12(5):427-432.
Sohn, C-H. et al. (Jan. 2015). "MRI Molecular Imaging Using GLUT1 Antibody-Fe304 Nanoparticles in the Hemangioma Animal Model for Differentiating Infantile Hemangioma From Vascular Malformation," Nanomedicine 11(1):127-135.
Srivastava, A.K. (2015). "Advances in Using MRI Probes and Sensors for in Vivo Cell Tracking as Applied to Regenerative Medicine," Dis. Models Mech. 8(4):323-336.
Stites, D.P. et al. (1994). "Immunoglobulin Protiens," Chapter 6 in Basic Clinical Immunology, 8th Edition, Appleton & Lange, Norwalk, CT, pp. 66-79.
Tanaka, E. et al. (2006). Image-Guided Oncologic Surgery Using Invisible Light: Completed Pre-Clinical Development for Sentinel Lymph Node Mapping, Ann. Surg. Oncol. 13(12):1671-1681, 17 pages total.
Themelis, G. et al. (Nov./Dec. 2009). "Real-Time Intraoperative Fluorescence Imaging System Using Light-Absorption Correction," J. Biomed. Opt. 14(6):4:064012-1-064012-9.
Troyan, S.L. et al. (Oct. 2009) "The FLARE™ Intraoperative Near-Infrared Fluorescence Imaging System: A First-in-Human Clinical Trial in Breast Cancer Sentinel Lymph Node Mapping," Ann. Surg. Oncol. 16(10):2943-2952, 17 pages total.
Urlaub, G. et al. (Jul. 1980). "Isolation of Chinese Hamster Cell Mutants Deficient in Dihydrofolate Reductase Activity," Proc. Natl. Acad. Sci. USA 77(7):4216-4220.
Van Dongen, G.A. et al. (Dec. 2007). "Immuno-PET: a Navigator in Monoclonal Antibody Development and Applications," The Oncologist 12(12):1379-1389.
Verel, I. et al. (Jan. 2005) "The Promise of Immuno-PET in Radioimmunotherapy," J Nucl Med, 46(suppl. 1):164S-171S.
Verel, I.et al. (2003). "89Zr Immuno-ET: Comprehensive Procedures for the Production of 89Zr-Labeled Monoclonal Antibodies," J. Nuclear Medicine 44:1271-1281.
Vugts, D.J. et al. (2017, e-pub. Aug. 30, 2016). "Comparison of the Octadentate Bifunctional Chelator DFO*-pPhe-NCS and the Clinically Used Hexadentate Bifunctional Chelator DFO-pPhe-NCS for 89Zr-immuno-PET," Eur. J. Nucl. Med. Mol. Imaging. 44:286-295.
Yazaki, P.J. et al. (2003). "Expression of Recombinant Antibodies in Mammalian Cell Lines," Methods in Molecular Biology 248:255-268.
Zapata, G. et al. (1995). "Engineering Linear F(ab')2 Fragments for Efficient Production in *Escherichia coli* and Enhanced Antiproliferative Activity," Protein Eng. 8(10):1057-1062.
Zhang, X. et al. (2012, e-pub. Apr. 2012). "Near-Infrared Molecular Probes for In Vivo Imaging," Chapter 12: Unit 12.27, Current Protocols in Cytometry, Unit 12.27, 20 pages.
Zhang, Y. et al. (2014). "In Vivo Tomographic Imaging With Fluorescence and MRI Using Tumor-Targeted Dual-Labeled Nanoparticles," Int. J. Medicine 9:33-41.
Zhou, Z. et al. (Jan. 2013). "Gaolinium-Based Constrast Agents for MR Cancer Imaging," Wiley Interdiscip. Rev. Nanomed. Nanobiotechnol. 5(1):1-18, 31 pages.
Zhu, Y. et al. (Apr. 28, 2015). "In Vivo Molecular MRI Imaging of Prostate Cancer by Targeting PSMA with Polypeptide-Labeled Superparamagnetic Iron Oxide Nanoparticles," Int. J. Mol. Sci. 16: 9573-9587.

FIG. 2A

```
rhesus_CD8a   MRNQAPGRPKGATSPPPLPTGSRAPPVAPELRAEPRPGERVMAPPVTALL 50   SEQ ID NO: 31
cyno_CD8a     MRNQAPGRPKGATSPPPLPTGSRAPPVAPELRAEPRPGERVMAPPVTALL 50   SEQ ID NO: 32
human_CD8a                                             MALPVTALL 9    SEQ ID NO: 33

rhesus_CD8a   LPLVLLLHAARPNQFRVSPLGRTWNLGETVELKCQVLLSNPTSGCSWLFQ 100  SEQ ID NO: 31
cyno_CD8a     LPLVLLLHAARPNQFRVSPLGRTWNLGETVELKCQVLLSNPTSGCSWLFQ 100  SEQ ID NO: 32
human_CD8a    LPLALLLHAARPSQFRVSPLDRTWNLGETVELKCQVLLSNPTSGCSWLFQ 59   SEQ ID NO: 33

rhesus_CD8a   PRGTAARPTFLLYLSQNKPKAAEGLDTQRFSGKRLGDTFVLTLRDFRQEN 150  SEQ ID NO: 31
cyno_CD8a     PRGTAARPTFLLYLSQNKPKAAEGLDTQRFSGKRLGDTFVLTLRDFRQEN 150  SEQ ID NO: 32
human_CD8a    PRGAAASPTFLLYLSQNKPKAAEGLDTQRFSGKRLGDTFVLTLSDFRREN 109  SEQ ID NO: 33

rhesus_CD8a   EGYYFCSALSNSIMYFSHFVPVFLPAKPTTTPAPRSPTPAPTTASQPLSL 200  SEQ ID NO: 31
cyno_CD8a     EGYYFCSALSNSIMYFSHFVPVFLPAKPTTTPAPRPPTPAPTTASQPLSL 200  SEQ ID NO: 32
human_CD8a    EGYYFCSALSNSIMYFSHFVPVFLPAKPTTTPAPRPPTPAPTIASQPLSL 159  SEQ ID NO: 33

rhesus_CD8a   RPEACRPAAGGSVNTRGLDFACDIYIWAPLAGACGVLLLSLVITLYCNHR 250  SEQ ID NO: 31
cyno_CD8a     RPEACRPAAGGSVNTRGLDFACDIYIWAPLAGACGVLLLSLVITLYCNHR 250  SEQ ID NO: 32
human_CD8a    RPEACRPAAGGAVHTRGLDFACDIYIWAPLAGTCGVLLLSLVITLYCNHR 170  SEQ ID NO: 33

rhesus_CD8a   NRRRVCKCPRPVVKSGGKPSLSDRYV 276  SEQ ID NO: 31
cyno_CD8a     NRRRVCKCPRPVVKSGGKPSLSDRYV 276  SEQ ID NO: 32
human_CD8a    NRRRVCKCPRPVVKSGDKPSLSARY  182  SEQ ID NO: 33
```

FIG. 3C
OKT8.v11-OA-LALAPG
gD-OA
vehicle
no stim
CD8+CFSElo
(normalized to vehicle control)
125
100
75
50
25
0
0.001
0.01
0.1
1
10
100
1000
Ab concentration (μg/ml)

ANTI-CD8 ANTIBODIES AND USES THEREOF

CROSS-REFERENCE TO RELATED APPLICATIONS

This application is a divisional of U.S. patent application Ser. No. 16/788,003, filed Feb. 11, 2020, which is a continuation of International Patent Application No. PCT/US2018/046332, filed Aug. 10, 2018 which claims priority to and the benefit of U.S. Provisional Application Nos. 62/544,671, filed Aug. 11, 2017, and 62/597,337 filed Dec. 11, 2017, the contents of each of which are hereby incorporated by reference in their entirety.

SUBMISSION OF SEQUENCE LISTING ON ASCII TEXT FILE

The contents of the electronic sequence listing (146392034110seqlist.xml; Size: 45,043 bytes; and Date of Creation: Jun. 12, 2023) are herein incorporated by reference in their entirety.

FIELD OF THE INVENTION

The present invention relates to anti-CD8 antibodies and methods of using such antibodies for imaging $CD8^+$ T-cells in vivo.

BACKGROUND OF THE INVENTION

Characterization of the number, types, and spatial distribution of immune cells in tumor tissues can provide crucial information regarding cancer diagnosis, prognosis, therapy selection, and response to therapy. Specifically, $CD8^+$ cytotoxic lymphocytes have been consistently reported as having diagnostic and prognostic significance in various cancers. Current methods of detecting $CD8^+$ cells entail the isolation of cells from the peripheral blood or a tissue of interest. Such sampling methods are prone to error and do not provide dynamic information that reflects the number, localization, and movement of $CD8^+$ cells in vivo. One exemplary non-invasive method for detecting immune cells in vivo is positron emission tomography (PET) using radiolabeled tracers. However, the use of such tracers is limited by radioisotope half-life and cell division, which leads to probe dilution in vivo. Accordingly, there remains a need in the art for methods and reagents for monitoring changes in the quantity and temporal distribution of $CD8^+$ cells in vivo.

BRIEF SUMMARY OF THE INVENTION

In some embodiments, provided herein is an anti-CD8 antibody that binds human CD8 and does not stimulate or inhibit the activation of $CD8^+$ T cells. In certain embodiments according to (or as applied to) any of the embodiments above, the anti-CD8 antibody does not induce $CD8^+$ T cell proliferation. In certain embodiments according to (or as applied to) any of the embodiments above, the anti-CD8 antibody does not induce IFN-γ production by $CD8^+$ T cells. In certain embodiments according to (or as applied to) any of the embodiments above, the anti-CD8 antibody does not bind $CD^{4+}$ T cells. In certain embodiments according to (or as applied to) any of the embodiments above, the anti-CD8 antibody does not bind $CD3^-$ cells. In certain embodiments according to (or as applied to) any of the embodiments above, the anti-CD8 antibody does not deplete $CD8^+$ T cells from circulation.

In certain embodiments according to (or as applied to) any of the embodiments above, the anti-CD8 antibody is a chimeric antibody, a humanized antibody, or a human antibody. In certain embodiments according to (or as applied to) any of the embodiments above, the anti-CD8 antibody is a monovalent antibody. In certain embodiments according to (or as applied to) any of the embodiments above, the monovalent antibody comprises an antibody heavy chain comprising a first Fc domain, an antibody light chain, and a second Fc domain, wherein the antibody heavy chain pairs with the antibody light chain, and wherein the first Fc domain and the second Fc domain form a dimer. In certain embodiments according to (or as applied to) any of the embodiments above, the first Fc domain comprises a cavity, and wherein the second Fc domain comprises a protuberance which is positionable in the cavity in the first Fc domain. In certain embodiments according to (or as applied to) any of the embodiments above, first Fc domain comprises T366S, L358A, and Y407V mutations, wherein the second Fc domain comprises a T366W mutation, and wherein the amino acid residues are numbered according to the EU numbering system. In certain embodiments according to (or as applied to) any of the embodiments above, the second Fc domain comprises a cavity, and wherein the first Fc domain comprises a protuberance which is positionable in the cavity in the second Fc domain. In certain embodiments according to (or as applied to) any of the embodiments above, the first Fc domain comprises a T366W mutation, wherein the second domain comprises T366S, L358A, and Y407V mutations, and wherein the amino acid residues are numbered according to the EU numbering system. In certain embodiments according to (or as applied to) any of the embodiments above, the anti-CD8 antibody is a human IgG antibody. In certain embodiments according to (or as applied to) any of the embodiments above, the human IgG antibody is an IgG1 antibody. In certain embodiments according to (or as applied to) any of the embodiments above, the first and second Fc domains comprise L234A and L235A mutations. In certain embodiments according to (or as applied to) any of the embodiments above, the first and second Fc domains each comprise s a P329G mutation.

In certain embodiments according to (or as applied to) any of the embodiments above, the anti-CD8 antibody binds to human CD8 with a $K_D$ of less than about 10 nM. In certain embodiments according to (or as applied to) any of the embodiments above, the anti-CD8 antibody binds to cynomolgus CD8 with a $K_D$ of less than about 200 nM. In certain embodiments according to (or as applied to) any of the embodiments above, the anti-CD8 antibody binds to rhesus CD8 with a $K_D$ of less than about 200 nM. In certain embodiments according to (or as applied to) any of the embodiments above, the anti-CD8 antibody does not bind mouse CD8 or rat CD8.

In certain embodiments according to (or as applied to) any of the embodiments above, the anti-CD8 antibody comprises a heavy chain variable domain that comprises (1) a CDR-H1 comprising an amino acid sequence set forth in SEQ ID NO: 9; (2) a CDR-H2 comprising an amino acid sequence set forth in SEQ ID NO: 10 or SEQ ID NO: 11; and (3) a CDR-H3 comprising an amino acid sequence set forth in set forth in SEQ ID NO: 12 or SEQ ID NO: 13; and/or a light chain variable domain that comprises (1) a CDR-L1 comprising an amino acid sequence set forth in set forth in SEQ ID NO: 1 or SEQ ID NO: 2; (2) a CDR-L2 comprising an amino acid sequence set forth in SEQ ID NO: 3; and (3) a CDR-L3 comprising an amino acid sequence set forth in any one of SEQ ID NOs: 4-8.

In certain embodiments according to (or as applied to) any of the embodiments above, the anti-CD8 antibody comprises a heavy chain variable domain that comprises (1) a CDR-H1 comprising an amino acid sequence set forth in SEQ ID NO: 9; (2) a CDR-H2 comprising an amino acid sequence set forth in SEQ ID NO: 10 or SEQ ID NO: 11; and (3) a CDR-H3 comprising an amino acid sequence set forth in set forth in SEQ ID NO: 12 or SEQ ID NO: 13; and a light chain variable domain that comprises (1) a CDR-L1 comprising an amino acid sequence set forth in set forth in SEQ ID NO: 1 or SEQ ID NO: 2; (2) a CDR-L2 comprising an amino acid sequence set forth in SEQ ID NO: 3; and (3) a CDR-L3 comprising an amino acid sequence set forth in any one of SEQ ID NOs: 4-8. In certain embodiments according to (or as applied to) any of the embodiments above, the anti-CD8 antibody comprises a heavy chain variable domain comprising (1) a CDR-H1 comprising the amino acid sequence set forth in SEQ ID NO: 9; (2) a CDR-H2 comprising the amino acid sequence set forth in SEQ ID NO: 10; and (3) a CDR-H3 comprising the amino acid sequence set forth in SEQ ID NO: 12; and/or a light chain variable domain comprising (1) a CDR-L1 comprising the amino acid sequence set forth in SEQ ID NO: 1; (2) a CDR-L2 comprising the amino acid sequence set forth in SEQ ID NO: 3; and (3) a CDR-L3 comprising the amino acid sequence set forth in SEQ ID NO: 4. In certain embodiments according to (or as applied to) any of the embodiments above, the anti-CD8 antibody comprises a heavy chain variable domain comprising (1) a CDR-H1 comprising the amino acid sequence set forth in SEQ ID NO: 9; (2) a CDR-H2 comprising the amino acid sequence set forth in SEQ ID NO: 10; and (3) a CDR-H3 comprising the amino acid sequence set forth in SEQ ID NO: 12; and/or a light chain variable domain comprising (1) a CDR-L1 comprising the amino acid sequence set forth in SEQ ID NO: 1; (2) a CDR-L2 comprising the amino acid sequence set forth in SEQ ID NO: 3; and (3) a CDR-L3 comprising the amino acid sequence set forth in SEQ ID NO: 5. In certain embodiments according to (or as applied to) any of the embodiments above, the anti-CD8 antibody comprises a heavy chain variable domain comprising (1) a CDR-H1 comprising the amino acid sequence set forth in SEQ ID NO: 9; (2) a CDR-H2 comprising the amino acid sequence set forth in SEQ ID NO: 10; and (3) a CDR-H3 comprising the amino acid sequence set forth in SEQ ID NO: 12; and/or a light chain variable domain comprising (1) a CDR-L1 comprising the amino acid sequence set forth in SEQ ID NO: 1; (2) a CDR-L2 comprising the amino acid sequence set forth in SEQ ID NO: 3; and (3) a CDR-L3 comprising the amino acid sequence set forth in SEQ ID NO: 6. In certain embodiments according to (or as applied to) any of the embodiments above, the anti-CD8 antibody comprises a heavy chain variable domain comprising (1) a CDR-H1 comprising the amino acid sequence set forth in SEQ ID NO: 9; (2) a CDR-H2 comprising the amino acid sequence set forth in SEQ ID NO: 10; and (3) a CDR-H3 comprising the amino acid sequence set forth in SEQ ID NO: 12; and/or a light chain variable domain comprising (1) a CDR-L1 comprising the amino acid sequence set forth in SEQ ID NO: 1; (2) a CDR-L2 comprising the amino acid sequence set forth in SEQ ID NO: 3; and (3) a CDR-L3 comprising the amino acid sequence set forth in SEQ ID NO: 7. In certain embodiments according to (or as applied to) any of the embodiments above, the anti-CD8 antibody comprises a heavy chain variable domain comprising (1) a CDR-H1 comprising the amino acid sequence set forth in SEQ ID NO: 9; (2) a CDR-H2 comprising the amino acid sequence set forth in SEQ ID NO: 10; and (3) a CDR-H3 comprising the amino acid sequence set forth in SEQ ID NO: 12; and/or a light chain variable domain comprising (1) a CDR-L1 comprising the amino acid sequence set forth in SEQ ID NO: 1; (2) a CDR-L2 comprising the amino acid sequence set forth in SEQ ID NO: 3; and (3) a CDR-L3 comprising the amino acid sequence set forth in SEQ ID NO: 8. In certain embodiments according to (or as applied to) any of the embodiments above, the anti-CD8 antibody comprises a heavy chain variable domain comprising (1) a CDR-H1 comprising the amino acid sequence set forth in SEQ ID NO: 9; (2) a CDR-H2 comprising the amino acid sequence set forth in SEQ ID NO: 11; and (3) a CDR-H3 comprising the amino acid sequence set forth in SEQ ID NO: 13; and/or a light chain variable domain comprising (1) a CDR-L1 comprising the amino acid sequence set forth in SEQ ID NO: 1; (2) a CDR-L2 comprising the amino acid sequence set forth in SEQ ID NO: 3; and (3) a CDR-L3 comprising the amino acid sequence set forth in SEQ ID NO: 8. In certain embodiments according to (or as applied to) any of the embodiments above, the anti-CD8 antibody comprises a heavy chain variable domain comprising (1) a CDR-H1 comprising the amino acid sequence set forth in SEQ ID NO: 9; (2) a CDR-H2 comprising the amino acid sequence set forth in SEQ ID NO: 10; and (3) a CDR-H3 comprising the amino acid sequence set forth in SEQ ID NO: 12; and/or a light chain variable domain comprising (1) a CDR-L1 comprising the amino acid sequence set forth in SEQ ID NO: 2; (2) a CDR-L2 comprising the amino acid sequence set forth in SEQ ID NO: 3; and (3) a CDR-L3 comprising the amino acid sequence set forth in SEQ ID NO: 8.

In certain embodiments according to (or as applied to) any of the embodiments above, the anti-CD8 antibody comprises a heavy chain variable domain comprising (1) a CDR-H1 comprising the amino acid sequence set forth in SEQ ID NO: 9; (2) a CDR-H2 comprising the amino acid sequence set forth in SEQ ID NO: 10; and (3) a CDR-H3 comprising the amino acid sequence set forth in SEQ ID NO: 12; and a light chain variable domain comprising (1) a CDR-L1 comprising the amino acid sequence set forth in SEQ ID NO: 1; (2) a CDR-L2 comprising the amino acid sequence set forth in SEQ ID NO: 3; and (3) a CDR-L3 comprising the amino acid sequence set forth in SEQ ID NO: 4. In certain embodiments according to (or as applied to) any of the embodiments above, the anti-CD8 antibody comprises a heavy chain variable domain comprising (1) a CDR-H1 comprising the amino acid sequence set forth in SEQ ID NO: 9; (2) a CDR-H2 comprising the amino acid sequence set forth in SEQ ID NO: 10; and (3) a CDR-H3 comprising the amino acid sequence set forth in SEQ ID NO: 12; and a light chain variable domain comprising (1) a CDR-L1 comprising the amino acid sequence set forth in SEQ ID NO: 1; (2) a CDR-L2 comprising the amino acid sequence set forth in SEQ ID NO: 3; and (3) a CDR-L3 comprising the amino acid sequence set forth in SEQ ID NO: 5. In certain embodiments according to (or as applied to) any of the embodiments above, the anti-CD8 antibody comprises a heavy chain variable domain comprising (1) a CDR-H1 comprising the amino acid sequence set forth in SEQ ID NO: 9; (2) a CDR-H2 comprising the amino acid sequence set forth in SEQ ID NO: 10; and (3) a CDR-H3 comprising the amino acid sequence set forth in SEQ ID NO: 12; and a light chain variable domain comprising (1) a CDR-L1 comprising the amino acid sequence set forth in SEQ ID NO: 1; (2) a CDR-L2 comprising the amino acid sequence set forth in SEQ ID NO: 3; and (3) a CDR-L3 comprising the amino acid sequence set forth in SEQ ID NO: 6. In certain embodiments according to (or as applied to) any of the embodiments above, the anti-CD8 antibody comprises a heavy chain variable domain comprising (1) a CDR-H1 comprising the amino acid sequence set forth in SEQ ID NO: 9; (2) a CDR-H2 comprising the amino acid sequence set forth in SEQ ID NO: 10; and (3) a CDR-H3 comprising the amino acid sequence set forth in SEQ ID NO: 12; and a light chain variable domain comprising (1) a CDR-L1 comprising the amino acid sequence set forth in SEQ ID NO: 1; (2) a CDR-L2 comprising the amino acid sequence set forth in SEQ ID NO: 3; and (3) a CDR-L3 comprising the amino acid sequence set forth in SEQ ID NO: 7. In certain embodiments according to (or as applied to) any of the embodiments above, the anti-CD8 antibody comprises a heavy chain variable domain comprising (1) a CDR-H1 comprising the amino acid sequence set forth in SEQ ID NO: 9; (2) a CDR-H2 comprising the amino acid sequence set forth in SEQ ID NO: 10; and (3) a CDR-H3 comprising the amino acid sequence set forth in SEQ ID NO: 12; and a light chain variable domain comprising (1) a CDR-L1 comprising the amino acid sequence set forth in SEQ ID NO: 1; (2) a CDR-L2 comprising the amino acid sequence set forth in SEQ ID NO: 3; and (3) a CDR-L3 comprising the amino acid sequence set forth in SEQ ID NO: 8. In certain embodiments according to (or as applied to) any of the embodiments above, the anti-CD8 antibody comprises a heavy chain variable domain comprising (1) a CDR-H1 comprising the amino acid sequence set forth in SEQ ID NO: 9; (2) a CDR-H2 comprising the amino acid sequence set forth in SEQ ID NO: 11; and (3) a CDR-H3 comprising the amino acid sequence set forth in SEQ ID NO: 13; and a light chain variable domain comprising (1) a CDR-L1 comprising the amino acid sequence set forth in SEQ ID NO: 1; (2) a CDR-L2 comprising the amino acid sequence set forth in SEQ ID NO: 3; and (3) a CDR-L3 comprising the amino acid sequence set forth in SEQ ID NO: 8. In certain embodiments according to (or as applied to) any of the embodiments above, the anti-CD8 antibody comprises a heavy chain variable domain comprising (1) a CDR-H1 comprising the amino acid sequence set forth in SEQ ID NO: 9; (2) a CDR-H2 comprising the amino acid sequence set forth in SEQ ID NO: 10; and (3) a CDR-H3 comprising the amino acid sequence set forth in SEQ ID NO: 12; and a light chain variable domain comprising (1) a CDR-L1 comprising the amino acid sequence set forth in SEQ ID NO: 2; (2) a CDR-L2 comprising the amino acid sequence set forth in SEQ ID NO: 3; and (3) a CDR-L3 comprising the amino acid sequence set forth in SEQ ID NO: 8.

In certain embodiments according to (or as applied to) any of the embodiments above, the anti-CD8 antibody comprises a heavy chain variable domain set forth in any one of SEQ ID NO: 14, 16, 18, 20, 22, 24, and 26; and/or a light chain variable domain set forth in any one of SEQ ID NO: 15, 17, 19, 21, 23, 25, and 27. In certain embodiments according to (or as applied to) any of the embodiments above, the anti-CD8 antibody comprises a heavy chain variable domain set forth in any one of SEQ ID NO: 14, 16, 18, 20, 22, 24, and 26; and a light chain variable domain set forth in any one of SEQ ID NO: 15, 17, 19, 21, 23, 25, and 27. In certain embodiments according to (or as applied to) any of the embodiments above, the anti-CD8 antibody comprises a heavy chain variable domain set forth in SEQ ID NO: 14; and a light chain variable domain set forth in SEQ ID NO: 15. In certain embodiments according to (or as applied to) any of the embodiments above, the anti-CD8 antibody comprises a heavy chain variable domain set forth in SEQ ID NO: 16; and a light chain variable domain set forth in SEQ ID NO: 17. In certain embodiments according to (or as applied to) any of the embodiments above, the anti-CD8 antibody comprises a heavy chain variable domain set forth in SEQ ID NO: 18; and a light chain variable domain set forth in SEQ ID NO: 19. In certain embodiments according to (or as applied to) any of the embodiments above, the anti-CD8 antibody comprises a heavy chain variable domain set forth in SEQ ID NO: 20; and a light chain variable domain set forth in SEQ ID NO: 21. In certain embodiments according to (or as applied to) any of the embodiments above, the anti-CD8 antibody comprises a heavy chain variable domain set forth in SEQ ID NO: 22; and a light chain variable domain set forth in SEQ ID NO: 23. In certain embodiments according to (or as applied to) any of the embodiments above, the anti-CD8 antibody comprises a heavy chain variable domain set forth in SEQ ID NO: 24; and a light chain variable domain set forth in SEQ ID NO: 25. In certain embodiments according to (or as applied to) any of the embodiments above, the anti-CD8 antibody comprises a heavy chain variable domain set forth in SEQ ID NO: 26; and a light chain variable domain set forth in SEQ ID NO: 27.

In certain embodiments, provided is an isolated nucleic acid encoding the anti-CD8 antibody according to (or as applied to) any of the embodiments above. In certain embodiments, provided is an expression vector comprising the nucleic acid according to (or as applied to) any of the embodiments above. In certain embodiments, provided is a host cell comprising the nucleic acid or the expression vector according to (or as applied to) any of the embodiments above.

Also provided is a method of making the anti-CD8 antibody according to (or as applied to) any of the embodiments above, the method comprising: a) culturing the host cell according to (or as applied to) any of the embodiments above under conditions where the antibody is produced; and b) recovering the anti-CD8 antibody produced by the host cell. In certain embodiments according to (or as applied to) any of the embodiments above, the host cell is a eukaryotic cell. In certain embodiments according to (or as applied to) any of the embodiments above, the eukaryotic cell is a CHO cell. In certain embodiments according to (or as applied to) any of the embodiments above, the host cell is a prokaryotic cell. In certain embodiments according to (or as applied to) any of the embodiments above, the prokaryotic cell is an *E. coli* cell.

In certain embodiments according to (or as applied to) any of the embodiments above, the anti-CD8 antibody comprises a linker. In certain embodiments according to (or as applied to) any of the embodiments above, the linker is a desferrioxamine compound (e.g., N-succinyl-desferrioxamine). In certain embodiments the anti-CD8 antibody according to (or as applied to) any of the embodiments above is conjugated to a label. In certain embodiments according to (or as applied to) any of the embodiments above, the anti-CD8 antibody is conjugated to the label via the linker. In certain embodiments according to (or as applied to) any of the embodiments above, the label is a fluorescent dye, a radionuclide, or an enzyme. In certain embodiments according to (or as applied to) any of the embodiments above, the label is a radionuclide. In certain embodiments according to (or as applied to) any of the embodiments above, the radionuclide is $^{89}Zr$, $^{18}F$, $^{64}Cu$, or $^{124}I$.

Provided is a method of detecting $CD8^+$ cells in a subject, the method comprising: a) administering a labeled anti-CD8 antibody according to (or as applied to) any of the embodiments above, to the subject; and b) detecting binding of the labeled anti-CD8 antibody to $CD8^+$ cells in the subject, wherein the detection of the binding indicates the presence of $CD8^+$ cells. In certain embodiments according to (or as applied to) any of the embodiments above, detecting binding of the labeled anti-CD8 antibody to $CD8^+$ cells in the subject comprises imaging $CD8^+$ cells in the subject. In certain embodiments according to (or as applied to) any of the embodiments above, imaging $CD8^+$ cells in the subject comprises performing a positron emission tomography (PET) scan or positron emission tomography/computed tomography (PET/CT) scan on the subject. In certain embodiments according to (or as applied to) any of the embodiments above, the $CD8^+$ cells are $CD8^+$ T cells. In certain embodiments according to (or as applied to) any of the embodiments above, the subject is human or a non-human primate. In certain embodiments according to (or as applied to) any of the embodiments above, the non-human primate is a cynomolgus monkey or a rhesus monkey. In certain embodiments according to (or as applied to) any of the embodiments above, the subject is human. In certain embodiments according to (or as applied to) any of the embodiments above, the subject has cancer.

Provided is a method of predicting responsiveness of a subject having cancer to an immunotherapy or a cancer vaccine, the method comprising: a) administering the labeled anti-CD8 antibody according to (or as applied to) any of the embodiments above to the subject and; b) detecting binding of the labeled anti-CD8 antibody to $CD8^+$ T cells in a tumor tissue in the subject, wherein the detection of the binding indicates that the subject is likely to respond to the immunotherapy or the cancer vaccine. In certain embodiments according to (or as applied to) any of the embodiments above, detecting binding of the labeled anti-CD8 antibody to $CD8^+$ T cells in the tumor tissue of the subject comprises imaging the $CD8^+$ T cells in the subject. In certain embodiments according to (or as applied to) any of the embodiments above, imaging the $CD8^+$ T cells in the subject comprises performing a positron emission tomography (PET) scan or positron emission tomography/computed tomography (PET/CT) scan on the subject. In certain embodiments according to (or as applied to) any of the embodiments above, the method further comprises the step of: (c) administering a therapeutically effective amount of an immunotherapeutic agent or a cancer vaccine to the subject in whom the binding has been detected.

Also provided is a method of monitoring disease progression in a subject having cancer, the method comprising: a) administering the labeled anti-CD8 antibody according to (or as applied to) any of the embodiments above to the subject, and b) detecting binding of the labeled anti-CD8 antibody to $CD8^+$ T cells in the tumor tissue in the subject at a first time point and a second time point. In certain embodiments according to (or as applied to) any of the embodiments above, detecting binding of the labeled anti-CD8 antibody to $CD8^+$ T cells in the tumor tissue in the subject comprises imaging the $CD8^+$ T cells in the subject. In certain embodiments according to (or as applied to) any of the embodiments above, imaging the $CD8^+$ T cells in the subject comprises performing a positron emission tomography (PET) scan or positron emission tomography/computed tomography (PET/CT) scan on the subject. In certain embodiments according to (or as applied to) any of the embodiments above, the method further comprises the step of: (c) administering a therapeutically effective amount of an immunotherapeutic agent or a cancer vaccine to the subject wherein a level of $CD8^+$ T cells in the tumor tissue at the second time point is higher than the a level of $CD8^+$ T cells in the tumor tissue at the first time point.

Provided is a method of monitoring treatment progress in a subject having cancer who has or is receiving an immunotherapeutic agent or a cancer vaccine, the method comprising: i) administering the labeled anti-CD8 antibody according to (or as applied to) any of the embodiments above to the subject in conjunction with the immunotherapeutic agent or the cancer vaccine, and ii) detecting binding of the labeled anti-CD8 antibody to $CD8^+$ T cells in the tumor tissue at a first time point and a second time point. In certain embodiments according to (or as applied to) any of the embodiments above, detecting binding of the labeled anti-CD8 antibody to the $CD8^+$ T cells in the tumor tissue in the subject comprises imaging $CD8^+$ T cells in the subject. In certain embodiments according to (or as applied to) any of the embodiments above, imaging the $CD8^+$ T cells in the subject comprises performing a positron emission tomography (PET) scan or positron emission tomography/computed tomography (PET/CT) scan on the subject. In certain embodiments according to (or as applied to) any of the embodiments above, the labeled anti-CD8 antibody is administered before the immunotherapeutic agent or the cancer vaccine, wherein the first time point is after the administration of the labeled anti-CD8 antibody and prior to the administration of the immunotherapeutic agent or the cancer vaccine, and wherein the second time point is after the administration of the immunotherapeutic agent or the cancer vaccine. In certain embodiments according to (or as applied to) any of the embodiments above, the immunotherapeutic agent or the cancer vaccine is administered before the labeled anti-CD8 antibody, wherein the first time point is after the administration of the immunotherapeutic agent or the cancer vaccine and after the administration of the labeled anti-CD8 antibody, and wherein the second time point is after the first time point. In certain embodiments according to (or as applied to) any of the embodiments above, the immunotherapeutic agent is administered to the subject. In certain embodiments according to (or as applied to) any of the embodiments above, the immunotherapeutic agent is an anti-PDL1 antibody, an anti-PD1 antibody, an anti-TIGIT antibody, a TIGIT antagonist, an anti-CSF-1R antibody, an anti-CSF-1R antagonist, an anti-CEA antibody, an anti-CEA antagonist, an anti-CTLA4 antibody, a CTLA4 antagonist, an anti-OX40 antibody, or an OX40 agonist. In certain embodiments according to (or as applied to) any of the embodiments above, the immunotherapeutic agent is an anti-PD-L1 antibody. In certain embodiments according to (or as applied to) any of the embodiments above, the anti-PD-L1 antibody is administered in combination with one or more therapeutic agents. In certain embodiments according to (or as applied to) any of the embodiments above, the one or more therapeutic agents is Tarceva® (erlotinib), Zelboraf® (vemurafenib), Gazyva® (obinutuzumab), Avastin® (bevacizumab), Cotellic® (cobimetinib), Zelboraf® and Cotellic®, Alecensa® (alectinib), Kadcyla® (ado-trastuzumab emtansine), Herceptin® (trastuzumab), Perjeta® (pertuzumab), polatuzumab, INF-alpha, an anti-CD40 agent, an anti-OX40 antibody, an OX40 agonist, an anti-CSF-1R antibody, an anti-CEA antibody, an IDO inhibitor, or an anti-TIGIT antibody. In certain embodiments according to (or as applied to) any of the embodiments above, the immunotherapeutic agent is a bispecific antigen binding molecule that specifically binds CD3. In certain embodiments according to (or as applied to) any of the embodiments above, the bispecific antigen binding molecule is an antibody or an antigen-binding fragment thereof. In certain embodiments according to (or as applied to) any of the embodiments above, the immunotherapeutic agent is a bispecific antigen binding molecule that specifically binds CD16. In certain embodiments according to (or as applied to) any of the embodiments above, the bispecific antigen binding molecule is an antibody or an antigen-binding fragment thereof. In certain embodiments according to (or as applied to) any of the embodiments above, the bispecific antigen-binding molecule specifically binds CD16A. In certain embodiments according to (or as applied to) any of the embodiments above, the cancer vaccine is administered to the subject. In certain embodiments according to (or as applied to) any of the embodiments above, the cancer vaccine is a Personalized Cancer Vaccine (PCV).

Provided herein is a method of identifying gut microbial strains associated with responsiveness to treatment with an immunotherapeutic agent, the method comprising: a) obtaining gut microbiome samples from a population of subjects having cancer, which population comprises subjects who are responsive to treatment with the immunotherapeutic agent and subjects who are not responsive to treatment with the immunotherapeutic agent; b) analyzing the gut microbiome samples of the subjects who are responsive to the treatment and the gut microbiome samples of the subjects who are not responsive to the treatment; and c) identifying gut microbial strains associated with the subjects who are responsive to the treatment; wherein responsiveness is determined by detecting binding of the labeled anti-CD8 antibody according to (or as applied to) any of the embodiments above to $CD8^+$ T cells in a tumor tissue in the subjects, and wherein the detection of the binding indicates that the subjects are responsive to the immunotherapeutic agent. In certain embodiments according to (or as applied to) any of the embodiments above, the method further comprises preparing a microbiome-based drug comprising gut microbial strains associated with responsiveness to the immunotherapeutic agent. In certain embodiments according to (or as applied to) any of the embodiments above, the immunotherapeutic agent is an anti-PD-1 antibody. In certain embodiments according to (or as applied to) any of the embodiments above, the immunotherapeutic agent is an anti-PD-L1 antibody. In certain embodiments according to (or as applied to) any of the embodiments above, the anti-PD-L1 antibody is atezolizumab.

Also provided is a method of treating cancer in a subject who is not responsive an immunotherapeutic agent or is predicted to not be responsive to the immunotherapeutic agent, the method comprising: a) administering to the subject a microbiome-based drug that comprises gut microbial strains associated with patient responsiveness to the immunotherapeutic agent; and b) administering the immunotherapeutic agent to the subject. Further provided is a method of treating cancer in a subject who is not responsive an immunotherapeutic agent or is predicted to not be responsive to the immunotherapeutic agent, the method comprising: a) performing a fecal microbial transplant (FMT) on the subject using gut microbial strains associated with patient responsiveness; and b) administering the immunotherapeutic agent to the subject. In certain embodiments according to (or as applied to) any of the embodiments above, the immunotherapeutic agent is an anti-PD-1 antibody. In certain embodiments according to (or as applied to) any of the embodiments above, the immunotherapeutic agent is an anti-PD-L1 antibody. In certain embodiments according to (or as applied to) any of the embodiments above, the anti-PD-L1 antibody is atezolizumab.

BRIEF DESCRIPTION OF THE DRAWINGS

FIG. 2A is provides an alignment of the amino acid sequences of human CD8 (SEQ ID NO: 32), rhesus CD8 (SEQ ID NO: 31), and cynomolgous CD8 (SEQ ID NO: 32).

DETAILED DESCRIPTION OF THE INVENTION

Figure 1:
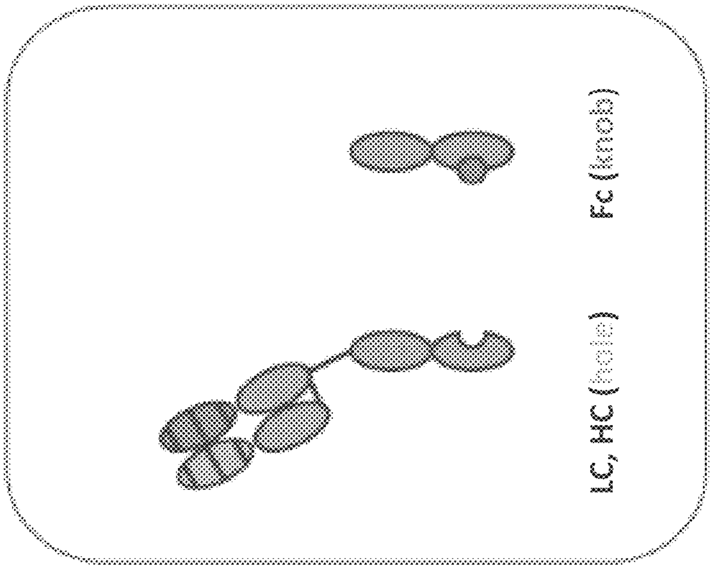
FIG. 1 provides an exemplary schematic of a one-armed anti-CD8 antibody comprising knob-in-hole mutations and LALAPG effector function mutations.

Provided herein are anti-CD8 antibody (including one-armed antibodies) that specifically bind human CD8, but do not activate or deplete CD8$^{+}$ T cells, induce CD8$^{+}$ T cell proliferation, or stimulate IFNγ production. Such anti-CD8 antibodies are capable of binding CD8 in non-human primates, such as rhesus and cynomolgous monkeys. Anti-CD8 antibodies having one or more of these characteristics can be useful for detecting the presence, localization, and/or quantities of CD8$^{+}$ cells (e.g., CD8$^{+}$ T cells). Provided are methods of using the anti-CD8 antibodies in methods for detecting CD8$^{+}$ T-cells in vivo. Also provided are methods of using the anti-CD8 antibodies herein in methods of predicting the responsiveness of a subject having cancer to treatment with an immunotherapeutic agent. In addition, provided are methods of using anti-CD8 antibodies herein to monitor disease progress and/or treatment progress in a subject with cancer who is receiving treatment with an immunotherapeutic agent.

Definitions

The term "antibody" herein is used in the broadest sense and encompasses various antibody structures, including but not limited to monoclonal antibodies, monovalent antibodies (e.g., one-armed antibodies), and antibody fragments so long as they exhibit the desired antigen-binding activity, i.e., binding to CD8 (such as a human CD8, a cynomolgous CD8, and/or a rhesus CD8).

A full length antibody is typically heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). However, other antibody formats, including, but not limited to, e.g., monovalent antibodies, one armed antibodies, Fabs, and (Fab')$_2$, are also contemplated. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains (CH) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H 1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, CT, 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, γ, ε, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, $6^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, MD (1991));

(c) antigen contacts occurring at amino acid residues 27c-36 (L1), 46-55 (L2), 89-96 (L3), (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

Anti-CD8 antibodies provided herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this invention (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc.), and human constant region sequences.

"Antibody fragments" comprise a portion of an intact antibody, preferably the antigen binding or variable region of the intact antibody. Examples of antibody fragments include Fab, Fab', $F(ab')_2$, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain (CH1). Each Fab fragment is monovalent with respect to antigen binding, i.e., it has a single antigen-binding site. Pepsin treatment of an antibody yields a single large $F(ab')_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The Fc fragment comprises the carboxy-terminal portions of both H chains held together by di sulfides. The effector functions of antibodies are determined by sequences in the Fc region, which region is also the part recognized by Fc receptors (FcR) found on certain types of cells.

A "variant Fc region" comprises an amino acid sequence which differs from that of a native sequence Fc region by virtue of at least one "amino acid modification" as herein defined. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. In one embodiment, the variant Fc region herein will possess at least about 80% homology, at least about 85% homology, at least about 90% homology, at least about 95% homology or at least about 99% homology with a native sequence Fc region. According to another embodiment, the variant Fc region herein will possess at least about 80% homology, at least about 85% homology, at least about 90% homology, at least about 95% homology or at least about 99% homology with an Fc region of a parent polypeptide.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., Nature 332:323-329 (1988); and Presta, Curr. Op. Struct. Biol. 2:593-596 (1992).

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, California. The ALIGN-2 program should be compiled for use on a UNIX operating system, preferably digital UNIX V4.0D. All sequence comparison parameters are set by the ALIGN-2 program and do not vary.

The term "specific binding" or "specifically binds to" or is "specific for" a particular polypeptide or an epitope on a particular polypeptide target as used herein can be exhibited, for example, by a molecule having a $K_D$ for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope. $K_D$ can be determined by methods known in the art, such as ELISA, surface plasmon resonance (SPR), fluorescence activated cell sorting (FACS) analysis, or radioimmunoprecipitation (RIA). Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer (such as, for example, tumor volume). The methods provided herein contemplate any one or more of these aspects of treatment.

An "effective amount" of an anti-CD8 antibody (or fragment thereof) or composition as disclosed herein is an amount sufficient to carry out a specifically stated purpose, e.g., for imaging $CD8^+$ T-cells in vivo. An "effective amount" can be determined empirically and by known methods relating to the stated purpose (such as imaging $CD8^+$ T-cells in vivo).

The term "therapeutically effective amount" refers to an amount of, e.g., an immunotherapeutic agent (such as an immunotherapeutic agent described elsewhere herein) effective to "treat" a disease or disorder in a subject (e.g., a mammal, such as a human). In the case of cancer, the therapeutically effective amount of the immunotherapeutic agent can reduce the number of cancer cells; reduce the tumor size or weight; inhibit (e.g., slow to some extent and preferably stop) cancer cell infiltration into peripheral organs; inhibit (e.g., slow to some extent and preferably stop) tumor metastasis; inhibit, to some extent, tumor growth; and/or relieve to some extent one or more of the symptoms associated with the cancer. To the extent the immunotherapeutic agent can prevent growth and/or kill existing cancer cells, it can be cytostatic and/or cytotoxic. In one embodiment, the therapeutically effective amount is a growth inhibitory amount. In another embodiment, the therapeutically effective amount is an amount that extends the survival of a patient. In another embodiment, the therapeutically effective amount is an amount that improves progression free survival of a patient.

An "individual" or "subject" is a mammal. Mammals include, but are not limited to, domesticated animals (e.g., cows, sheep, cats, dogs, and horses), primates (e.g., humans and non-human primates such as rhesus and cynomolgous monkeys), rabbits, and rodents (e.g., mice and rats). In certain embodiments, the individual or subject is a human.

As used herein, "responsiveness" refers to the development of a favorable response when a subject is undergoing or has undergone treatment with a therapeutic agent (e.g., an immunotherapeutic agent). An example of a favorable response is inhibition of tumor growth in a subject during or following treatment with a therapeutic agent (e.g., an immunotherapeutic agent), whereas an example of an unfavorable is continued growth or accelerated growth of a tumor in a subject during or following treatment with a therapeutic agent (e.g., an immunotherapeutic agent).

As used herein "monitoring disease progression" refers to assessing a subject (e.g., a subject diagnosed with cancer) at successive time intervals to determine whether disease symptoms have worsened, stabilized, or improved (i.e., become less severe). For example, monitoring the progression of cancer in a subject can, in certain instances, include monitoring changes in the weight or size of a tumor (such as tumor regression or tumor grown), time to progression, duration of survival, length of progression-free survival, overall response rate, duration of response, quality of life, expression and/or activity of disease markers (e.g., expression of certain genes and/or proteins), or other criteria known in the art. Additional approaches to monitoring disease progression in a patient with cancer can be employed, including for example, measurement of response to treatment via imaging techniques, which are described in further detail elsewhere herein.

As used herein "monitoring treatment progress" refers to assessing a subject (e.g., a subject diagnosed with cancer) at successive time intervals during or following treatment (e.g., treatment with an immunotherapeutic agent) to determine whether disease symptoms have worsened, stabilized, or improved (i.e., become less severe) as a result of the treatment. For example, treatment progress in a subject (e.g., a subject who has or is receiving treatment with an immunotherapeutic agent) can be monitored using the same criteria as those used to monitor disease progression.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

As used herein "in conjunction with" refers to the timing of the administration of, e.g., an anti-CD8 antibody described herein, relative to the administration of a second agent, e.g., an immunotherapeutic agent. For example, administration of an anti-CD8 antibody described herein in conjunction with an immunotherapeutic agent or a cancer vaccine (e.g., a Personalized Cancer Vaccine or "PCV") means that the anti-CD8 antibody may be administered before the immunotherapeutic agent or cancer vaccine has been administered, after the immunotherapeutic agent or cancer vaccine has been administered, concurrently with the administration of the immunotherapeutic agent or cancer vaccine, or simultaneously with the administration of the immunotherapeutic agent or cancer vaccine. Additional agents may be administered before or after the anti-CD8 antibody and the immunotherapeutic agent or cancer vaccine are administered. Additionally or alternatively, other agents may be administered between the sequential administration of the anti-CD8 antibody and the immunotherapeutic agent or cancer vaccine.

The term "detecting" is intended to include determining the presence or absence of a substance or quantifying the amount of a substance (such as CD8). The term thus refers to the use of the materials, compositions, and methods of the present invention for qualitative and quantitative determinations. In general, the particular technique used for detection is not critical for practice of the invention. For example, "detecting" according to the invention may include: observing the presence or absence of a CD8 polypeptide or a change in the levels of a CD8 polypeptide. In some embodiments, "detecting" may include detecting wild type CD8 levels (e.g., mRNA or polypeptide levels). Detecting may include quantifying a change (increase or decrease) of any value between 10% and 90%, or of any value between 30% and 60%, or over 100%, when compared to a control. Detecting may include quantifying a change of any value between 2-fold to 10-fold, inclusive, or more e.g., 100-fold.

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

Reference to "about" a value or parameter herein refers to the usual error range for the respective value readily known to the skilled person in this technical field. Reference to "about" a value or parameter herein includes (and describes) aspects that are directed to that value or parameter per se. For example, description referring to "about X" includes description of "X."

It is understood that aspects and embodiments of the invention described herein include "comprising," "consisting," and "consisting essentially of" aspects and embodiments.

All references cited herein, including patent applications and publications, are hereby incorporated by reference in their entirety.

Anti-CD8 Antibodies a. Functional Characteristics

An anti-CD8 antibody provided herein has one or more of following characteristics: (a) the antibody does not inhibit or stimulate the activation of $CD8^+$T cells; (b) the antibody does not induce $CD8^+$ T cell proliferation; (c) the antibody does not induce IFNγ production; (d) the antibody specifically binds human CD8; (e) the antibody specifically binds rhesus CD8; (f) the antibody specifically binds cynomolgous CD8; (g) the antibody does not bind $CD^{4+}$ cells; (g) the antibody does not bind $CD3^-$ cells; and (h) the antibody does not deplete $CD8^+$ T cells from the circulation. Such characteristics can be assessed using well known methods, e.g., methods used in the Examples below. In certain embodiments, IFN-γ release by $CD8^+$ T cells is assessed in vitro in the presence of purified $CD8^+$T cells, anti-CD3 antibody, and an anti-CD8 antibody provided herein. In certain embodiments, $CD8^+$ T cell proliferation is assessed in vitro in the presence of purified $CD8^+$ T cells, anti-CD3 antibody, and an anti-CD8 antibody provided herein. In certain embodiments, $CD8^+$ T cell proliferation is assessed in vitro in the presence of peripheral blood mononuclear cells (PBMC), tetanus toxoid, and an anti-CD8 antibody provided herein. In certain embodiments, $CD8^+$ T cell activation is assessed by measuring CD25 expression on T cells (e.g., via FACS) following stimulation of peripheral blood mononuclear cells (PBMC) with tetanus toxoid in the presence of an anti-CD8 antibody provided herein. In certain embodiments, non-depletion of $CD8^+$ T cells from circulation is assessed via FACS. For example, following the administration (such as injection) of an anti-CD8 antibody provided herein to a subject (such as a non-human primate), FACS is performed on a sample containing a total lymphocyte population using labeled anti-CD8 antibodies.

In some embodiments, an anti-CD8 antibody provided herein does not bind (e.g., specifically bind) to human $CD4^+$ T cells. In some embodiments, an anti-CD8 antibody provided herein does not bind (e.g., specifically bind) to human $CD3^-$ cells. In some embodiments, an anti-CD8 antibody provided herein does not bind (e.g., specifically bind) to either human $CD4^+$ T cells or human $CD3^-$ cells. In some embodiments, the lack of specific binding by an anti-CD8 antibody provided herein to human CD4+ T cells or human $CD3^-$ cells is detected via fluorescence activated cell sorting (FACS), as discussed in the Examples.

An anti-CD8 antibody is an antibody that binds to CD8 with sufficient affinity and specificity. In certain embodiments, the anti-CD8 antibody binds human CD8 with a $K_D$ of about any one of 1 μM, 100 nM, 50 nM, 40 nM, 30 nM, 20 nM, 10 nM, 5 nM, 1 nM, 0.5 nM, 0.1 nM, 0.05 nM, or nM (e.g. $10^{-8}$ M or less, e.g. from $10^{-8}$ M to $10^{-13}$ M, e.g., from $10^{-9}$ M to $10^{-13}$ M), including any range in between these values. In certain embodiments, the anti-CD8 antibody binds rhesus CD8 with a $K_D$ of about any one of 1 μM, 100 nM, 50 nM, 40 nM, 30 nM, 20 nM, 10 nM, 5 nM, 1 nM, 0.5 nM, 0.1 nM, 0.05 nM, or 0.001 nM (e.g. $10^{-8}$ M or less, e.g. from $10^{-8}$ M to $10^{-13}$ M, e.g., from $10^{-9}$ M to $10^{-13}$ M), including any range in between these values. In certain embodiments, the anti-CD8 antibody binds cynomolgus CD8 with a $K_D$ of 1 μM, 100 nM, 50 nM, 40 nM, 30 nM, 20 nM, 10 nM, 5 nM, 1 nM, 0.5 nM, 0.1 nM, 0.05 nM, or 0.001 nM (e.g. $10^{-8}$ M or less, e.g. from $10^{-8}$ M to $10^{-13}$ M, e.g., from $10^{-9}$ M to $10^{-13}$ M), including any range in between these values In certain embodiments, the anti-CD8 antibody binds (a) human CD8 with a $K_D$ of about 1 μM, 100 nM, 50 nM, 40 nM, 30 nM, 20 nM, 10 nM, 5 nM, 1 nM, 0.5 nM, 0.1 nM, 0.05 nM, or nM (e.g. $10^{-8}$ M or less, e.g. from $10^{-8}$ M to $10^{-13}$ M, e.g., from $10^{-9}$ M to $10^{-13}$ M), including any range in between these values, including any range in between these values; (b) rhesus CD8 with a $K_D$ of about 1 μM, 100 nM, 50 nM, 40 nM, 30 nM, 20 nM, 10 nM, 5 nM, 1 nM, 0.5 nM, 0.1 nM, 0.05 nM, or nM (e.g. $10^{-8}$ M or less, e.g. from $10^{-8}$ M to $10^{-13}$ M, e.g., from $10^{-9}$ M to $10^{-13}$ M), including any range in between these values, and (c) cynomolgus CD8 with a $K_D$ of about 1 μM, 100 nM, 50 nM, 30 nM, 20 nM, 10 nM, 5 nM, 1 nM, 0.5 nM, 0.1 nM, 0.05 nM, or 0.001 nM (e.g. $10^{-8}$ M or less, e.g. from $10^{-8}$ M to $10^{-13}$ M, e.g., from $10^{-9}$ M to $10^{-13}$ M), including any range in between these values. The $K_D$ of an anti-CD8 antibody provided herein for human CD8, rhesus CD8 and/or cynomolgous CD8 can be determined by any method known in the art, including, but not limited to, e.g., ELISA, fluorescence activated cell sorting (FACS) analysis, radioimmunoprecipitation (RIA), and surface plasmon resonance (SPR). In certain embodiments, the $K_D$ of an anti-CD8 antibody provided herein for human CD8, rhesus CD8 and/or cynomolgous CD8 is determined via SPR. In certain embodiments, the $K_D$ of an anti-CD8 antibody provided herein for human CD8, rhesus CD8 and/or cynomolgous CD8 is determined via FACS.

In certain embodiments, the anti-CD8 antibody provided herein does not bind (e.g., specifically bind) mouse CD8. In certain embodiments, the anti-CD8 antibody does not bind (e.g., specifically bind) rat CD8. In certain embodiments, the anti-CD8 antibody does not bind (e.g., specifically bind) to either mouse CD8 or rat CD8, e.g., as determined via SPR and/or FACS.

Provided herein are exemplary anti-CD8 antibodies having one or more of the functional characteristics described above. In some embodiments, provided is an anti-CD8 antibody comprising at least one, two, three, four, five, or six CDRs selected from (a) CDR-H1 comprising the amino acid sequence set forth in SEQ ID NO: 9; (b) CDR-H2 comprising the amino acid sequence set forth in SEQ ID NO: 10 or SEQ ID NO: 11; (c) CDR-H3 comprising the amino acid sequence set forth in SEQ ID NO: 12 or SEQ ID NO: 13; (d) CDR-L1 comprising the amino acid sequence set forth in SEQ ID NO: 1 or SEQ ID NO: 2; (e) CDR-L2 comprising the amino acid sequence set forth in SEQ ID NO: 3; and (f) CDR-L3 comprising the amino acid sequence set forth in SEQ ID NO: 4, SEQ ID NO: 5, SEQ ID NO: 6, SEQ ID NO: 7, or SEQ ID NO: 8.

In some embodiments, provided is an anti-CD8 antibody comprising six CDRs selected from (a) CDR-H1 comprising the amino acid sequence set forth in SEQ ID NO: 9; (b) CDR-H2 comprising the amino acid sequence set forth in SEQ ID NO: 10 or SEQ ID NO: 11; (c) CDR-H3 comprising the amino acid sequence set forth in SEQ ID NO: 12 or SEQ ID NO: 13; (d) CDR-L1 comprising the amino acid sequence set forth in SEQ ID NO: 1 or SEQ ID NO: 2; (e) CDR-L2 comprising the amino acid sequence set forth in SEQ ID NO: 3; and (f) CDR-L3 comprising the amino acid sequence set forth in SEQ ID NO: 4, SEQ ID NO: 5, SEQ ID NO: 6, SEQ ID NO: 7, or SEQ ID NO: 8.

In some embodiments, provided is an anti-CD8 antibody comprising at least one, at least two, or all three VH CDRs selected from (a) CDR-H1 comprising the amino acid sequence set forth in SEQ ID NO: 9; (b) CDR-H2 comprising the amino acid sequence set forth in SEQ ID NO: 10 or SEQ ID NO: 11; and (c) CDR-H3 comprising the amino acid sequence set forth in SEQ ID NO: 12 or SEQ ID NO: 13.

In some embodiments, provided is an anti-CD8 antibody comprising at least one, at least two, or all three VL CDRs selected from (a) CDR-L1 comprising the amino acid sequence set forth in SEQ ID NO: 1 or SEQ ID NO: 2; (b) CDR-L2 comprising the amino acid sequence set forth in SEQ ID NO: 3; and (c) CDR-L3 comprising the amino acid sequence set forth in SEQ ID NO: 4, SEQ ID NO: 5, SEQ ID NO: 6, SEQ ID NO: 7, or SEQ ID NO: 8.

In some embodiments, provided is an anti-CD8 antibody that comprises (a) a VH domain comprising at least one, at least two, or all three VH CDRs selected from (i) CDR-H1 comprising the amino acid sequence set forth in SEQ ID NO: 9; (ii) CDR-H2 comprising the amino acid sequence set forth in SEQ ID NO: 10 or SEQ ID NO: 11; and (iii) CDR-H3 comprising the amino acid sequence set forth in SEQ ID NO: 12 or SEQ ID NO: 13; and (b) a VL domain comprising at least one, at least two, or all three VL CDRs selected from (iv) CDR-L1 comprising the amino acid sequence set forth in SEQ ID NO: 1 or SEQ ID NO: 2; (v) CDR-L2 comprising the amino acid sequence set forth in SEQ ID NO: 3; and (vi) CDR-L3 comprising the amino acid sequence set forth in SEQ ID NO: 4, SEQ ID NO: 5, SEQ ID NO: 6, SEQ ID NO: 7, or SEQ ID NO: 8.

In some embodiments, provided is an anti-CD8 antibody comprising (a) CDR-H1 comprising the amino acid sequence set forth in SEQ ID NO: 9; (b) CDR-H2 comprising the amino acid sequence set forth in SEQ ID NO: 10; (c) CDR-H3 comprising the amino acid sequence set forth in SEQ ID NO: 12; (d) CDR-L1 comprising the amino acid sequence set forth in SEQ ID NO: 1; (e) CDR-L2 comprising the amino acid sequence set forth in SEQ ID NO: 3; and (f) CDR-L3 comprising an amino acid sequence set forth in SEQ ID NO: 4.

In some embodiments, provided is an anti-CD8 antibody comprising (a) CDR-H1 comprising the amino acid sequence set forth in SEQ ID NO: 9; (b) CDR-H2 comprising the amino acid sequence set forth in SEQ ID NO: 10; (c) CDR-H3 comprising the amino acid sequence set forth in SEQ ID NO: 12; (d) CDR-L1 comprising the amino acid sequence set forth in SEQ ID NO: 1; (e) CDR-L2 comprising the amino acid sequence set forth in SEQ ID NO: 3; and (f) CDR-L3 comprising an amino acid sequence set forth in SEQ ID NO: 5.

In some embodiments, provided is an anti-CD8 antibody comprising (a) CDR-H1 comprising the amino acid sequence set forth in SEQ ID NO: 9; (b) CDR-H2 comprising the amino acid sequence set forth in SEQ ID NO: 10; (c) CDR-H3 comprising the amino acid sequence set forth in SEQ ID NO: 12; (d) CDR-L1 comprising the amino acid sequence set forth in SEQ ID NO: 1; (e) CDR-L2 comprising the amino acid sequence set forth in SEQ ID NO: 3; and (f) CDR-L3 comprising an amino acid sequence set forth in SEQ ID NO: 6.

In some embodiments, provided is an anti-CD8 antibody comprising (a) CDR-H1 comprising the amino acid sequence set forth in SEQ ID NO: 9; (b) CDR-H2 comprising the amino acid sequence set forth in SEQ ID NO: 10; (c) CDR-H3 comprising the amino acid sequence set forth in SEQ ID NO: 12; (d) CDR-L1 comprising the amino acid sequence of SEQ ID NO: 1; (e) CDR-L2 comprising the amino acid sequence set forth in SEQ ID NO: 3; and (f) CDR-L3 comprising an amino acid sequence set forth in SEQ ID NO: 7.

In some embodiments, provided is an anti-CD8 antibody comprising (a) CDR-H1 comprising the amino acid sequence set forth in SEQ ID NO: 9; (b) CDR-H2 comprising the amino acid sequence set forth in SEQ ID NO: 10; (c) CDR-H3 comprising the amino acid sequence set forth in SEQ ID NO: 12; (d) CDR-L1 comprising the amino acid sequence set forth in SEQ ID NO: 1; (e) CDR-L2 comprising the amino acid sequence set forth in SEQ ID NO: 3; and (f) CDR-L3 comprising an amino acid sequence set forth in SEQ ID NO: 8.

In some embodiments, provided is an anti-CD8 antibody comprising (a) CDR-H1 comprising the amino acid sequence set forth in SEQ ID NO: 9; (b) CDR-H2 comprising the amino acid sequence set forth in SEQ ID NO: 11; (c) CDR-H3 comprising the amino acid sequence set forth in SEQ ID NO: 13; (d) CDR-L1 comprising the amino acid sequence set forth in SEQ ID NO: 1; (e) CDR-L2 comprising the amino acid sequence set forth in SEQ ID NO: 3; and (f) CDR-L3 comprising an amino acid sequence set forth in SEQ ID NO: 8.

In some embodiments, provided is an anti-CD8 antibody comprising (a) CDR-H1 comprising the amino acid sequence set forth in SEQ ID NO: 9; (b) CDR-H2 comprising the amino acid sequence set forth in SEQ ID NO: 10; (c) CDR-H3 comprising the amino acid sequence set forth in SEQ ID NO: 12; (d) CDR-L1 comprising the amino acid sequence set forth in SEQ ID NO: 2; (e) CDR-L2 comprising the amino acid sequence set forth in SEQ ID NO: 3; and (f) CDR-L3 comprising an amino acid sequence set forth in SEQ ID NO: 8.

The amino acid sequences of SEQ ID NOs: 1-13 are provided in Table 1 below:

TABLE 1

| | | |
|---|---|---|
| SISQY (SEQ ID NO: 1) | SISKY (SEQ ID NO: 2) | SGSTLQ (SEQ ID NO: 3) |
| HNENPL (SEQ ID NO: 4) | HNEFPV (SEQ ID NO: 5) | HNEFPP (SEQ ID NO: 6) |
| VNEFPP (SEQ ID NO: 7) | VNEFPV (SEQ ID NO: 8) | GFNIKDTYIH (SEQ ID NO: 9) |
| RIDPANDNTLYASKFQG (SEQ ID NO: 10) | RIDPANDNTLYARKFQG (SEQ ID NO: 11) | GRGYGYYVFDH (SEQ ID NO: 12) |
| TRGYGYYVFDT (SEQ ID NO: 13) | | |

In some embodiments, the anti-CD8 antibody comprises a heavy chain variable domain (VH) having the amino acid sequence set forth in any one of SEQ ID NO: 14, SEQ ID NO: 16, SEQ ID NO: 18, SEQ ID NO: 20, SEQ ID NO: 22, SEQ ID NO: 24, or SEQ ID NO: 26. In some embodiments, the anti-CD8 antibody comprises a light chain variable domain (VL) having the amino acid sequence set forth in any one of SEQ ID NO: 15, SEQ ID NO: 17, SEQ ID NO: 19, SEQ ID NO: 21, SEQ ID NO: 23, SEQ ID NO: 25, or SEQ ID NO: 27. In some embodiments, the anti-CD8 antibody comprises a heavy chain variable domain (VH) having the amino acid sequence set forth in any one of SEQ ID NO: 14, SEQ ID NO: 16, SEQ ID NO: 18, SEQ ID NO: 20, SEQ ID NO: 22, SEQ ID NO: 24, or SEQ ID NO: 26 and a light chain variable domain (VL) having the amino acid sequence set forth in any one of SEQ ID NO: 15, SEQ ID NO: 17, SEQ ID NO: 19, SEQ ID NO: 21, SEQ ID NO: 23, SEQ ID NO: 25, or SEQ ID NO: 27.

In some embodiments, the anti-CD8 antibody comprises a VH as in any of the embodiments provided above, and a VL as in any of the embodiments provided above.

In some embodiments, the anti-CD8 antibody comprises the VH and/or the VL sequences set forth in SEQ ID NO: 14 and SEQ ID NO: 15, respectively, including post-translational modifications of those sequences. In some embodiments, the anti-CD8 antibody comprises the VH and/or the VL sequences set forth in SEQ ID NO: 16 and SEQ ID NO: 17, respectively, including post-translational modifications of those sequences. In some embodiments, the anti-CD8 antibody comprises the VH and/or the VL sequences set forth in SEQ ID NO: 18 and SEQ ID NO: 19, respectively, including post-translational modifications of those sequences. In some embodiments, the anti-CD8 antibody comprises the VH and/or the VL sequences set forth in SEQ ID NO: 20 and SEQ ID NO: 21, respectively, including post-translational modifications of those sequences. In some embodiments, the anti-CD8 antibody comprises the VH and/or the VL sequences set forth in SEQ ID NO: 22 and SEQ ID NO: 23, respectively, including post-translational modifications of those sequences. In some embodiments, the anti-CD8 antibody comprises the VH and/or the VL sequences set forth in SEQ ID NO: 24 and SEQ ID NO: 25, respectively, including post-translational modifications of those sequences set forth. In some embodiments, the anti-CD8 antibody comprises the VH and/or the VL sequences set forth in SEQ ID NO: 26 and SEQ ID NO: 27, respectively, including post-translational modifications of those sequences.

In some embodiments, the anti-CD8 antibody comprises the VH and the VL sequences set forth in SEQ ID NO: 14 and SEQ ID NO: 15, respectively, including post-translational modifications of those sequences. In some embodiments, the anti-CD8 antibody comprises the VH and the VL sequences set forth in SEQ ID NO: 16 and SEQ ID NO: 17, respectively, including post-translational modifications of those sequences. In some embodiments, the anti-CD8 antibody comprises the VH and the VL sequences set forth in SEQ ID NO: 18 and SEQ ID NO: 19, respectively, including post-translational modifications of those sequences. In some embodiments, the anti-CD8 antibody comprises the VH and the VL sequences set forth in SEQ ID NO: 20 and SEQ ID NO: 21, respectively, including post-translational modifications of those sequences. In some embodiments, the anti-CD8 antibody comprises the VH and the VL sequences set forth in SEQ ID NO: 22 and SEQ ID NO: 23, respectively, including post-translational modifications of those sequences. In some embodiments, the anti-CD8 antibody comprises the VH and the VL sequences set forth in SEQ ID NO: 24 and SEQ ID NO: 25, respectively, including post-translational modifications of those sequences. In some embodiments, the anti-CD8 antibody comprises the VH and the VL sequences set forth in SEQ ID NO: 26 and SEQ ID NO: 27, respectively, including post-translational modifications of those sequences. The amino acid sequences of SEQ ID Nos: 14-27 are provided below:

(SEQ ID NO: 14)
EVQLVQSGAEVKKPGASVKVSCKASGFNIKDTYIHWVRQAPGQGLEWIG
RIDPANDNTLYASKFQGRATITADTSTSTAYLELSSLRSEDTAVYYCGR
GYGYYVFDHWGQGTLVTVSS (SEQ ID NO: 15)
DVQITQSPSSLSASVGDRVTITCRTSRSISQYLAWYQEKPGKTNKLLIY
SGSTLQSGIPSRFSGSGSGTDFTLTISSLQPEDFATYYCQQHNENPLTF
GQGTKVEIK (SEQ ID NO: 16)
EVQLVQSGAEVKKPGASVKVSCKASGFNIKDTYIHWVRQAPGQGLEWIG
RIDPANDNTLYASKFQGRATITADTSTSTAYLELSSLRSEDTAVYYCGR
GYGYYVFDHWGQGTLVTVSSASTKGPSVFPLAPSSKSTSGGTAALGCLV

-continued

KDYFPEPVTVSWNSGALTSGVHTFPAVLQSSGLYSLSSVVTVPSSSLGT
QTYICNVNHKPSNTKVDKKVEPKSCDKTHT (SEQ ID NO: 17)
DVQITQSPSSLSASVGDRVTITCRTSRSISQYLAWYQEKPGKTNKLLIY
SGSTLQSGIPSRESGSGSGTDFTLTISSLQPEDFATYYCQQHNEFPVTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSENRGEC (SEQ ID NO: 18)
EVQLVQSGAEVKKPGASVKVSCKASGFNIKDTYIHWVRQAPGQGLEWIG
RIDPANDNTLYASKFQGRATITADTSTSTAYLELSSLRSEDTAVYYCGR
GYGYYVFDHWGQGTLVTVSSASTKGPSVFPLAPSSKSTSGGTAALGCLV
KDYFPEPVTVSWNSGALTSGVHTFPAVLQSSGLYSLSSVVTVPSSSLGT
QTYICNVNHKPSNTKVDKKVEPKSCDKTHT (SEQ ID NO: 19)
DVQITQSPSSLSASVGDRVTITCRTSRSISQYLAWYQEKPGKINKLLIY
SGSTLQSGIPSRESGSGSGTDFTLTISSLQPEDFATYYCQQHNEFPPTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC (SEQ ID NO: 20)
EVQLVQSGAEVKKPGASVKVSCKASGFNIKDTYIHWVRQAPGQGLEWIG
RIDPANDNTLYASKFQGRATITADTSTSTAYLELSSLRSEDTAVYYCGR
GYGYYVFDHWGQGTLVTVSSASTKGPSVFPLAPSSKSTSGGTAALGCLV
KDYFPEPVTVSWNSGALTSGVHTFPAVLQSSGLYSLSSVVTVPSSSLGT
QTYICNVNHKPSNTKVDKKVEPKSCDKTHT (SEQ ID NO: 21)
DVQITQSPSSLSASVGDRVTITCRTSRSISQYLAWYQEKPGKTNKLLIY
SGSTLQSGIPSRESGSGSGTDFTLTISSLQPEDFATYYCQQVNEFPPTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC (SEQ ID NO: 22)
EVQLVQSGAEVKKPGASVKVSCKASGFNIKDTYIHWVRQAPGQGLEWIG
RIDPANDNTLYASKFQGRATITADTSTSTAYLELSSLRSEDTAVYYCGR
GYGYYVFDHWGQGTLVTVSS (SEQ ID NO: 23)
DVQITQSPSSLSASVGDRVTITCRTSRSISQYLAWYQEKPGKTNKLLIY
SGSTLQSGIPSRESGSGSGTDFTLTISSLQPEDFATYYCQQVNEFPVTF
GQGTKVEIK (SEQ ID NO: 24)
EVQLVQSGAEVKKPGASVKVSCKASGFNIKDTYIHWVRQAPGQGLEWIG
RIDPANDNTLYARKFQGRATITADTSTSTAYLELSSLRSEDTAVYYCTR
GYGYYVFDTWGQGTLVTVSSASTKGPSVFPLAPSSKSTSGGTAALGCLV

-continued

```
KDYFPEPVTVSWNSGALTSGVHTFPAVLQSSGLYSLSSVVTVPSSSLGT

QTYICNVNHKPSNTKVDKKVEPKSCDKTHT

                                    (SEQ ID NO: 25)
DVQITQSPSSLSASVGDRVTITCRTSRSISQYLAWYQEKPGKTNKLLIY

SGSTLQSGIPSRFSGSGSGTDFTLTISSLQPEDFATYYCQQVNEFPVTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

                                    (SEQ ID NO: 26)
EVQLVQSGAEVKKPGASVKVSCKASGFNIKDTYIHWVRQAPGQGLEWIG

RIDPANDNTLYASKFQGRATITADTSTSTAYLELSSLRSEDTAVYYCGR

GYGYYVFDHWGQGTLVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKKVEPKSCDKTHT

                                    (SEQ ID NO: 27)
DVQITQSPSSLSASVGDRVTITCRTSRSISKYLAWYQEKPGKTNKLLIY

SGSTLQSGIPSRFSGSGSGTDFTLTISSLQPEDFATYYCQQVNEFPVTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

b. Pharmacokinetic Characteristics

In some embodiments, an anti-CD8 antibody provided herein is cleared renally and hepatically. In some embodiments, an anti-CD8 antibody provided herein is cleared renally or hepatically. In some embodiments, an anti-CD8 antibody provided herein is cleared (such as predominantly cleared) by the renal system.

c. Monovalent Anti-CD8 Antibodies

In some embodiments, the anti-CD8 antibody is a monovalent antibody. In some embodiments, the monovalent antibody is a one-armed antibody comprising a full length heavy chain, a light chain, and an Fc. In some embodiments, the one armed antibody comprises a full-length heavy chain that comprises a VH domain comprising an amino acid sequence set forth in any one of SEQ ID Nos; 14, 16, 18, 20, 22, 24, and 26. Additionally or alternatively, the one-armed antibody comprises a full-length light chain that comprises a VL domain comprising an amino acid sequence set forth in any one of SEQ ID Nos: 15, 17, 19, 21, 23, 25, and 27. In some embodiments, the full-length heavy chain comprises the VH sequence set forth in SEQ ID NO: 14 and the full length light chain comprises the VL sequence set forth in SEQ ID NO: 15, including post-translational modifications of those sequences. In some embodiments, the full-length heavy chain comprises the VH sequence set forth in SEQ ID NO: 16 and the full length light chain comprises the VL sequence set forth in SEQ ID NO: 17, including post-translational modifications of those sequences. In some embodiments, the full-length heavy chain comprises the VH sequence set forth in SEQ ID NO: 18 and the full length light chain comprises the VL sequence set forth in SEQ ID NO: 19, including post-translational modifications of those sequences. In some embodiments, the full-length heavy chain comprises the VH sequence set forth in SEQ ID NO: 20 and the full length light chain comprises the VL sequence set forth in SEQ ID NO: 21, including post-translational modifications of those sequences. In some embodiments, the full-length heavy chain comprises the VH sequence set forth in SEQ ID NO: 22 and the full length light chain comprises the VL sequence set forth in SEQ ID NO: 23, including post-translational modifications of those sequences. In some embodiments, the full-length heavy chain comprises the VH sequence set forth in SEQ ID NO: 24 and the full length light chain comprises the VL sequence set forth in SEQ ID NO: 25, including post-translational modifications of those sequences. In some embodiments, the full-length heavy chain comprises the VH sequence set forth in SEQ ID NO: 26 and the full length light chain comprises the VL sequence set forth in SEQ ID NO: 27, including post-translational modifications of those sequences.

In some embodiments, the full length heavy chain comprises one or more "knob" mutations, and the Fc comprises one or more "hole" mutations. In some embodiments, the full length heavy chain comprises one or more "hole" mutations, and the Fc comprises one or more "knob" mutations. An exemplary schematic of a one-armed anti-CD8 antibody provided herein is provided in FIG. 1.

In certain embodiments, the one-armed anti-CD8 antibody comprises a variant IgG1 Fc domain comprising an L234A mutation, wherein the amino acid residue is numbered according to the EU numbering system. In certain embodiments, the one-armed anti-CD8 antibody comprises (such as further comprises) a variant IgG1 Fc domain comprising an L235A mutation, wherein the amino acid residue is numbered according to the EU numbering system. In certain embodiments, the one-armed anti-CD8 antibody comprises (such as further comprises) a variant IgG1 Fc domain comprising a P329G mutation, wherein the amino acid residue is numbered according to the EU numbering system. In certain embodiments, the one-armed anti-CD8 antibody comprises a variant IgG1 Fc domain comprising L234A, L235A, and P329G mutations, wherein the amino acid residue is numbered according to the EU numbering system. In certain embodiments, the anti-CD8 antibody comprising a variant IgG1 Fc domain comprising one or more of L234A, L235A, and P329G mutations (such as any two or all three of L234A, L235A, and P329G mutations).

In some embodiments, a one armed anti-CD8 antibody comprises a full length heavy chain comprising (such as consisting of) the amino acid sequence set forth in SEQ ID NO: 28. In some embodiments, a one-armed anti-CD8 antibody comprises a light chain comprising (such as consisting of) the amino acid sequence set forth in SEQ ID NO: 29. In some embodiments, a one-armed anti-CD8 antibody comprises an Fc comprising (such as consisting of) the amino acid sequence set forth in SEQ ID NO: 30. In some embodiments, a one armed anti-CD8 antibody comprises a full length heavy chain comprising (such as consisting of) the amino acid sequence set forth in SEQ ID NO: 28, a light chain comprising (such as consisting of) the amino acid sequence set forth in SEQ ID NO: 29, and an Fc comprising (such as consisting of) the amino acid sequence set forth in SEQ ID NO: 30. The amino acid sequences set forth in SEQ ID NOs: 28, 29, and 30 are provided below:

(SEQ ID NO: 28)
```
EVQLVQSGAEVKKPGASVKVSCKASGFNIKDTYIHWVRQAPGQGLEWIG
RIDPANDNTLYASKFQGRATITADTSTSTAYLELSSLRSEDTAVYYCGR
GYGYYVFDHWGQGTLVTVSSASTKGPSVFPLAPSSKSTSGGTAALGCLV
KDYFPEPVTVSWNSGALTSGVHTFPAVLQSSGLYSLSSVVTVPSSSLGT
QTYICNVNHKPSNTKVDKKVEPKSCDKTHTCPPCPAPEAAGGPSVFLFP
PKPKDTLMISRTPEVTCVVVDVSHEDPEVKFNWYVDGVEVHNAKTKPRE
EQYNSTYRVVSVLTVLHQDWLNGKEYKCKVSNKALGAPIEKTISKAKGQ
PREPQVYTLPPSREEMTKNQVSLSCAVKGFYPSDIAVEWESNGQPENNY
KTTPPVLDSDGSFFLVSKLTVDKSRWQQGNVFSCSVMHEALHNHYTQKS
LSLSPGK
```

(SEQ ID NO: 29)
```
DVQITQSPSSLSASVGDRVTITCRTSRSISQYLAWYQEKPGKTNKLLIY
SGSTLQSGIPSRFSGSGSGTDFTLTISSLOPEDFATYYCQQVNEFPPTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSENRGEC
```

(SEQ ID NO: 30)
```
DKTHTCPPCPAPEAAGGPSVFLFPPKPKDTLMISRTPEVTCVVVDVSHE
DPEVKFNWYVDGVEVHNAKTKPREEQYNSTYRVVSVLTVLHQDWLNGKE
YKCKVSNKALGAPIEKTISKAKGQPREPQVYTLPPSREEMTKNQVSLWC
LVKGFYPSDIAVEWESNGQPENNYKTTPPVLDSDGSFFLYSKLTVDKSR
WQQGNVFSCSVMHEALHNHYTQKSLSLSPGK
```

d. Antibody Fragments

In some embodiments, provided are fragments of an anti-CD8 antibody. In some embodiments, the antibody fragment is an antigen binding fragment. In some embodiments, the antigen binding fragment is selected from the group consisting of a Fab fragment, a Fab' fragment, a Fab'-SH, a $F(ab')_2$ fragment, a scFv, or an Fv.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; 5,587,458. The antibody fragment may also be a "linear antibody," e.g., as described in U.S. Pat. No. 5,641,870 for example. Such linear antibody fragments may be monospecific or bispecific.

For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and $F(ab')_2$ fragments comprising salvage receptor binding epitope residues and having increased in vivo half-life, see U.S. Pat. No. 5,869,046.

e. Antibody Variants and Antibody Modifications

In certain embodiments, amino acid sequence variants of the anti-CD8 antibodies described herein are contemplated. For example, it may be desirable to improve the binding affinity and/or other biological properties of the anti-CD8 antibody. Amino acid sequence variants of the anti-CD8 antibody may be prepared by introducing appropriate modifications into the nucleotide sequence encoding the protein, or by peptide synthesis. Such modifications include, for example, deletions from, and/or insertions into and/or substitutions of residues within the amino acid sequences (such as in one or more CDRs and/or framework sequences or in a $V_H$ and/or a $V_L$ domain) of the anti-CD8 antibody. Any combination of deletion, insertion, and substitution can be made to arrive at the final construct, provided that the final construct possesses the desired characteristics (e.g., as described elsewhere herein).

"Anti-CD8 antibody variant" means a polypeptide, for example, an anti-CD8 antibody possessing the desired characteristics described herein comprises a $V_H$ and/or a $V_L$ that has at least about 80% amino acid sequence identity with a $V_H$ and/or a $V_L$ of an anti-CD8 antibody described herein. Such anti-CD8 antibody variants include, for instance, antibodies wherein one or more amino acid residues are added to or deleted from the $V_H$ and/or a $V_L$ domain. Ordinarily, an anti-CD8 antibody variant will have at least about 80% amino acid sequence identity, alternatively at least about any of 85%, 90%, 95%, 96%, 97%, 98%, or 99% amino acid sequence identity, to an anti-CD8 antibody described herein. Optionally, variant anti-CD8 antibodies will have no more than one conservative amino acid substitution as compared to an anti-CD8 antibody sequence provided herein, alternatively no more than about any of 2, 3, 4, 5, 6, 7, 8, 9, or 10 conservative amino acid substitution as compared to an anti-CD8 antibody sequence provided herein.

In certain embodiments, anti-CD8 antibody variants having one or more amino acid substitutions, insertions, and/or deletions are provided. Sites of interest for substitutional mutagenesis include the HVRs and FRs. Conservative substitutions are shown in Table 2 under the heading of "conservative substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

| Original Residue | Exemplary Substitutions | Conservative Substitutions |
|---|---|---|
| Ala (A) | Val; Leu; Ile | Val |
| Arg (R) | Lys; Gln; Asn | Lys |

TABLE 2-continued

| Original Residue | Exemplary Substitutions | Conservative Substitutions |
|---|---|---|
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the anti-CD8 antibody variant can be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, Biochemistry second ed., pp. 73-75, Worth Publishers, New York (1975)):

(1) non-polar: Ala (A), Val (V), Leu (L), Ile (I), Pro (P), Phe (F), Trp (W), Met (M)

(2) uncharged polar: Gly (G), Ser (S), Thr (T), Cys (C), Tyr (Y), Asn (N), Gln (Q)

(3) acidic: Asp (D), Glu (E)

(4) basic: Lys (K), Arg (R), His (H)

Alternatively, naturally occurring residues may be divided into groups based on common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

In some embodiments, an anti-CD8 antibody provided herein comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 14, SEQ ID NO: 16, SEQ ID NO: 18, SEQ ID NO: 20, SEQ ID NO: 22, SEQ ID NO: 24, or SEQ ID NO: 26. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CD8 antibody comprising that sequence retains the ability to bind to CD8 (e.g., a human CD8, a rhesus CD8, and/or a cynomolgous CD8). In certain embodiments, a total of 1 to 10 amino acids have been substituted, inserted and/or deleted in SEQ ID NO: SEQ ID NO: 14, SEQ ID NO: 16, SEQ ID NO: 18, SEQ ID NO: 20, SEQ ID NO: 22, SEQ ID NO: 24, or SEQ ID NO: 26. In certain embodiments, substitutions, insertions, or deletions occur in regions outside the CDRs (i.e., in the FRs). In certain embodiments an anti-CD8 antibody comprises the VH sequence set forth in SEQ ID NO: 14, SEQ ID NO: 16, SEQ ID NO: 18, SEQ ID NO: 20, SEQ ID NO: 22, SEQ ID NO: 24, or SEQ ID NO: 26, including post-translational modifications of that sequence.

In certain embodiments an anti-CD8 antibody provided herein comprises a light chain variable domain (VL) having at least 90%, 91%, 92%, 93%, 94%, 95%, 96%, 97%, 98%, 99%, or 100% sequence identity to the amino acid sequence of SEQ ID NO: 15, SEQ ID NO: 17, SEQ ID NO: 19, SEQ ID NO: 21, SEQ ID NO: 23, SEQ ID NO: 25 or SEQ ID NO:27. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CD8 antibody comprising that sequence retains the ability to bind to CD8 (e.g., a human CD8, a rhesus CD8, and/or a cynomolgous CD8). In certain embodiments, a total of 1 to 10 amino acids have been substituted, inserted and/or deleted in SEQ ID NO: 15, SEQ ID NO: 17, SEQ ID NO: 19, SEQ ID NO: 21, SEQ ID NO: 23, SEQ ID NO: 25 or SEQ ID NO: 27. In certain embodiments, substitutions, insertions, or deletions occur in regions outside the CDRs (i.e., in the FRs). In certain embodiments an anti-CD8 antibody comprises the VH sequence set forth in SEQ ID NO: 15, SEQ ID NO: 17, SEQ ID NO: 19, SEQ ID NO: 21, SEQ ID NO: 23, SEQ ID NO: 25 or SEQ ID NO: 27, including post-translational modifications of that sequence.

In some embodiments, an anti-CD8 antibody provided herein comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 20. In certain embodiments, the VH sequence having at least 90%, 91%, 92%, 93%, 94%, 95%, 96%, 97%, 98%, or 99% identity contains substitutions (e.g., conservative substitutions), insertions, or deletions relative to SEQ ID NO: 20, but an anti-CD8 antibody comprising that sequence retains the ability to bind to CD8 (e.g., human CD8, rhesus CD8, and/or cynomolgous CD8). In certain embodiments, a total of 1 to 10 amino acids have been substituted, inserted and/or deleted in SEQ ID NO: 20. In certain embodiments, substitutions, insertions, or deletions occur in regions outside the CDRs (i.e., in the FRs). Optionally, the anti-CD8 antibody heavy chain comprises the VH sequence in SEQ ID NO: 20, including post-translational modifications of that sequence. Additionally or alternatively, an anti-CD8 antibody provided herein comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 21. In certain embodiments, the VL having at least 90%, 91%, 92%, 93%, 94%, 95%, 96%, 97%, 98%, or 99% identity contains substitutions (e.g., conservative substitutions), insertions, or deletions relative to SEQ ID NO: 21, but an anti-CD8 antibody comprising that sequence retains the ability to bind to CD8 (e.g., human CD8, rhesus CD8, and/or cynomolgous CD8). In certain embodiments, a total of 1 to 10 amino acids have been substituted, inserted and/or deleted in SEQ ID NO: 21. In certain embodiments, substitutions, insertions, or deletions occur in regions outside the CDRs (i.e., in the FRs). Optionally, the anti-CD8 antibody heavy chain comprises the VL sequence in 21, including post-translational modifications of that sequence.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more CDRs so long as such alterations do not substantially reduce the ability of the antibody to CD8. For example, conservative alterations (e.g., conservative substitutions as provided herein) that do not substantially reduce binding affinity may be made in CDRs. Such alterations may be outside of CDRs "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

f. Fc Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, an anti-CD8 antibody provided herein comprises an Fc variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 2 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166: 1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96 ® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 234, 235, 237, 238, 265, 269, 270, 297, 327 and 329 (see, e.g., U.S. Pat. No. 6,737,056). Such Fc mutants include Fc mutants with substitutions at two or more of amino acid positions 265, 269, 270, 297 and 327 wherein the amino acid residue is numbered according to the EU numbering system, including the so-called "DANA" Fc mutant with substitution of residues 265 and 297 to alanine (U.S. Pat. No. 7,332,581).

In certain embodiments, such Fc mutants comprise substitutions at two or more of amino acid positions 234, 235, and 329. In certain embodiments, the anti-CD8 antibody comprises a variant IgG1 Fc domain comprising an L234A mutation, wherein the amino acid residue is numbered according to the EU numbering system. In certain embodiments, the anti-CD8 antibody comprises a variant IgG1 Fc domain comprising (such as further comprising) an L235A mutation, wherein the amino acid residue is numbered according to the EU numbering system. In certain embodiments, the anti-CD8 antibody comprises a variant IgG1 Fc domain comprising (such as further comprising) a P329G mutation, wherein the amino acid residue is numbered according to the EU numbering system. In certain embodiments, the anti-CD8 antibody comprises a variant IgG1 Fc domain comprising L234A, L235A, and P329G mutations, wherein the amino acid residue is numbered according to the EU numbering system. In certain embodiments, the anti-CD8 antibody comprising a variant IgG1 Fc domain comprising one or more of L234A, L235A, and P329G mutations (such as any two or all three of L234A, L235A, and P329G mutations).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. No. 5,648,260; 5,624,821; and WO 94/29351 concerning other examples of Fc region variants.

g. "Knobs-into-Holes" Variants

In certain embodiments, the Fc domain of an anti-CD8 antibody provided herein comprises "knobs-into-holes" mutations. "Knobs-into-holes" is a design strategy for engineering antibody heavy chain homodimers for heterodimerization (e.g., for the efficient production of bispecific antibodies, multispecific antibodies, or one-armed antibodies). Generally, such technology involves introducing a protuberance ("knob") at the interface of a first polypeptide (such as a first CH3 domain in a first antibody heavy chain) and a corresponding cavity ("hole") in the interface of a second polypeptide (such as a second CH3 domain in a second antibody heavy chain), such that the protuberance can be positioned in the cavity so as to promote heterodimer formation and hinder homodimer formation. Protuberances are constructed by replacing small amino acid side chains from the interface of the first polypeptide (such as a first CH3 domain in a first antibody heavy chain) with larger side chains (e.g. arginine, phenylalanine, tyrosine or tryptophan). Compensatory cavities of identical or similar size to the protuberances are created in the interface of the second polypeptide (such as a second CH3 domain in a second antibody heavy chain) by replacing large amino acid side chains with smaller ones (e.g. alanine, serine, valine, or threonine). The protuberance and cavity can be made by altering the nucleic acid encoding the polypeptides, e.g. by site-specific mutagenesis, or by peptide synthesis. In some embodiments a knob modification comprises the amino acid substitution T366W in one of the two subunits of the Fc domain, and the hole modification comprises the amino acid substitutions T366S, L368A and Y407V in the other one of the two subunits of the Fc domain. In some embodiments, the subunit of the Fc domain comprising the knob modification additionally comprises the amino acid substitution S354C, and the subunit of the Fc domain comprising the hole modification additionally comprises the amino acid substitution Y349C. Introduction of these two cysteine residues results in the formation of a disulfide bridge between the two subunits of the Fc region, thus further stabilizing the dimer (Carter, J Immunol Methods 248, 7-15 (2001)). Exemplary sets of knobs-into-holes mutations include, but not limited to, those shown in Table 3 below:

TABLE 3

| | | | | | | | | |
|---|---|---|---|---|---|---|---|---|
| Fc domain monomer 1 | Y407T | Y407A | F405A | T394S | T366S L358A Y407V | T394W Y407T | T394S Y407A | T366W T394S |
| Fc domain monomer 2 | T366Y | T366W | T394W | F405W | T366W | T366Y F405A | T366W F405W | F405W Y407A |

In some embodiments, an anti-CD8 antibody provided herein comprises an antibody heavy chain comprising a first Fc domain, an antibody light chain, and a second Fc domain, wherein the antibody heavy chain pairs with the antibody light chain, and wherein the first Fc domain and the second Fc domain meet at an interface. In some embodiments, the interface of the first Fc domain comprises a cavity, and wherein the interface of the second Fc domain comprises the protuberance which is positionable in the cavity in the interface of the first Fc domain; or wherein the interface of the second Fc domain comprises a cavity, and wherein the interface of the first Fc domain comprises the protuberance which is positionable in the cavity in the interface of the second Fc domain. In some embodiments, the first Fc domain comprises T366S, L358A, and Y407V mutations, the second Fc domain comprises a T366W mutation, wherein the amino acid residues are numbered according to the EU numbering system. In some embodiments, the first Fc domain comprises a T366W mutation, and the second Fc domain comprises T366S, L358A, and Y407V mutations, wherein the amino acid residues are numbered according to the EU numbering system.

Further details regarding "knobs-into-holes" technology is described in, e.g., U.S. Pat. No. 5,731,168; 7,695,936; WO 2009/089004; US 2009/0182127; Marvin and Zhu, *Acta Pharmacologica Sincia* (2005) 26(6):649-658; Kontermann *Acta Pharmacologica Sincia* (2005) 26: 1-9; Ridgway et al., Prot Eng 9, 617-621 (1996); and Carter, J Immunol Meth 248, 7-15 (2001).

Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Immunoconjugates Comprising Detectable Labels

Provided are immunoconjugates comprising an anti-CD8 antibody described herein conjugated to a detectable label. The term "label" or "detectable label" refers to an atom, molecule, or compound that is useful in diagnosing, detecting or visualizing/imaging a location and/or quantity of a target molecule (such as CD8) on a cell, tissue, organ and the like. Detectable labels that can be used in accordance with the embodiments herein include, but are not limited to, radioactive substances (e.g., radioisotopes, radionuclides, radio labels or radiotracers), dyes (e.g., IndoCyanine Green (ICG)), contrast agents, fluorescent compounds or molecules, bioluminescent compounds or molecules, enzymes and enhancing agents (e.g., paramagnetic ions). In addition, some nanoparticles, for example quantum dots and metal nanoparticles can be suitable for use as a detection agent.

Radioactive substances that can be used as detectable labels in accordance with the embodiments herein include, but are not limited to $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{75}$Sc, $^{77}$As, $^{86}$Y, $^{89}$Sr, $^{89}$Zr, $^{90}$Y, $^{90}$Nb, $^{94}$Tc, $^{99}$mTc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, and $^{225}$Ac. Exemplary Paramagnetic ions substances that can be used as detectable labels include, but are not limited to ions of transition and lanthanide metals (e.g. metals having atomic numbers of 6 to 9, 21 to 29, 42 to 44, or 57 to 71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

When the detectable label is a radioactive metal or paramagnetic ion, in some embodiments, the label can be reacted with a reagent having a long tail with one or more chelating groups attached to the long tail for binding these ions. The long tail can be a polymer such as polylysine, polysaccharide, or other derivatized or derivatizable chains having pendant groups to which a chelating group (i.e., for binding ions) may be bound. Examples of chelating groups that may be used according to the embodiments herein include, but are not limited to, ethylenediaminetetraacetic acid (EDTA), diethylenetriaminepentaacetic acid (DTPA), DOTA, NOIA, NOGADA, NETA, NODA, NOTA, deferoxamine (DfO), DFO* (i.e., DFO-star), DFO-squaramide, porphyrins, polyamines, crown ethers, bis-thiosemicarbazones, polyoximes, and like groups. The chelate can be linked to an anti-CD8 antibody provided herein by a group that allows formation of a bond to the molecule with minimal loss of immunoreactivity and minimal aggregation and/or internal cross-linking. The same chelates, when complexed with non-radioactive metals (e.g., manganese, iron and gadolinium) are useful for magnetic resonance imaging (MRI), when used along with the anti-CD8 antibodies described herein. Macrocyclic chelates such as NOIA, NOGADA, DOTA, NODA, NOTA, and TETA are of use with a variety of metals and radiometals including, but not limited to, e.g., radionuclides of gallium, yttrium and copper. Other ring-type chelates such as macrocyclic polyethers, which are of interest for stably binding radionuclides, such as Radium-223 for radioactive iodine treatment (RAIT) may be used. In certain embodiments, chelating moieties may be used to attach a positron emission tomography (PET) imaging agent, such as an aluminum-$^{18}$F complex, to an anti-CD8 antibody provided herein for use in PET analysis.

Exemplary contrast agents that can be used as detectable labels in accordance with the embodiments of methods and compositions herein include, but are not limited to, barium, diatrizoate, ethiodized oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, thallous chloride, or combinations thereof.

Bioluminescent and fluorescent compounds or molecules and dyes that can be used as detectable labels in accordance with the methods and compositions herein include, but are not limited to, e.g., fluorescein, fluorescein isothiocyanate (FITC), OREGON GREEN™, rhodamine, Texas red, IRDye800CW, AlexaFluor 647, tetrarhodimine isothiocynate (TRITC), Cy3, Cy5, and the like), fluorescent markers (e.g., green fluorescent protein (GFP), phycoerythrin, and the like), autoquenched fluorescent compounds that are activated by tumor-associated proteases, enzymes (e.g., luciferase, horseradish peroxidase, alkaline phosphatase, and the like), nanoparticles, biotin, digoxigenin or combination thereof.

Enzymes that can be used as detectable labels in accordance with the methods and compositions herein include, but are not limited to, e.g., horseradish peroxidase, alkaline phosphatase, acid phosphatase, glucose oxidase, beta-galactosidase, beta-glucoronidase or beta-lactamase. Such enzymes may be used in combination with a chromogen, a fluorogenic compound or a luminogenic compound to generate a detectable signal.

In some embodiments, an anti-CD8 antibody provided herein is conjugated to a nanoparticle, i.e., a microscopic particle whose size is measured in nanometers. For example, a nanoparticle is a particle with at least one dimension less than about 100 nm. Nanoparticles can be used as detectable substances because they are small enough to scatter visible light rather than absorb it. For example, gold nanoparticles possess significant visible light extinction properties and appear deep red to black in solution. As a result, anti-CD8 antibodies provided herein that have been conjugated to nanoparticles can be used for the in vivo imaging of T-cells in a subject. At the small end of the size range, nanoparticles are often referred to as clusters. Metal, dielectric, and semiconductor nanoparticles have been formed, as well as hybrid structures (e.g. core-shell nanoparticles). Nanospheres, nanorods, and nanocups are just a few of the shapes that have been grown. Semiconductor quantum dots and nanocrystals are examples of additional types of nanoparticles. Such nanoscale particles, when conjugated to an anti-CD8 antibody provided herein, can be used as imaging agents for the in vivo detection of T-cells as described herein.

Conjugates of an antibody and a label may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionuclide to the antibody. See WO94/11026. The linker may be a “cleavable linker” facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used. The immunuoconjugates herein include, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A). In some embodiments, an anti-CD8 antibody provided herein comprises a linker that is a desferrioxamine compound (see, e.g., Vugts et al. (2017) *Eur J Nucl Med Mol Imaging.* 44:286-295 and Rudd et al. (2016) *Chem Commun.* 52: 11859-12000). In some embodiments, an anti-CD8 antibody provided herein comprises an N-succinyl-desferrioxamine (DFO) linker. In some embodiments, an anti-CD8 antibody provided herein is conjugated to a radionuclide (e.g., including, but not limited to $^{89}$Zr, $^{124}$I, or $^{18}$F) by way of a desferrioxamine compound (e.g., N-succinyl-desferrioxamine).

In certain embodiments, an anti-CD8 antibody provided herein is directly coupled to a detectable label (i.e., without a linker).

Methods of Producing anti-CD8 Antibodies

Anti-CD8 antibodies described herein may be produced using recombinant methods and compositions, e.g., as described in U.S. Pat. No. 4,816,567. In one embodiment, isolated nucleic acid encoding an anti-CD8 antibody described herein is provided. Such nucleic acid may encode an amino acid sequence comprising the VL and/or an amino acid sequence comprising the VH of the antibody (e.g., the light and/or heavy chains of the antibody). In certain embodiments, an isolated nucleic acid encoding an anti-CD8 heavy chain variable region is provided wherein the nucleic acid comprises a sequence having at least 90%, 91%, 92%, 93%, 94%, 95%, 96%, 97%, 98%, 99%, or 100% sequence identity to a nucleic acid sequence that encodes SEQ ID NO: 14, SEQ ID NO: 16, SEQ ID NO: 18, SEQ ID NO: 20, SEQ ID NO: 22, SEQ ID NO: 24, or SEQ ID NO: 26. In certain embodiments, an isolated nucleic acid encoding an anti-CD8 light chain variable region is provided wherein the nucleic acid comprises a sequence having at least 90%, 91%, 92%, 93%, 94%, 95%, 96%, 97%, 98%, 99%, or 100% sequence identity to a nucleic acid sequence that encodes SEQ ID NO: 15, SEQ ID NO: 17, SEQ ID NO: 19, SEQ ID NO: 21, SEQ ID NO: 23, SEQ ID NO: 25, or SEQ ID NO: 27.

In certain embodiments, an isolated nucleic acid encoding an anti-CD8 heavy chain variable region and an anti-CD8 light chain variable region is provided, wherein the nucleic acid encoding the heavy chain variable region comprises a sequence having at least 90%, 91%, 92%, 93%, 94%, 95%, 96%, 97%, 98%, 99%, or 100% sequence identity to a nucleic acid sequence that encodes SEQ ID NO: 14, SEQ ID NO: 16, SEQ ID NO: 18, SEQ ID NO: 20, SEQ ID NO: 22, SEQ ID NO: 24, or SEQ ID NO: 26 and the nucleic acid encoding the light chain variable region comprises a sequence having at least 90%, 91%, 92%, 93%, 94%, 95%, 96%, 97%, 98%, 99%, or 100% sequence identity to a nucleic acid sequence that encodes SEQ ID NO: 15, SEQ ID NO: 17, SEQ ID NO: 19, SEQ ID NO: 21, SEQ ID NO: 23, SEQ ID NO: 25, or SEQ ID NO: 27. In certain embodiments, an isolated nucleic acid encoding an anti-CD8 heavy chain variable region is provided wherein the nucleic acid comprises a sequence that encodes SEQ ID NO: 14, SEQ ID NO: 16, SEQ ID NO: 18, SEQ ID NO: 20, SEQ ID NO: 22, SEQ ID NO: 24, or SEQ ID NO: 26. In certain embodiments, an isolated nucleic acid encoding an anti-CD8 light chain variable region is provided wherein the nucleic acid comprises a sequence that encodes SEQ ID NO: 15, SEQ ID NO: 17, SEQ ID NO: 19, SEQ ID NO: 21, SEQ ID NO: 23, SEQ ID NO: 25, or SEQ ID NO: 27. In certain embodiments, an isolated nucleic acid encoding an anti-CD8 heavy chain variable region and light chain variable region is provided, wherein the nucleic acid encoding the heavy chain encodes SEQ ID NO: 14 and the nucleic acid encoding the light chain encodes SEQ ID NO:15. In certain embodiments, an isolated nucleic acid encoding an anti-CD8 heavy chain variable region and light chain variable region is provided, wherein the nucleic acid encoding the heavy chain encodes SEQ ID NO: 16 and the nucleic acid encoding the light chain encodes SEQ ID NO:17. In certain embodiments, an isolated nucleic acid encoding an anti-CD8 heavy chain variable region and light chain variable region is provided, wherein the nucleic acid encoding the heavy chain encodes SEQ ID NO: 18 and the nucleic acid encoding the light chain encodes SEQ ID NO:19. In certain embodiments, an isolated nucleic acid encoding an anti-CD8 heavy chain variable region and light chain variable region is provided, wherein the nucleic acid encoding the heavy chain encodes SEQ ID NO: 20 and the nucleic acid encoding the light chain encodes SEQ ID NO:21. In certain embodiments, an isolated nucleic acid encoding an anti-CD8 heavy chain variable region and light chain variable region is provided, wherein the nucleic acid encoding the heavy chain encodes SEQ ID NO: 22 and the nucleic acid encoding the light chain encodes SEQ ID NO:23. In certain embodiments, an isolated nucleic acid encoding an anti-CD8 heavy chain variable region and light chain variable region is provided, wherein the nucleic acid encoding the heavy chain encodes SEQ ID NO: 24 and the nucleic acid encoding the light chain encodes SEQ ID NO:25. In certain embodiments, an isolated nucleic acid encoding an anti-CD8 heavy chain variable region and light chain variable region is provided, wherein the nucleic acid encoding the heavy chain encodes SEQ ID NO: 26 and the nucleic acid encoding the light chain encodes SEQ ID NO:27.

In a further embodiment, one or more vectors (e.g., expression vectors) comprising nucleic acid(s) described herein are provided. In a further embodiment, a host cell comprising such nucleic acid(s) or vector(s) is provided. In one such embodiment, a host cell comprises (e.g., has been transformed with): (1) a vector comprising a nucleic acid that encodes an amino acid sequence comprising the VL of the anti-CD8 antibody and an amino acid sequence comprising the VH of the anti-CD8 antibody, or (2) a first vector comprising a nucleic acid that encodes an amino acid sequence comprising the VL of the anti-CD8 antibody and a second vector comprising a nucleic acid that encodes an amino acid sequence comprising the VH of the anti-CD8 antibody. In one embodiment, the host cell is eukaryotic, e.g. a Chinese Hamster Ovary (CHO) cell or lymphoid cell (e.g., Y0, NS0, Sp20 cell). In one embodiment, the host cell is prokaryotic, e.g. an *E. coli* cell. In one embodiment, a method of making an anti-CD8 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CD8 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology, Vol.* 248 (B.K.C. Lo, ed., Humana Press, Totowa, NJ, 2003), pp. 245-254, describing expression of antibody fragments in *E. coli*). After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B.K.C. Lo, ed., Humana Press, Totowa, NJ), pp. 255-268 (2003).

Methods of Detecting, Localizing, and/or Imaging CD8$^+$ Cells using anti-CD8 Antibodies Provided herein are methods of detecting, localizing, and/or imaging CD8$^+$ cells using an anti-CD8 antibody, or an immunoconjugate comprising an anti-CD8 antibody and a detectable label herein. In some embodiments, the method comprises detecting the presence of CD8 in an in vitro or ex vivo sample. In some embodiments, the method comprises adding the anti-CD8 antibody or the immunoconjugate to an in vitro or ex vivo sample. Such method, which includes, but is not limited to, e.g., Western blots, immunohistochemical analyses, ELISA assays, and the like, optionally comprises performing a wash following the addition of the anti-CD8 antibody or immunoconjugate to the in vitro or ex vivo sample. In some embodiments, detecting the binding of the anti-CD8 antibody to CD8 comprises detecting the label attached to the immunoconjugate. In some embodiments, the method comprises applying a secondary agent that comprises a detectable label herein that binds to an anti-CD8:CD8 complex, and detecting the binding of the anti-CD8 antibody to CD8 comprises detecting the detectable label of the secondary agent. It will be readily understood by those of ordinary skill in the art that the secondary agent does not compete with the anti-CD8 antibody for binding to CD8, or compete with CD8 for binding to the anti-CD8 antibody.

In some embodiments, the method comprises detecting, localizing, or imaging the presence of CD8 in vivo. In some embodiments, the method comprises administering the anti-CD8 antibody or an immunoconjugate described herein to a subject. In some embodiments, the subject is a human. In some embodiments, the subject is a non-human mammal, e.g., a rat, mouse, guinea pig, hamster, rabbit, dog, cat, cow, horse, goat, sheep, donkey, pig, monkey, ape, or other non-human primate. In some embodiments, the non-human primate is a rhesus macaque or a cynomolgous macaque. In some embodiments, the anti-CD8 antibody or immunoconjugate is administered orally, topically, or locally to the subject. In some embodiments, the anti-CD8 antibody or immunoconjugate is administered the subject via infusion (such as an intravenous infusion). In some embodiments, the infusion is intraperitoneal. In some embodiments, the method comprises administering the anti-CD8 antibody or immunoconjugate to the subject and removing a sample from the subject for analysis (i.e., detection of the binding of the anti-CD8 antibody or immunoconjugate to CD8).

In some embodiments, the detection, localization and/or imaging of $CD8^+$ cells is performed in vivo, e.g., using techniques described in further detail elsewhere herein.

In some embodiments, detecting the presence of CD8 in vivo comprises localizing CD8 (such as $CD8^+$ cells) to an organ or a tissue. In some embodiments, the method comprises determining the number of $CD8^+$ cells in an organ or tissue in a subject. In certain embodiments, the subject has cancer, and detecting the presence of CD8 in vivo comprises localizing $CD8^+$ cells to a tumor. In some embodiments, the $CD8^+$ cells are $CD8^+$ T cells, e.g., tumor infiltrating $CD8^+$ T cells. In some embodiments, the method comprises determining the number of $CD8^+$ T cells in a tumor in a subject who has cancer. In some embodiments, the method comprises determining the number of $CD8^+$ T cells in a tumor in a subject who has cancer at multiple successive time points.

Techniques for In Vivo Detection of CCS

In some embodiments, the binding of the anti-CD8 antibody to CD8 (such as a $CD8^+$ cell, e.g., a $CD8^+$ T cell) in vivo is detected via at least one of: immuno PET (positron emission tomography), SPECT (single-photon emission computed tomography), MRI (magnetic resonance imaging), which is also known as NMR (nuclear magnetic resonance), near-infrared (NIR), or Cerenkov luminescence imaging (CLI). In some embodiments, the binding of the anti-CD8 antibody to CD8 is detected via two or more forms of imaging. In some embodiments, the binding of the anti-CD8 antibody to CD8 is detected via near-infrared (NIR) and/or CLI. In some embodiments, the binding of the anti-CD8 antibody to CD8 is detected via immunoSPECT and/or NIR fluorescence. In some embodiments, the binding of the anti-CD8 antibody to CD8 is detected via immunoSPECT and computer tomography.

Immuno-PET is based on the coincidental detection of an antibody (such as an anti-CD8 antibody provided herein) or fragment thereof labeled with a positron-emitting radionuclide. Such radionuclides include, but are not limited to, e.g., $^{18}F$, $^{64}Cu$, $^{76}Br$, $^{86}Y$, $^{88}Y$, $^{89}Zr$, $^{99m}Tc$, $^{111}In$, $^{177}Lu$, $^{123}I$, $^{124}I$, $^{125}I$, and $^{131}I$. The emitted positron will travel a distance of a few millimeters, depending on the initial positron energy and the density of the surroundings (see, e.g., Table 2 in Guus et al. (2007) *The Oncologist,* 12: 1379-1389). After having lost its kinetic energy, the positron combines with an electron, leading to the so-called annihilation process, which yields two photons, each with an energy of 511 keV. The two photons are emitted simultaneously in opposite directions. The distribution of a positron-emitting radionuclide-labeled anti-CD8 antibody in a patient can be monitored by detection of the annihilation photon pairs with a PET camera. A PET camera consists of a ring of detectors placed around the body of the patient. If two photons are registered by detectors on opposite sides of the body within a very short time interval (typically 5-15 nanoseconds), it is assumed that somewhere along the line between the two detectors an annihilation event has taken place. By calculating the crossing of all lines, the location of the radiation source (radiolabeled mAb) can be determined. For quantification, PET can provide reliable information when appropriate corrections are performed (see Verel et al. (2005) J Nucl Med, 46 suppl 1:164S-171S). Additional details regarding immuno PET are provided in, e.g., van Dongen et al. (2007) The Oncologist, 12(12): 1379-1389; Reddy et al. (2010) Semin Nucl Med. 40(3): 182-189; Boerman et al. (2011) J. Nucl Med. 52(8): 1171-1172; Santangelo et al. (2015) Nature Methods, 12: 427-432.

immunoSPECT imaging entails the administration of a an antibody (such as an anti-CD antibody provided herein) or fragment thereof labeled with a gamma-emitting radionuclide to a subject, typically through injection into the bloodstream. Examples of gamma-emitting radionuclides include, but are not limited to, e.g., $^{99m}Tc$, $^{111}In$, $^{123}I$, $^{131}I$, $^{153}Sm$, or $^{186}Re$. Next, a gamma camera is used to acquire multiple 2-D images, from multiple angles. A computer is then used to apply a tomographic reconstruction algorithm to the multiple projections, yielding a 3-D data set. This data set may then be manipulated to show thin slices along any chosen axis of the body, similar to those obtained from other tomographic techniques. To acquire SPECT images, the gamma camera is rotated around the patient. Projections are acquired at defined points during the rotation, typically every 3-6 degrees. In most cases, a full 360-degree rotation is used to obtain an optimal reconstruction. The time taken to obtain each projection is also variable, but 15-20 seconds is typical. This gives a total scan time of 15-20 minutes. In some cases a SPECT gamma scanner may be built to operate with a conventional CT scanner, with coregistration of images. This allows location of tumors or tissues which may be seen on SPECT scintigraphy, but are difficult to locate precisely with regard to other anatomical structures. Additional details regarding immunoSPECT can be found in, e.g., Laverman et al. (2015) *J Nucl Med,* 56(5): 778-783; Lutje et al. (2014) *Cancer Res,* 74(21): 6216-6223; Muselaers et al. (2013) *Eur Urology* 64(4): 1101-1106; and others.

The principle of in vivo MRI (magnetic resonance imaging), also known as NMR (nuclear magnetic resonance), is based on manipulating the magnetic properties of the protons and neutrons contained in atomic nuclei present a subject's body (most commonly, those found in the atoms of hydrogen). The motion of these nuclei produces a small magnetic moment. When the subject's body is placed in the magnetic field of the MRI scanner, the magnetic moment of these nuclei aligns with the direction of the magnetic field. A radiofrequency (RF) pulse is then applied to the subject's body in the scanner, which excites the nuclei such that there are transitions between lower and higher energy spin states. Once the RF pulse is given, the nuclei return to their equilibrium state (a process called relaxation), releasing their absorbed extra energy and emitting an RF signal. This signal is detected by the scanner's RF coils and is then used to generate a detailed image of the body's tissues. By using MRI contrast agents, the contrast of this image, and so the visibility of specific body structures, can be improved. Examples of labels that are detectable via MRI include, but are not limited to, e.g., superparamagnetic iron oxides (including iron oxide nanoparticles such as Molday ION Rhodamine-B Carboxyl), $^{19}F$-based probes, paramagnetic metals (e.g., gadolinium, manganese, manganese oxide, dysprosium), (U)SPIO, PARA(CEST), DIA(CEST), and PFCs. Additional information about using labeled antibodies for in vivo MRI and/or labels that are detectable via MRI is discussed in, e.g., Srivastava (2015) *Dis Model Mech.* 8(4): 323-336; Zhou et al. (2013) *Wiley Interdiscip Rev Nanomed Nanobiotechnol.* 5(1): 1-18; Sohn et al. (2015) *Nanomedicine.* 11(1): 127-135; Bates et al. (2014) *PloS ONE* 9(5): e97220; Zhu et al. (2015) *Int. J. Mol. Sci.* 16: 9573-9587; and Zhang et al. (2014) Int J. Medicine. 9: 33-41.

NIR imaging takes advantage of the deep photon penetration of near infrared light into living tissue to provide imaging of endogenous and/or exogenous contrast at depths of <1 cm. Within this field, NIR fluorescence imaging focuses on the detection of an antibody labeled with an exogenous contrast agent that emits fluorescence between 700 and 900 nm. The typical fluorescence imaging system has been described in detail elsewhere (De Grand et al. (2003) *Technol Cancer Res Treat,* 2:553-62; Nakayama et al. (2002)*Mol Imaging,* 1:365-77; Ntziachristos et al. (2003) *Eur Radiol,* 13:195-208; Tanaka et al. (2006) *Ann Surg Oncol,* 13:1671-81; Themelis et al. (2009) *J Biomed Opt,* 4:064012; and Troyan et al. (2009) *Ann Surg Oncol,* 16:2943-52. Briefly, it consists of a spectrally resolved light source (filtered broadband source, light-emitting diode [LED], or laser diode) exciting a fluorophore within a turbid medium. The light emitted from this fluorophore is then imaged onto a charge-coupled device (CCD) camera, with special care taken to filter out the powerful excitation light. Examples of infrared dyes include, but are not limited to, Tracy 652, Tracy 645, rhodamine dyes, cyanine dyes, Cy7, Cy7.5, Alexa Fluor®, CyDye®, IRDye®, DyLight, and ATTO. Cellular and tissue imaging in the near-infrared (NIR) wavelengths between about 650 and about 950 nm is advantageous for in vivo imaging because of the low absorption of biological molecules in this region. Further details regarding the use of labeled antibodies for NIR imaging in vivo and detectable labels for NIR imaging in vivo are provided in Cillers et al. (2017) *Mol Pharmaceuticals* 14(5): 1623-1633; Hilderbrand et al. (2010) *Curr Opin Chem Biol.* 14(1): 71-79; Hong et al. (2017) *Nat Biomed Eng.* 1, 0010 DOI: 10.1038/s41551-016-0010; Pansare et al. (2012) *Chem Mater.* 24(5): 812-827; Hickson (2009) *Urol Oncol Semin Orig Invest.* 27: 295-297; Zhang et al. (2012) *Curr Protoc Cytom.* Chapter 12: Unit 12.7; Quek et al. (2012) *Nanomaterials.* 2: 92-112; Luker et al. (2008) J Nucl Med 49:1-4; and Liu et al. (2016) *NPG Asia Materials.* 8, e295.

Cerenkov luminescence imaging (CLI) is a molecular optical imaging technique that is based on the detection of optical Cerenkov photons emitted by positron emission tomography (PET) imaging agents (such as those described elsewhere herein). Other CLI imaging agents include, but are not limited to, e.g., $^{131}$I, $^{18}$F, and $^{90}$Y. Cerenkov radiation is produced when a charged particle travels through a dielectric medium (i.e., a medium that can be polarized by an electric field) with a speed faster than the speed of light in that medium. While propagating, the charged particle (a positively charged positron or negatively charged electron) induces a local polarization by displacing the positive and negative charges of the atoms in the medium. See, e.g., FIG. 1 in Grootendorst et al. (2016) *Clin Transl Imaging.* 4(5): 353-366). When the particle's speed exceeds the speed of light, the polarization becomes asymmetrical along the track of the particle, resulting in a dipole electric field at larger distances from the particle. As the particle passes, the electrons of the atoms return to their ground state, thereby emitting the transferred energy as optical photons. CLI images can be acquired by detecting the Cerenkov light from PET tracers using ultra-high-sensitivity optical cameras such as electron-multiplying charge-coupled device (EMCCD) cameras. The CLI image can be analyzed semi-quantitatively in photon radiance. CLI and PET are directly correlated due to both techniques measuring the photons produced by positron-emitting radiopharmaceuticals; PET measures the annihilation photons, and CLI measures the Cerenkov photons. Several studies have shown a strong correlation between CLI and PET for different radiopharmaceuticals in vitro, ex vivo and in vivo, thus demonstrating the feasibility of CLI for molecular imaging of living subjects. Publications regarding CLI or which detail the correlation between CLI and PET include, e.g., Xu et al. (2012) *J Nucl Med,* 53(2):312-317; Liu et al. (2010) *PLoS ONE.* 5(3):e9470; Zhang et al. (2013) *PLoS ONE.* 8(4): e62007; Hu et al. (2015) *Eur Radiol.* 25(6):1814-1822; Robertson et al. (2011) J Nucl Med. 52(11):1764-1769; Timmermand et al. (2015) *J Nucl Med.* 56(3):444-449; Cao et al. (2014) *Biomed Opt Express.* 5(10):3660-3670 and Thorek et al. (2014) *J Nucl Med.* 55(1):95-98.

Methods of Predicting the Responsiveness of a Subject Having Cancer to Treatment with an Immunotherapentic Agent Also provided are methods of predicting the responsiveness of a subject having cancer to treatment with an immunotherapeutic agent. In some embodiments, the method comprises administering a labeled anti-CD8 antibody (e.g., an immunoconjugate comprising a detectable label described elsewhere herein) and detecting the binding of the labeled anti-CD8 antibody to $CD8^+$ T cells in a tumor tissue in the subject, wherein the detection of the binding indicates that the subject is likely to respond to the immunotherapy. In some embodiments, the anti-CD8 antibody is labeled with a detectable label (e.g., $^{89}$Zr, $^{124}$I, $^{18}$F, etc.), and the binding of the labeled anti-CD8 antibody to $CD8^+$ T cells in a tumor tissue is detected via PET or PET/CT. In some embodiments, the anti-CD8 antibody is a monovalent antibody. In some embodiments, the monovalent anti-CD8 antibody is a one armed antibody. In some embodiments, the one armed anti-CD8 antibody comprises a full length heavy chain comprising (such as consisting of) the amino acid sequence set forth in SEQ ID NO: 28, a light chain comprising (such as consisting of) the amino acid sequence set forth in SEQ ID NO: 29, and an Fc comprising (such as consisting of) the amino acid sequence set forth in SEQ ID NO: 30.

In some embodiments, the method comprises administering a therapeutically effective amount of an immunotherapeutic agent or a cancer vaccine (e.g., a Personalized Cancer Vaccine or "PCV") to the subject in whom the binding of the labeled anti-CD8 antibody to $CD8^+$ T cells in a tumor tissue has been detected.

In certain embodiments, the immunotherapeutic agent is an immune checkpoint inhibitor. In some embodiments, the immune checkpoint inhibitor is a therapeutic anti-CTLA-4 antibody, such as ipilimumab (Yervoy®). In some embodiments, the immune checkpoint inhibitor is a therapeutic anti-PD-1 antibody. In certain embodiments, the therapeutic anti-PD-1 antibody is nivolumab (Opdivo®). In certain embodiments, the therapeutic anti-PD-1 antibody is pembrolizumab (Keytruda®). In certain embodiments, the therapeutic anti-PD-1 antibody is pidlizumab.

In some embodiments, the immune checkpoint inhibitor is a therapeutic anti-PD-L1 antibody. In certain embodiments, the therapeutic anti-PD-L1 antibody is BMS-936559. In certain embodiments, the therapeutic anti-PD-L1 antibody is avelumab (Banvencio®). In certain embodiments, the therapeutic anti-PD-L1 antibody is durvalumab (Imfinzi®). In some embodiments, the therapeutic anti-PD-L1 antibody is atezolizumab (Tecentriq®).

Further details regarding therapeutic immune checkpoint inhibitors are provided in, e.g., Byun et al. (2017) *Nat Rev Endocrinol.* 13: 195-207; La-Beck et al. (2015) *Pharmacotherapy.* 35(10): 963-976; Buchbinder et al. (2016) *Am J Clin Oncol.* 39(1): 98-106; Michot et al. (2016) *Eur J Cancer.* 54: 139-148, and Topalian et al. (2016) *Nat Rev Cancer.* 16: 275-287.

In some embodiments, the immune checkpoint inhibitor is administered to the subject in combination with one or more additional therapeutic (such as chemotherapeutic) agents. In some embodiments, the immune checkpoint inhibitor that is administered to the subject in combination with one or more additional therapeutic (such as chemotherapeutic) agents is an anti-PD-L1 antibody (such as atezolizumab). Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chlorambucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length $IgG_1\lambda$ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see U.S. Pat. No. 4,943,533, Mendelsohn et al.) and variants thereof, such as chimerized 225 (C225 or Cetuximab; ERBUTIX®) and reshaped human 225 (H225) (see WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP659439A2, Merck Patent GmbH). EGFR antagonists include small molecules such as compounds described in U.S. Pat. Nos. 5,616,582; 5,457,105; 5,475,001; 5,654,307; 5,679,683; 6,084,095; 6,265,410; 6,455,534; 6,521,620; 6,596,726; 6,713,484; 5,770,599; 6,140,332; 5,866,572; 6,399,602; 6,344,459; 6,602,863; 6,391,874; 6,344,455; 5,760,041; 6,002,008; and 5,747,498; as well as the following PCT publications: WO 98/14451, WO 98/50038, WO 99/09016, and WO 99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyflpropoxy]-6-quinazolinyl]-, dihydrochloride, Pfizer Inc.); ZD1839, gefitinib (IRES SAO) 4-(3'-Chloro-4'-fluoroanilino)-7-methoxy-6-(3-morpholinopropoxy)quinazoline, Astra7eneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PM-166 ((R)-4-[4-[(1-phenylethyflamino]-1H-pyrrolo[2,3-d]pyrimidin-6-yl]-phenol); (R)-6-(4-hydroxyphenyl)-4-[(1-phenylethyflamino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl)ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from GlaxoSmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVECO, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lambert); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521;

Isis/Lilly); imatinib mesylate (GLEEVEC®); PM 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNF$\alpha$) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/$\beta$2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-$OCH_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib.

In some embodiments, the anti-PD-L1 antibody (such as atezolizumab) is administered in combination with one or more of the following chemotherapeutic agents: an anti-HER2 antibody (e.g., trastuzumab (HERCEPTIN®, Genentech) or pertuzumab (PERJETA®, Genentech)), a PD1 binding antagonist (e.g., MDX-1106 (nivolumab), MK-3475 (pembrolizumab, lambrolizumab), CT-011 (pidilizumab), or AMP-224), and a PD-L2 binding antagonist.

In some embodiments, the anti-PD-L1 antibody (such as atezolizumab) is administered in combination with a growth inhibitory agent. A "growth inhibitory agent" when used herein refers to a compound or composition which inhibits growth of a cell either in vitro or in vivo. Exemplary growth inhibitory agents include, e.g., vincas (vincristine and vinblastine), taxanes (Docetaxel (TAXOTERE®, Rhone-Poulenc Rorer) and paclitaxel (TAXOL®, Bristol-Myers Squibb)) and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13.

In some embodiments, the immunotherapeutic agent is a dendritic cell activator or dendritic cell growth factor. In some embodiments, the immunotherapeutic agent is a vaccine adjuvant. In some embodiments, the immunotherapeutic agent is a T-cell stimulator or growth factor. In some embodiments, the immunotherapeutic agent is an agent that neutralizes or inhibits suppressive immune cells, cytokines, and/or enzymes.

In some embodiments, the method comprises administering a immunotherapeutic agent selected from the group consisting of an anti-TIGIT antibody, a TIGIT antagonist, an anti-CSF-1R antibody, an anti-CSF-1R antagonist, an anti-CEA antibody, an anti-CEA antagonist, an anti-CTLA4 antibody, a CTLA4 antagonist, an anti-0X40 antibody, an 0X40 agonist, any anti-PDL1 antibody combined with one or more chemotherapeutic agent, any anti-PD1 antibody combined with one or more chemotherapeutic agent, and atezolizumab combined with one or more chemotherapeutic agents. In some embodiments, the anti-PD1 or anti-PDL1 antibody is combined with one or more of Tarceva® (erlotinib), Zelboraf® (vemurafenib), Gazyva® (obinutuzumab), Avastin® (bevacizumab), Cotellic® (cobimetinib), Zelboraf® and Cotellic®, Alecensa® (alectinib), Kadcyla® (ado-trastuzumab emtansine), Herceptin® (trastuzumab), Perjeta® (pertuzumab), polatuzumab, INF-alpha, an anti-CD40 agent, an anti-OX40 antibody (e.g., an OX40 agonist), an anti-CSF-1R antibody, an anti-CEA antibody, an IDO inhibitor, or an anti-TIGIT antibody. In some embodiments, the anti-PD-L1 antibody is atezolizumab and the atezolizumab is combined with one or more of Tarceva® (erlotinib), Zelboraf® (vemurafenib), Gazyva® (obinutuzumab), Avastin® (bevacizumab), Cotellic® (cobimetinib), Zelboraf® and Cotellic®, Alecensa® (alectinib), Kadcyla® (ado-trastuzumab emtansine), Herceptin® (trastuzumab), Perjeta® (pertuzumab), polatuzumab, INF-alpha, an anti-CD40 agent, an anti-OX40 antibody (e.g., an OX40 agonist), an anti-CSF-1R antibody, an anti-CEA antibody, an IDO inhibitor, an anti-CTLA4 antibody, or an anti-TIGIT antibody.

Methods of Monitoring Disease Progression

Provided herein are methods of monitoring disease progression in a subject having cancer. Such methods comprise administering a labeled anti-CD8 antibody to the subject and detecting binding of the labeled anti-CD8 antibody to $CD8^+$ T cells in the tumor tissue in the subject at a first time point and second time point. In some embodiments, the methods further comprise administering a therapeutically effective amount of an immunotherapeutic agent (e.g., an immunotherapeutic agent described elsewhere herein) to the subject wherein the disease has progressed in the subject. In some embodiments, the methods comprise (a) administering a labeled anti-CD8 antibody to the subject and detecting binding of the labeled anti-CD8 antibody to $CD8^+$ T cells in the tumor tissue prior to administering the immunotherapeutic agent, (b) administering the immunotherapeutic agent, (c) administering the labeled anti-CD8 antibody to the subject and detecting binding of the labeled anti-CD8 antibody to $CD8^+$ T cells in the tumor tissue at a time point following the administration of the immunotherapeutic agent, and (d) measuring the difference in labelling of $CD8^+$ T cells in the tumor tissue before and after administration of the immunotherapeutic agent.

In certain embodiments, the immunotherapeutic agent is an immune checkpoint inhibitor. In certain embodiments, the immune checkpoint inhibitor is an anti-PD1 antibody (such as, but no limited to, an anti-PD1 antibody described herein). In certain embodiments, the immune checkpoint inhibitor is an anti-PD-L1 antibody (such as, but not limited to, an anti-PD-L1 antibody described herein). In certain embodiments, the anti-PD-L1 antibody is atezolizumab. In some embodiments, the anti-PD-L1 antibody (such as atezolizumab) is administered to the subject in combination with a second therapeutic agent (such as, but not limited to, an immunotherapeutic and/or chemotherapeutic agent described elsewhere herein.) In some embodiments, the second therapeutic agent is an immunotherapeutic agent. In some embodiments, the immunotherapeutic agent is an anti-PD-L1 antibody or an anti-PD1 antibody which is further combined with one or more of an anti-TIGIT antibody, a TIGIT antagonist, an anti-CSF-1R antibody, an anti-CSF-1R antagonist, an anti-CEA antibody, an anti-CEA antagonist, an anti-OX40 antibody, an OX40 agonist, an anti-CTLA4 antibody, a CTLA4 antagonist, Tarceva® (erlotinib), Zelboraf® (vemurafenib), Gazyva® (obinutuzumab), Avastin® (bevacizumab), Cotellic® (cobimetinib), Zelboraf® and Cotellic®, Alecensa® (alectinib), Kadcyla® (ado-trastuzumab emtansine), Herceptin® (trastuzumab), Perjeta® (pertuzumab), polatuzumab, INF-alpha, an anti-CD40 agent, or an IDO inhibitor.

In some embodiments, disease progression is detected when the level of $CD8^+$ T cells in the tumor tissue at the second time point is higher than the a level of $CD8^+$ T cells in the tumor tissue at the first time point. In certain embodiments, the level of $CD8^+$ T cells in the tumor tissue is detected in third, fourth, or fifth subsequent time points. In some embodiments, the time points are at least any one of 1 day, 3 days, 1 week, two weeks, three weeks, four weeks, one month, two months, three months, four months, five months, 6 months, 9 months, 12 months, 1.5 years, 2 years, 2.5 years, 3 years or more than three years apart. In some embodiments, the level of CD8+T cells in the tumor tissue is detected following the administration of the immunotherapeutic agent to the patient.

In some embodiments, the anti-CD8 antibody is labeled with a detectable label (e.g., $^{89}Zr$, $^{124}I$, $^{18}F$, or another detectable label described elsewhere herein) and the level of $CD8^+$ T cells in the tumor tissue in is detected via PET or PET/CT. In some embodiments, the anti-CD8 antibody is a monovalent antibody. In some embodiments, the monovalent anti-CD8 antibody is a one armed antibody. In some embodiments, the one armed anti-CD8 antibody comprises a full length heavy chain comprising (such as consisting of) the amino acid sequence set forth in SEQ ID NO: 28, a light chain comprising (such as consisting of) the amino acid sequence set forth in SEQ ID NO: 29, and an Fc comprising (such as consisting of) the amino acid sequence set forth in SEQ ID NO: 30.

Methods of Monitoring Treatment Progress

Provided herein are methods of monitoring treatment progress in a subject having cancer who has previously received or is currently receiving treatment with an immunotherapeutic agent (e.g., an immunotherapeutic agent described elsewhere herein.) Such methods comprise administering a labeled anti-CD8 antibody to the subject in conjunction with the immunotherapeutic agent, and detecting binding of the labeled anti-CD8 antibody to $CD8^+$ T cells in the tumor tissue at a first time point and a second time point. In some embodiments, the labeled anti-CD8 antibody is administered before the immunotherapeutic agent, and the first time point is after the administration of the labeled anti-CD8 antibody and prior to the administration of the immunotherapeutic agent, and the second time point is after the administration of the immunotherapeutic agent. In some embodiments, lower levels of $CD8^+$ T cells in the tumor tissue at the second time point as compared to the first time point indicates positive treatment progress (e.g., beneficial or desired clinical results). In some embodiments, higher levels of $CD8^+$ T cells in the tumor tissue at the second time point as compared to the first time point indicates lack of treatment progress (e.g., lack beneficial or desired clinical results). In some embodiments, the immunotherapeutic agent is administered before the labeled anti-CD8 antibody, the first time point is after the administration of the immunotherapeutic agent and after the administration of the labeled anti-CD8 antibody, and the second time point is after the first time point. In some embodiments, lower levels of $CD8^+$ T cells in the tumor tissue at the second time point as compared to the first time point indicates positive treatment progress (e.g., beneficial or desired clinical results). In some embodiments, higher levels of $CD8^+$ T cells in the tumor tissue at the second time point as compared to the first time point indicates lack of treatment progress (e.g., lack beneficial or desired clinical results). In certain embodiments, the level of $CD8^+$ T cells in the tumor tissue is detected in third, fourth, or fifth subsequent time points. In some embodiments, the time points are at least any one of 1 day, 3 days, 1 week, two weeks, three weeks, four weeks, one month, two months, three months, four months, five months, 6 months, 9 months 12 months, 1.5 years, 2, years, 2.5 years, 3 years or more than three years apart.

In certain embodiments, the immunotherapeutic agent is an immune checkpoint inhibitor. In certain embodiments, the immune checkpoint inhibitor is an anti-PD-L1 antibody (e.g., as described elsewhere herein). In certain embodiments, the anti-PD-L1 antibody is atezolizumab. In some embodiments, the anti-PD-L1 antibody (such as atezolizumab) is administered to the subject in combination with a second therapeutic agent (e.g., as described elsewhere herein.)

In some embodiments, the anti-CD8 antibody is labeled with a detectable label described herein (e.g., $^{89}Zr$, $^{124}I$, $^{18}F$, etc.) and the level of $CD8^+$ T cells in the tumor tissue is detected via PET or PET/CT. In some embodiments, the anti-CD8 antibody is a monovalent antibody. In some embodiments, the monovalent anti-CD8 antibody is a one armed antibody. In some embodiments, the one armed anti-CD8 antibody comprises a full length heavy chain comprising (such as consisting of) the amino acid sequence set forth in SEQ ID NO: 28, a light chain comprising (such as consisting of) the amino acid sequence set forth in SEQ ID NO: 29, and an Fc comprising (such as consisting of) the amino acid sequence set forth in SEQ ID NO: 30.

Methods of Predicting the Responsiveness of a Subject Having Cancer to Treatment with a Cancer Vaccine and Methods of Monitoring Disease Progression in a Subject Having Cancer to Whom a Cancer Vaccine Has Been Administered Provided herein are methods of predicting the responsiveness of a subject having cancer to treatment with a cancer vaccine. In some embodiments, the cancer vaccine is a Personalized Cancer Vaccine ("PCV"). Exemplary PCV are described in, e.g., Ott et al. (2017) *Nature* 547, 217-221 and Sahin et al. (2017) *Nature* 547, 222-226. In some embodiments, the method comprises administering a labeled anti-CD8 antibody (e.g., an immunoconjugate comprising an anti-CD8 antibody described herein and a detectable label described herein) and detecting the binding of the labeled anti-CD8 antibody to $CD8^+$ T cells in a tumor tissue in the subject, wherein the detection of the binding indicates that the subject is likely to respond to the immunotherapy. In some embodiments, the anti-CD8 antibody is labeled with, e.g., $^{89}Zr$, $^{124}I$, $^{18}F$, or another detectable label, and the binding of the labeled anti-CD8 antibody to CD8+ T cells in a tumor tissue is detected via PET or PET/CT. In some embodiments, the anti-CD8 antibody is a monovalent antibody. In some embodiments, the monovalent anti-CD8 antibody is a one armed antibody. In some embodiments, the one armed anti-CD8 antibody comprises a full length heavy chain comprising (such as consisting of) the amino acid sequence set forth in SEQ ID NO: 28, a light chain comprising (such as consisting of) the amino acid sequence set forth in SEQ ID NO: 29, and an Fc comprising (such as consisting of) the amino acid sequence set forth in SEQ ID NO: 30. In some embodiments, the cancer vaccine is administered in combination with one or more immunotherapeutic and/or chemotherapeutic agents described herein.

Also provided herein are methods of monitoring disease progression in a subject having cancer. Such methods comprise administering an anti-CD8 antibody (such as an anti-CD8 antibody that has been labeled with a detectable label described elsewhere herein) to the subject and detecting binding of the labeled anti-CD8 antibody to $CD8^+$ T cells in the tumor tissue in the subject at a first time point and second time point. In some embodiments, the methods further comprise administering a therapeutically effective amount of a cancer vaccine. In some embodiments the cancer vaccine is a Personalized Cancer Vaccine ("PCV").

Provided herein are methods of monitoring treatment progress in a subject having cancer who has previously received or is currently receiving treatment with cancer vaccine. In certain embodiments, the cancer vaccine is a Personalized Cancer Vaccine ("PCV"). In some embodiments, the methods comprise (a) administering a labeled anti-CD8 antibody to the subject and detecting binding of the labeled anti-CD8 antibody to CD8+T cells in the tumor tissue prior to administering the cancer vaccine (e.g., PCV), (b) administering the cancer vaccine (e.g., PCV), (c) administering the labeled anti-CD8 antibody to the subject and detecting binding of the labeled anti-CD8 antibody to $CD8^+$ T cells in the tumor tissue at a time point following the administration of the cancer vaccine (e.g., PCV), and (d) measuring the difference in labelling of $CD8^+$ T cells in the tumor tissue before and after administration of the cancer vaccine (e.g., PCV).

In some embodiments, the anti-CD8 antibody is labeled with, e.g., $^{89}Zr$, $^{124}I$, $^{18}F$, or another detectable label described herein, and the level of $CD8^+$ T cells in the tumor tissue is detected via PET or PET/CT. In some embodiments, the anti-CD8 antibody is a monovalent antibody. In some embodiments, the monovalent anti-CD8 antibody is a one armed antibody. In some embodiments, the one armed anti-CD8 antibody comprises a full length heavy chain comprising (such as consisting of) the amino acid sequence set forth in SEQ ID NO: 28, a light chain comprising (such as consisting of) the amino acid sequence set forth in SEQ ID NO: 29, and an Fc comprising (such as consisting of) the amino acid sequence set forth in SEQ ID NO: 30.

Methods of Monitoring Autoimmune Diseases, Transplant Rejection, and Graft-Versus-Host Disease Provided herein are methods of monitoring treatment progress and disease progression in a subject having an autoimmune disease (e.g., autoimmune arthritis), transplant rejection, or graft-versus-host disease. Such diseases all involve $CD8^+$ T cells as part of the damaging inflammatory process. See Petrelli & Femke, *$CD8^+$ T cells in human autoimmune arthritis: the usual suspects; Nature Reviews Thumatology* 12:421-428 (2016). Such methods comprise administering a labeled anti-CD8 antibody to the subject, with or without interventional treatment, and detecting binding of the labeled anti-CD8 antibody to $CD8^+$ T cells in the tissue at a first time point and a second time point. In some embodiments, an increase in $CD8^+$ T cells from the first time point and the second time point is an indication that the autoimmune disease, transplant rejection, or graft-versus-host disease has progressed. In some embodiments, an interventional therapy to treat the autoimmune disease, transplant rejection, or graft-versus-host disease is administered before the labeled anti-CD8 antibody, the first time point is after the administration of the interventional therapy to treat the autoimmune disease, transplant rejection, or graft-versus-host disease and after the administration of the labeled anti-CD8 antibody, and the second time point is after the first time point. In some embodiments, lower levels of $CD8^+$ T cells in the tissue at the second time point as compared to the first time point indicates positive treatment progress (e.g., beneficial or desired clinical results). In some embodiments, higher levels of $CD8^+$ T cells in the tissue at the second time point as compared to the first time point indicates lack of treatment progress (e.g., lack beneficial or desired clinical results). In certain embodiments, the level of $CD8^+$ T cells in the tissue is detected in third, fourth, or fifth subsequent time points. In some embodiments, the time points are at least any one of 1 day, 3 days, 1 week, two weeks, three weeks, four weeks, one month, two months, three months, four months, five months, 6 months, 9 months 12 months, 1.5 years, 2, years, 2.5 years, 3 years or more than three years apart.

In some embodiments, the anti-CD8 antibody is labeled with a detectable label described herein (e.g., $^{89}Zr$, $^{124}I$, $^{18}F$, etc.) and the level of $CD8^+$ T cells in the tissue is detected via PET or PET/CT. In some embodiments, the anti-CD8 antibody is a monovalent antibody. In some embodiments, the monovalent anti-CD8 antibody is a one armed antibody. In some embodiments, the one armed anti-CD8 antibody comprises a full length heavy chain comprising (such as consisting of) the amino acid sequence set forth in SEQ ID NO: 28, a light chain comprising (such as consisting of) the amino acid sequence set forth in SEQ ID NO: 29, and an Fc comprising (such as consisting of) the amino acid sequence set forth in SEQ ID NO: 30.

Pharmaceutical Compositions

Also provided are compositions, including pharmaceutical formulations, comprising an anti-CD8 antibody, or polynucleotides comprising sequences encoding an anti-CD8 antibody. In certain embodiments, compositions comprise one or more antibodies that bind to CD8, or one or more polynucleotides comprising sequences encoding one or more antibodies that bind to CD8. These compositions may further comprise suitable carriers, such as pharmaceutically acceptable excipients including buffers, which are well known in the art.

Pharmaceutical formulations of an anti-CD8 antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary (e.g., an immunotherapeutic agent) for the particular indication being treated (e.g., cancer), preferably those with complementary activities that do not adversely affect each other. For example, it may be desirable to further provide statin. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

Articles of Manufacture and Kits

In another aspect, provided is an article of manufacture or kit containing materials useful for predicting the responsiveness of a subject having cancer to an immunotherapeutic agent, for monitoring disease progression in a subject having cancer, and/or monitoring treatment progress in a subject having cancer.

In certain embodiments, the article of manufacture or kit comprises a container containing one or more of the anti-CD8 antibodies or the compositions described herein. In certain embodiments, the article of manufacture or kit comprises a container containing nucleic acids(s) encoding one (or more) of the anti-CD8 antibodies or the compositions described herein. In some embodiments, the kit includes a cell of cell line that produces an anti-CD8 antibody as described herein. In some embodiments, the kit includes an monovalent anti-CD8 antibody. In some embodiments, the monovalent anti-CD8 antibody is a one armed antibody. In some embodiments, the one armed anti-CD8 antibody comprises a full length heavy chain comprising (such as consisting of) the amino acid sequence set forth in SEQ ID NO: 28, a light chain comprising (such as consisting of) the amino acid sequence set forth in SEQ ID NO: 29, and an Fc comprising (such as consisting of) the amino acid sequence set forth in SEQ ID NO: 30.

In some embodiments, the kit includes one or more positive controls, for example CD8 (or fragments thereof) or $CD8^+$ cells. In some embodiments, the kit includes negative controls, for example a surface or solution that is substantially free of CD8.

In certain embodiments, the article of manufacture or kit comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing cancer and may have a sterile access port (for example the container may be an intravenous solution bag or a vial having a stopper pierceable by a hypodermic injection needle). At least one agent in the composition is an anti-CD8 antibody described herein. The label or package insert indicates that the composition is used for predicting the responsiveness of a subject having cancer to an immunotherapeutic agent, for monitoring disease progression in a subject having cancer, and/or monitoring treatment progress in a subject having cancer.

Moreover, the article of manufacture or kit may comprise (a) a first container with a composition contained therein, wherein the composition comprises an anti-CD8 antibody described herein; and (b) a second container with a composition contained therein, wherein the composition comprises a further cytotoxic or otherwise therapeutic agent. In some embodiments, the therapeutic agent is an immunotherapeutic agent, as described herein.

The article of manufacture or kit provided herein may further comprise a package insert indicating that the composition(s) can be used to predict the responsiveness of a subject having cancer to an immunotherapeutic agent, to monitor disease progression in a subject having cancer, and/or monitor treatment progress in a subject having cancer. Additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture or kit may include an immunoconjugate provided herein in place of (or in addition to) an anti-CD8 antibody. In certain embodiments, the kit comprises an anti-CD8 antibody provided herein comprising a desferrioxamine compound (e.g., N-succinyl-desferrioxamine). See, e.g., Vugts et al. (2017) *Eur J Nucl Med Mol Imaging.* 44:286-295 and Rudd et al. (2016) *Chem Commun.* 52: 11859-12000. In certain embodiments, the kit comprises an immunoconjugate, i.e., an anti-CD8 antibody conjugated to a detectable label, e.g., a detectable label described elsewhere herein. In certain embodiments, the detectable label is $^{89}Z$, $^{124}I$, or $^{18}F$.

EXAMPLES

Example 1: Humanization of and Affinity Maturation of OKT8

The murine variable regions of the OKT8 antibody were humanized by grafting the murine CDRs onto a human framework using a human kappa I/VH1 framework. The humanized OKT8 antibody served as the basis in vitro phage display-based affinity maturation experiments to generate variants with improved binding performance. Such variants are shown in Tables 4 and 5 below.

TABLE 4

| Variant | CDR-L1 | CDR-L2 | CDR-L3 |
|---|---|---|---|
| | | OKT8 | |
| huOKT8.v1 | SISQY (SEQ ID NO: 1) | SGSTLQ (SEQ ID NO: 3) | HNENPL (SEQ ID NO: 4) |
| huOKT8.v9 | SISQY (SEQ ID NO: 1) | SGSTLQ (SEQ ID NO: 3) | HNEFPV (SEQ ID NO: 5) |
| huOKT8.v10 | SISQY (SEQ ID NO: 1) | SGSTLQ (SEQ ID NO: 3) | HNEFPP (SEQ ID NO: 6) |
| huOKT8.v11 | SISQY SEQ ID NO: 1) | SGSTLQ (SEQ ID NO: 3) | VNEFPP (SEQ ID NO: 7) |
| huOKT8.v12 | SISQY (SEQ ID NO: 1) | SGSTLQ (SEQ ID NO: 3) | VNEFPV (SEQ ID NO: 8) |
| huOKT8.v15 | SISQY (SEQ ID NO: 1) | SGSTLQ (SEQ ID NO: 3) | VNEFPV (SEQ ID NO: 8) |
| huOKT8.v17 | SISKY (SEQ ID NO: 2) | SGSTLQ (SEQ ID NO: 3) | VNEFPV (SEQ ID NO: 8) |

TABLE 5

| Variant | CDR-H1 | CDR-H2 | CDR-H3 |
|---|---|---|---|
| OKT8 | | | |
| huOKT8.v1 | GFNIKDTYIH (SEQ ID NO: 9) | RIDPANDNTLYASKFQG (SEQ ID NO: 10) | GRGYGYYVFDH (SEQ ID NO: 12) |
| huOKT8.v9 | GFNIKDTYIH (SEQ ID NO: 9) | RIDPANDNTLYASKFQG (SEQ ID NO: 10) | GRGYGYYVFDH (SEQ ID NO: 12) |
| huOKT8.v10 | GFNIKDTYIH (SEQ ID NO: 9) | RIDPANDNTLYASKFQG (SEQ ID NO: 10) | GRGYGYYVFDH (SEQ ID NO: 12) |
| huOKT8.v11 | GFNIKDTYIH (SEQ ID NO: 9) | RIDPANDNTLYASKFQG (SEQ ID NO: 10) | GRGYGYYVFDH (SEQ ID NO: 12) |
| huOKT8.v12 | GFNIKDTYIH (SEQ ID NO: 9) | RIDPANDNTLYASKFQG (SEQ ID NO: 10) | GRGYGYYVFDH (SEQ ID NO: 12) |
| huOKT8.v15 | GFNIKDTYIH (SEQ ID NO: 9) | RIDPANDNTLYARKFQG (SEQ ID NO: 11) | TRGYGYYVEDT (SEQ ID NO: 13) |
| huOKT8.v17 | GFNIKDTYIH (SEQ ID NO: 9) | RIDPANDNTLYASKFQG (SEQ ID NO: 10) | GRGYGYYVFDH (SEQ ID NO: 12) |

The $K_D$s of variants huOKT8.v9-huOKT8.v12 and huOKT8.A-huOKT8.M were determined via surface plasmon resonance (SPR). The results of the SPR analyses are shown in Table 6.

TABLE 6

| Variant | Ratio of $K_D$ huOKT8.v1/$K_D$ variant for binding to huCD8 |
|---|---|
| OKT8 | 1 X |
| huOKT8.v1 | 1 X |
| huOKT8.v9 | 37 X |
| huOKT8.v10 | 18 X |
| huOKT8.v11 | 37 X |
| huOKT8.v12 | 73 X |
| huOKT8.v15 | 210 X |
| huOKT8.v17 | 210 X |

huOKT8.v9 and huOKT8.v11 were selected for further characterization.

Example 2: Characterization of Humanized Affinity Matured OKT8 Variants Antibodies FIG. 2A, which provides an alignment of the amino acid sequences of human CD8, rhesus monkey CD8, and cynomolgous monkey CD8, shows that there is 94% amino acid identity between human CD8 and cynomolgous CD8 (i.e., cyno CD8), and 94% amino acid identity between human CD8 and rhesus CD8.

OKT8.v9 and OKT8.v11 antibodies were evaluated for binding to cyno CD8 and to rhesus CD8, as compared to human CD8, in a series of surface plasmon resonance (SPR) and FACS analyses. The results are shown in Table 7 below.

TABLE 7

| | human CD8 | | cyno CD8 | | rhesus CD8 | |
|---|---|---|---|---|---|---|
| | SPR | FACS | SPR | FACS | SPR | FACS |
| OKT8 | 13 nM | 20 nM | | | | |
| huOKT8.v1 | 18 nM | 20 nM | 5250 nM | ND‡ | | |
| OKT8.v9 | 0.3 nM | 2 nM | 103 nM | 44 nM | ND‡ | 121 nM |
| OKT8.v11 | 0.2 nM | 2 nM | 23 nM | 13 nM | ND‡ | 20 nM |

‡= no detectable binding

As determined by SPR, OKT.v9 Fab demonstrated a 37-fold improvement in binding to human CD8 and a 50-fold improvement in binding to cyno CD8, compared to huOKT8.v1 (i.e., a variant that was generated during an early stage of affinity maturation). As determined by SPR, OKT.v11 Fab demonstrated a 55-fold improvement in binding to human CD8 and a 230-fold improvement in binding to cyno CD8, compared to huOKT8.v1. OKT8.v11 showed no cross-reactivity with mouse CD8 or rat CD8, as determined via FACS with $CD8^+$ cells isolated from mouse blood or rat blood.

Figure 2B:
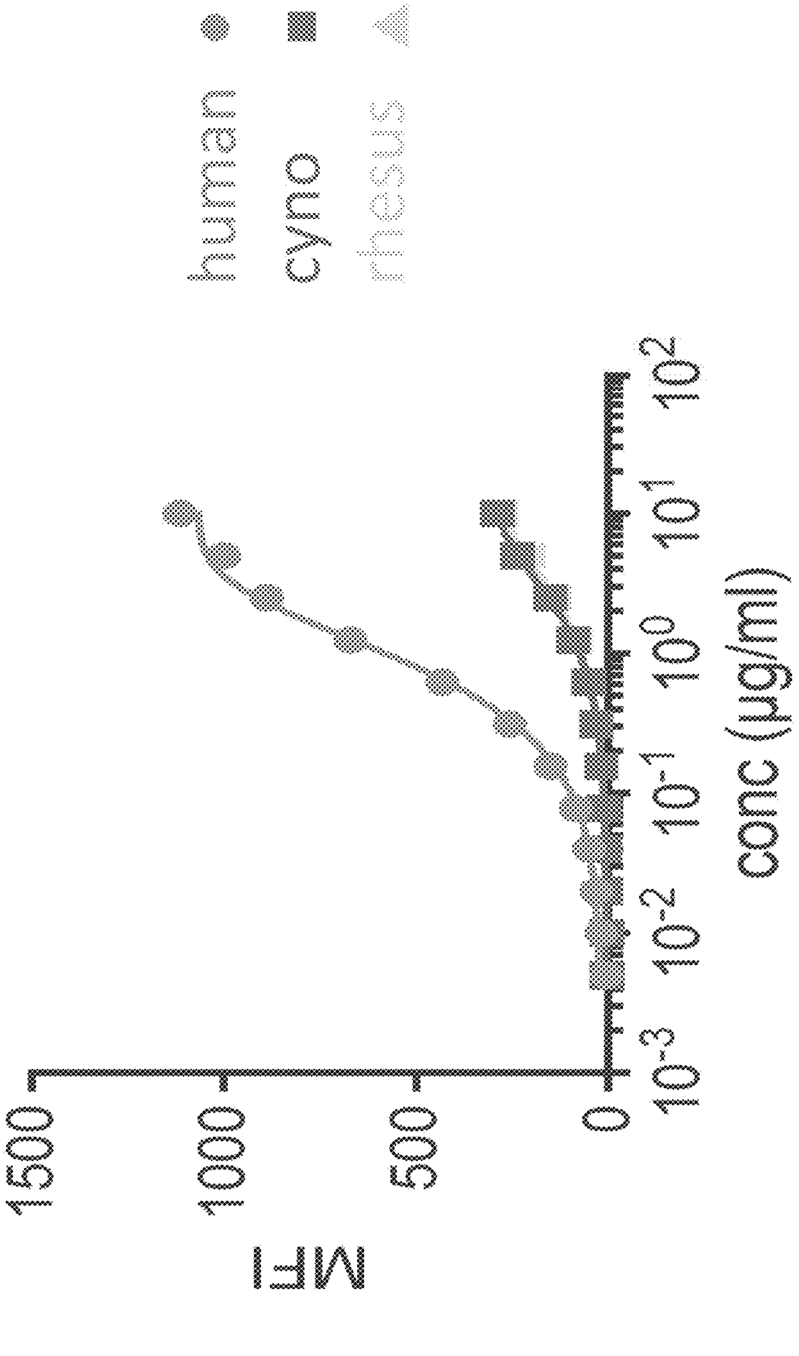
FIG. 2B shows the results of experiments that were performed to determine whether huOKT8.v11 can bind to CHO cells expressing recombinant human CD8, rhesus CD8, or cynomolgous CD8.

Complementary SPR and FACS analyses were performed using primary peripheral blood mononuclear cells (PBMCs) isolated from fresh blood obtained from humans, rhesus monkeys, or cyno monkeys. As shown in FIG. 2B, huOKT8.v11 binds human CD8, cyno CD8, and rhesus CD8.

huOKT8.v11 was reformatted as a one-armed IgG1 antibody comprising knob-in-hole mutations (i.e., T366S L358A Y407V in the "hole" heavy chain and T366W in the "knob" Fc), as well as the L234A, L235A, and P329G effector function mutations to produce huOKT8.v11-OA-LALAPG. huOKT8.v11-OA-LALAPG was then characterized further in a series of in vitro T-cell function and cytokine release assays.

First, $CD8^+$ T cell responses to polyclonal T-cell stimulation by anti-CD3 were assessed in the presence of huOKT8.v11-OA-LALAPG. $CD8^+$ T cells were isolated from human buffy coats using Human $CD8^+$ T Cell Enrichment Kit (STEMCELL™ Technologies; Seattle, WA) according to manufacturer's instructions. Briefly, RosetteSep™ Enrichment Cocktail was added to blood at 50 μL/mL blood, gently mixed, then incubated for 20 minutes at room temperature. Samples were diluted with equal volume of phosphate buffered saline (PBS) supplemented with 2% fetal bovine serum. Diluted samples were then layered onto an equal volume of Ficoll® Paque Plus (GE Healthcare; St. Louis, MO), and centrifuged for 20 minutes at 1200×g at room temperature with the brake off. Following gradient centrifugation, the interface was collected, pelleted, and red blood cells were lysed with Ammonium-Chloride-Potassium Lysis Buffer. The purity of the isolated $CD8^+$ cell population was assessed by flow cytometry. Cells were stained with anti-CD8 antibody (Clone RPA T8) phycoerythrin (PE) from BD Biosciences (San Jose, CA). Cells were incubated for 20 minutes in the dark at 4° C., and washed twice with fluorescence-activated cell sorting (FACS) Stain Buffer (BD Biosciences). Samples were run on a BD Biosciences FACSCalibur™ flow cytometer. Purity of isolated CD8$^+$ T cells was greater than 95% for each donor. Wells designated for polyclonal T cell stimulation were pre coated with anti-CD3 antibody (Clone SP34, BD Biosciences) at a starting concentration of 5 μg/mL in PBS in a volume of 100 μL/well, with 3-fold serial dilution to provide a 7-point titration curve ranging from 7 ng/mL to 5 μg/mL. For pre-coating, plates were incubated overnight at 4° C. Prior to addition of cells, anti-CD3 antibody was removed from wells by aspiration. Purified CD8$^+$ cells were prepared at a concentration of 5×106 cells/mL, then added to 96-well flat-bottom polystyrene tissue culture plates at 0.5×106 cells/well in a volume of 100 μL supplemented with anti CD28 antibody (Clone CD28.2, BD Biosciences) prepared for a concentration of 1 μg/mL in the final volume of 200 μL per well. Plates were incubated in a humidified incubator with 5% CO2 for three days. After three days, 100 μL of supernatant was collected for measurement of interferon gamma (IFN-γ) concentration. An ELISA was performed using DuoSet Human IFN-γ kit (R&D Systems; Minneapolis, MN). Next, 1 μCi [$^3$H]thymidine in a volume of 50 μL was added to wells, then plates were returned to the incubator. After a 16 hour overnight culture, cells were harvested, and incorporation of [$^3$H]thymidine was measured by liquid scintillation counting. The effect of OKT8.v11-OA-LALAPG was only tested at the high concentration of 100 μg/mL.

Figure 3A:
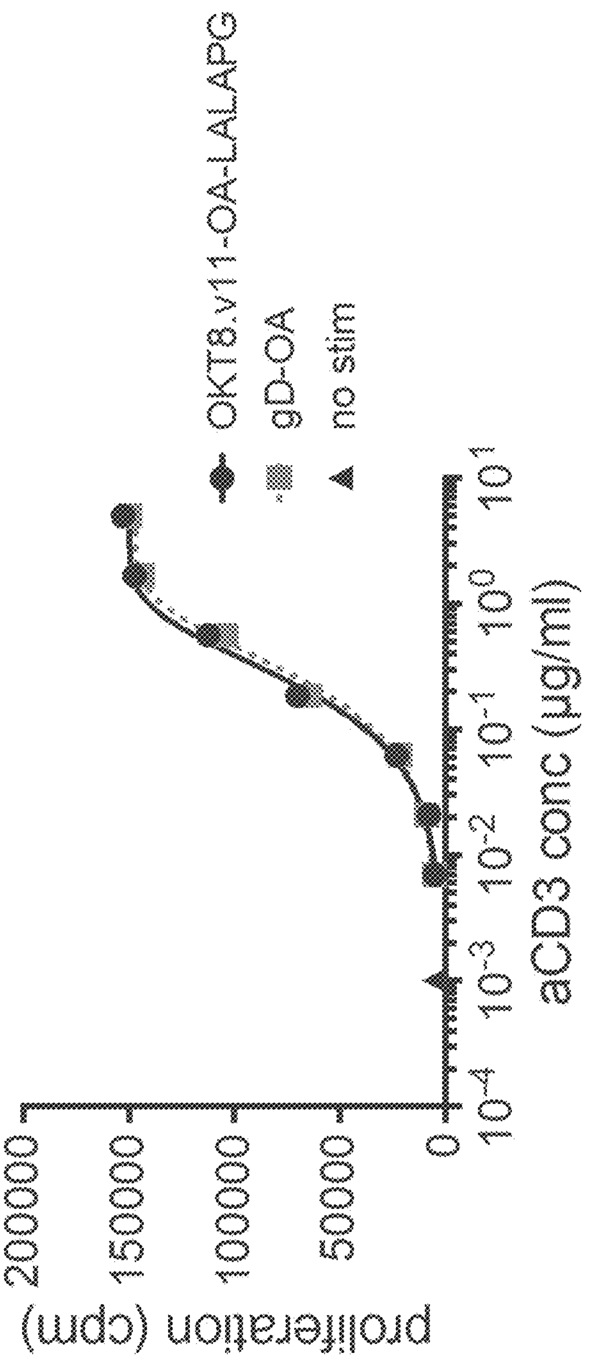
FIG. 3A provides the results of experiments that were performed to assess $CD8^+$ T cell responses to polyclonal T cell stimulation via anti-CD3 in the presence of OKT8.v11-OA-LALAPG or anti-gD-OA (isotype control).
Figure 3B:
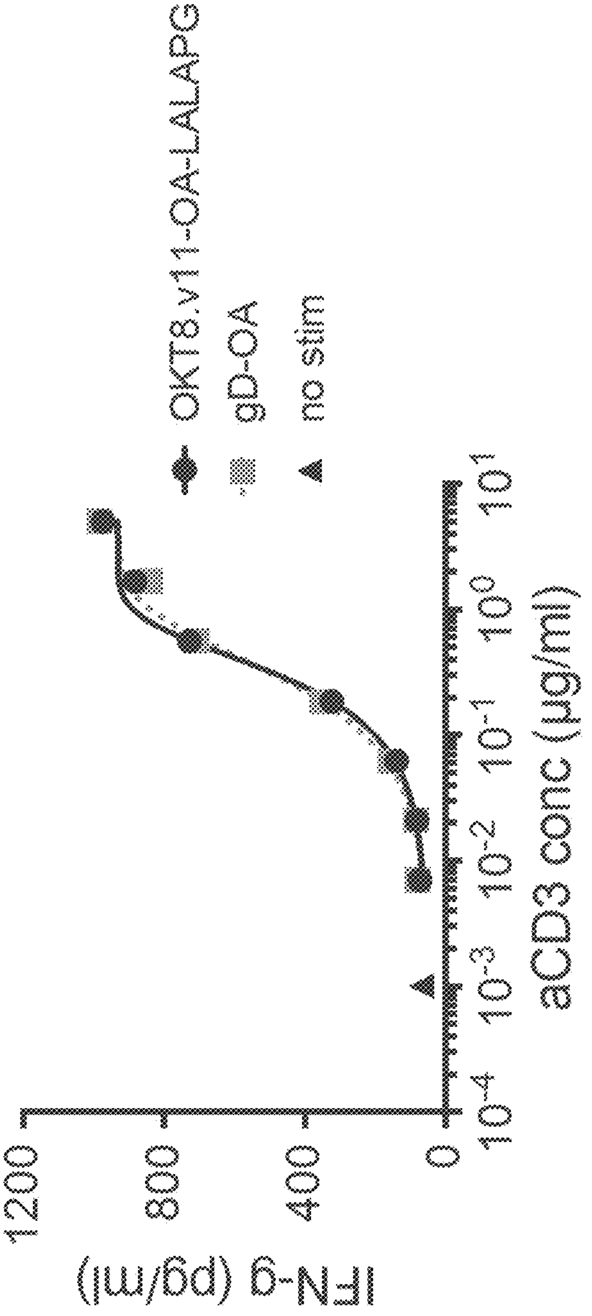
FIG. 3B provides the results of experiments that were performed to assess $CD8^+$ T cell IFN-gamma responses to polyclonal T cell stimulation via anti-CD3 in the presence of OKT8.v11-OA-LALAPG or anti-gD-OA (isotype control).

Purified CD8$^+$ T cells were activated in vitro with varying concentrations of anti-CD3 antibody in the presence of 100 μg/ml OKT8.v11-OA-LALAPG or 100 μg/mlisotype control (anti-glycoprotein D-OA, or "anti-gD-OA"). OKT8.v11-OA-LALAPG did not affect proliferation of CD8$^+$ T cells (FIG. 3A) or IFN-γ responses by CD8$^+$ T cells (FIG. 3B) at any concentration of anti-CD3. CD8$^+$ T cell proliferation and IFN-γ responses in the presence of OKT8.v11-OA-LALAPG were comparable to isotype control at all concentrations tested.

Next, CD8$^+$ T cells were activated in vitro with tetanus toxoid in order to assess the effect of OKT8.v11-OA-LALAPG on antigen-specific stimulation in an antigen presentation cell-dependent manner. Briefly, Peripheral blood mononuclear cells (PBMCs) were isolated from buffy coats as previously described. PBMCs were labeled with carboxyfluorescein succinimidyl ester (CFSE) at a concentration of 2.5 μM for 5 minutes at room temperature, and then washed five times in PBS prior to stimulation. Antigen-specific cell stimulation was performed in vitro using tetanus toxoid (derived from Clostridium tetani; Calbiochem, EMD Millipore; Billerica, MA) as follows. PBMCs (1×106 in a volume of 100 μL) were added to 96 well flat bottom polystyrene tissue culture plates. Wells designated for antigen-specific stimulation included tetanus toxoid at a concentration of 5 μg/mL in a final volume of 200 μL/well. OKT8.v11-OA-LALAPG or isotype control anti-gD-OA was prepared at the 2× concentration of 200 μg/mL, then each was serially diluted 10 fold. Then 100 μL of antibody was added to appropriate wells, bringing the final well volume to 200 μL. The resulting 10-point titration curve ranged from 3 ng/mL to 100 μg/mL. Plates were incubated in a humidified incubator with 5% $CO_2$ for 6 days. Flow cytometry was used to assess proliferation by CFSE dilution. Cells were co-stained with anti-CD8 PE to assess proliferation of CD8$^+$ T cells, respectively. Cells were additionally stained with anti-CD25 (Clone M-A251) allophycocyanin (APC) (BD Biosciences) to assess cell activation status, with CD25$^{high}$ expression marking activation.

Figure 3C:
FIG. 3C provides the results of experiments that were performed to assess $CD8^+$ T cell proliferation in the presence of OKT8.v11-OA-LALAPG or anti-gD-OA (isotype control) following tetanus toxoid stimulation.
Figure 3D:
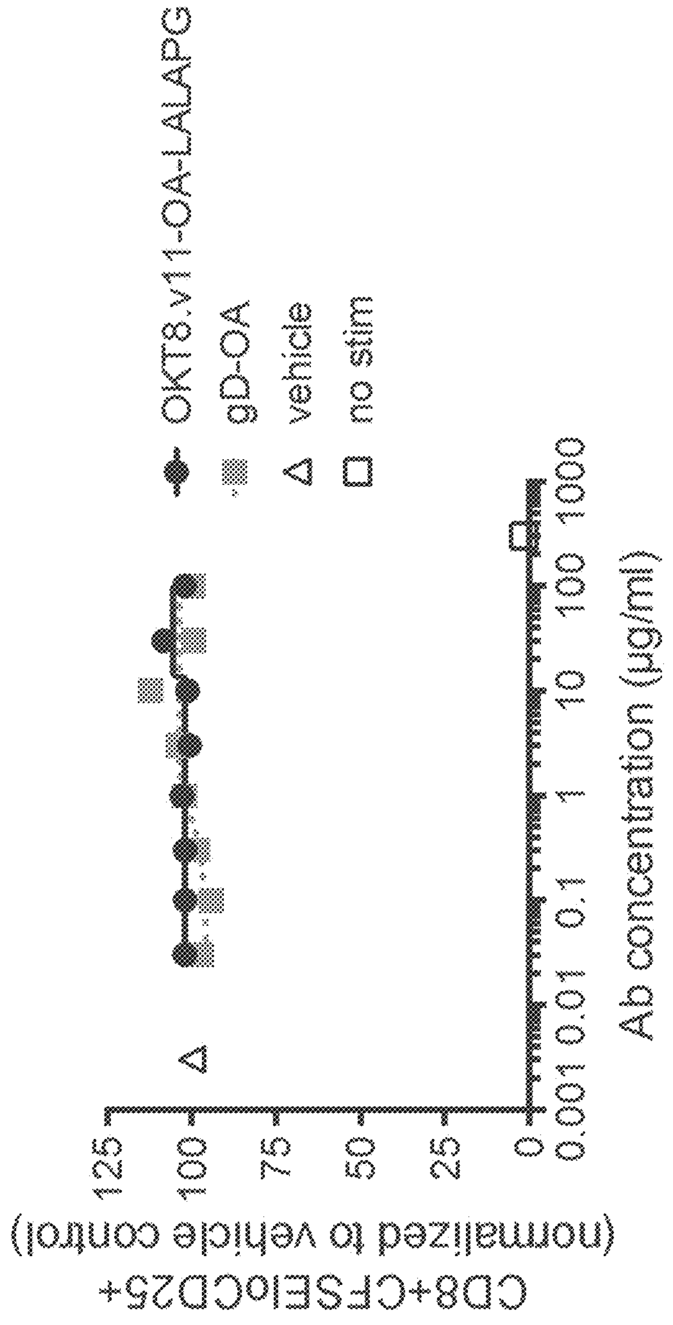
FIG. 3D provides the results of experiments that were performed to assess the level of CD25 expression in $CD8^+$ T cells that were incubated with OKT8.v11-OA-LALAPG or anti-gD-OA (isotype control) following tetanus toxoid stimulation.

CD8$^+$ T cells were stimulated with tetanus toxoid at the concentrations indicated in FIGS. 3C and 3D in the presence of OKT8.v11-OA-LALAPG or isotype control anti-gD-OA. Proliferation response, shown in FIG. 3C, was assessed by carboxyfluorescein diacetate succinimidyl ester (CFSE) dilution. The frequency of proliferating CD8$^+$ T cells as determined by cells undergoing more than one round of CFSE dilution was normalized to vehicle-treated cells, and the data are expressed as a percentage of vehicle. OKT8.v11-OA-LALAPG did not affect proliferation at the highest concentration tested (100 μg/mL). See FIG. 3C. The effects of OKT8.v11-OA-LALAPG and anti-gD-OA were comparable at all concentrations. In FIG. 3D, the activation status of proliferating CD8$^+$ T cells was assessed by measuring CD25 expression as a marker for activation. The frequency of CD25$^{high}$ cells was normalized to vehicle-treated cells, and the data are expressed as a percentage of vehicle. Neither OKT8.v11-OA-LALAPG nor anti-gD-OA affected activation of CD8$^+$ T cells at any concentration tested.

Figure 4A:
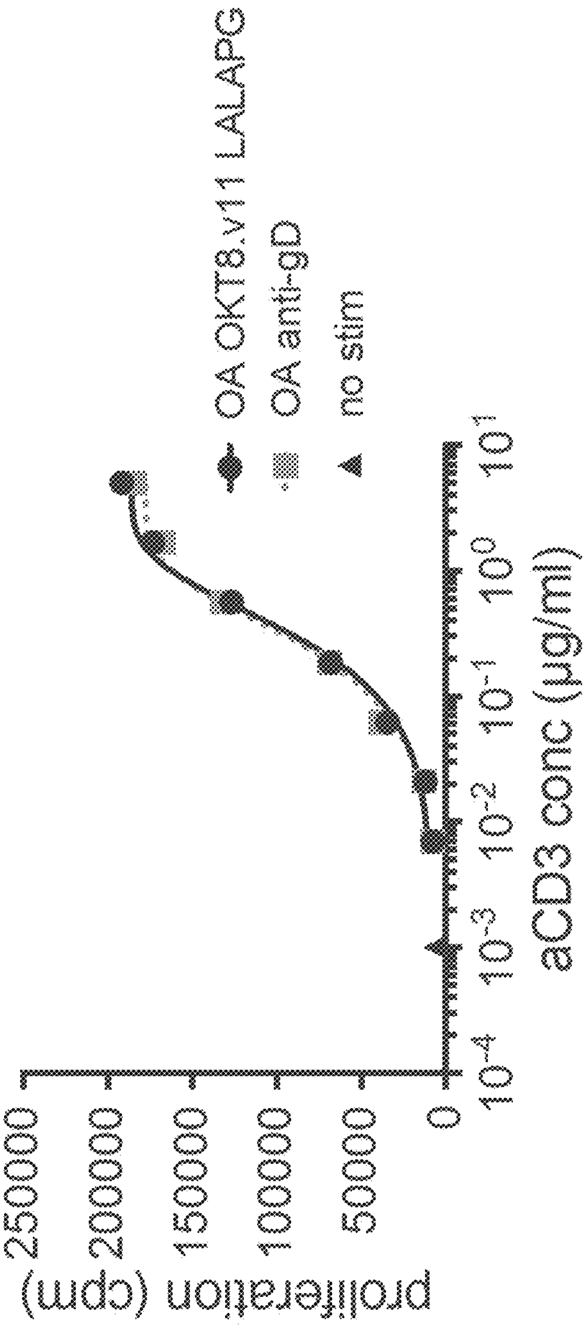
FIG. 4A provides the results of experiments that were performed to assess $CD^{4+}$ T cell responses to polyclonal T cell stimulation via anti-CD3 in the presence of OKT8.v11-OA-LALAPG or anti-gD-OA (isotype control).
Figure 4B:
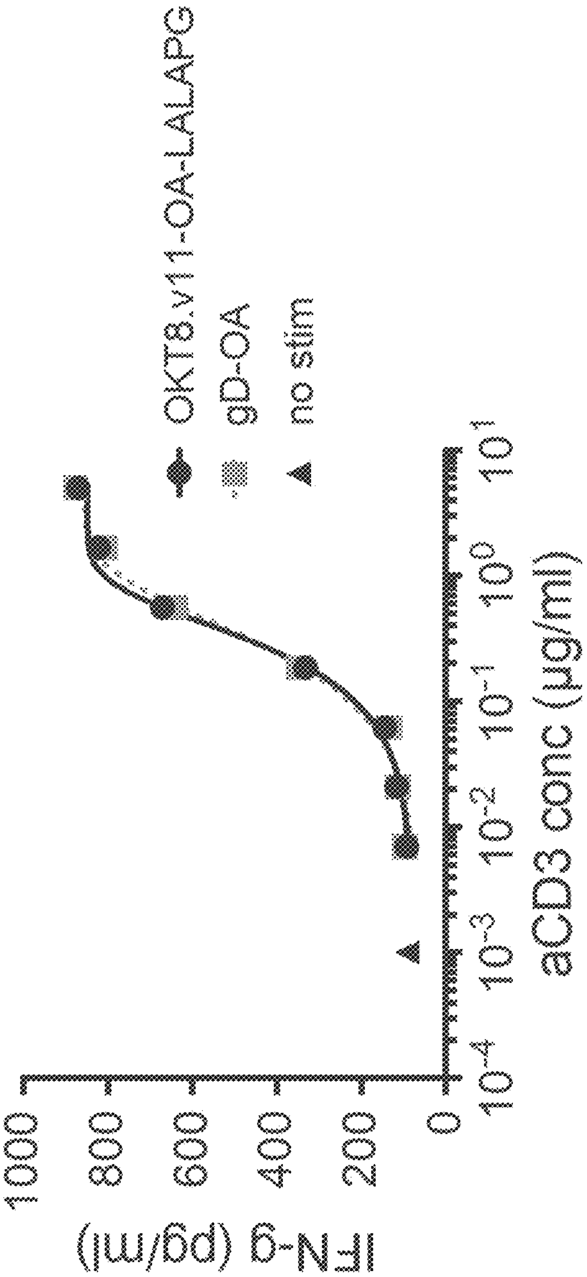
FIG. 4B provides the results of experiments that were performed to assess $CD^{4+}$ T cell IFN-gamma responses to polyclonal T cell stimulation via anti-CD3 in the presence of OKT8.v11-OA-LALAPG or anti-gD-OA (isotype control).

CD4$^+$ T cell responses to polyclonal T cell stimulation by anti-CD3 was assessed in the presence of OKT8.v11-OA-LALAPG and anti-gD-OA isotype control, as described above (CD4$^+$ T cells were isolated using Human CD4$^+$ T Cell Enrichment Kit (STEMCELL Technologies) and assessed via flow cytometry using anti-CD4 (Clone SK3)-PerCP antibodies from BD Biosciences (San Jose, CA)). OKT8.v11-OA-LALAPG did not affect CD4$^+$ T cell proliferation (see FIG. 4A) or IFN-γ (FIG. 4B) responses by CD4+ T cells at any concentration of anti-CD3. The effects of OKT8.v11-OA-LALAPG and anti-gD-OA isotype control were comparable all concentrations.

In vitro activation of CD4$^+$ T cells with tetanus toxoid was performed as described above to determine the effect of OKT8.v11-OA-LALAPG on antigen-specific stimulation in an antigen presentation cell dependent manner. (CD4$^+$ T cells were isolated using Human CD4$^+$ T Cell Enrichment Kit (STEMCELL Technologies) and assessed via flow cytometry using anti-CD4 (Clone SK3)-PerCP antibodies from BD Biosciences (San Jose, CA)). CD4$^+$ T cells stimulation was performed in the presence of indicated concentrations of OKT8.v11-OA-LALAPG or isotype control gD-OA, as described above. The frequency of proliferating CD4$^+$ T cells as determined by cells undergoing more than one round of CFSE dilution was normalized to vehicle-treated cells, and the data are expressed as a percentage of vehicle. OKT8.v11-OA-LALAPG did not affect proliferation at the highest concentration tested (100 μg/mL). See FIG. 3C. The effects of OKT8.v11-OA-LALAPG and anti-gD-OA were comparable at all concentrations. In FIG. 3D, the activation status of proliferating CD4$^+$ T cells was assessed by measuring CD25 expression as a marker for activation. The frequency of CD25$^{high}$ cells was normalized to vehicle-treated cells, and the data are expressed as a percentage of vehicle. Neither OKT8.v11-OA-LALAPG nor anti-gD-OA affected activation of CD4$^+$ T cells at any concentration tested.

Figure 3E:
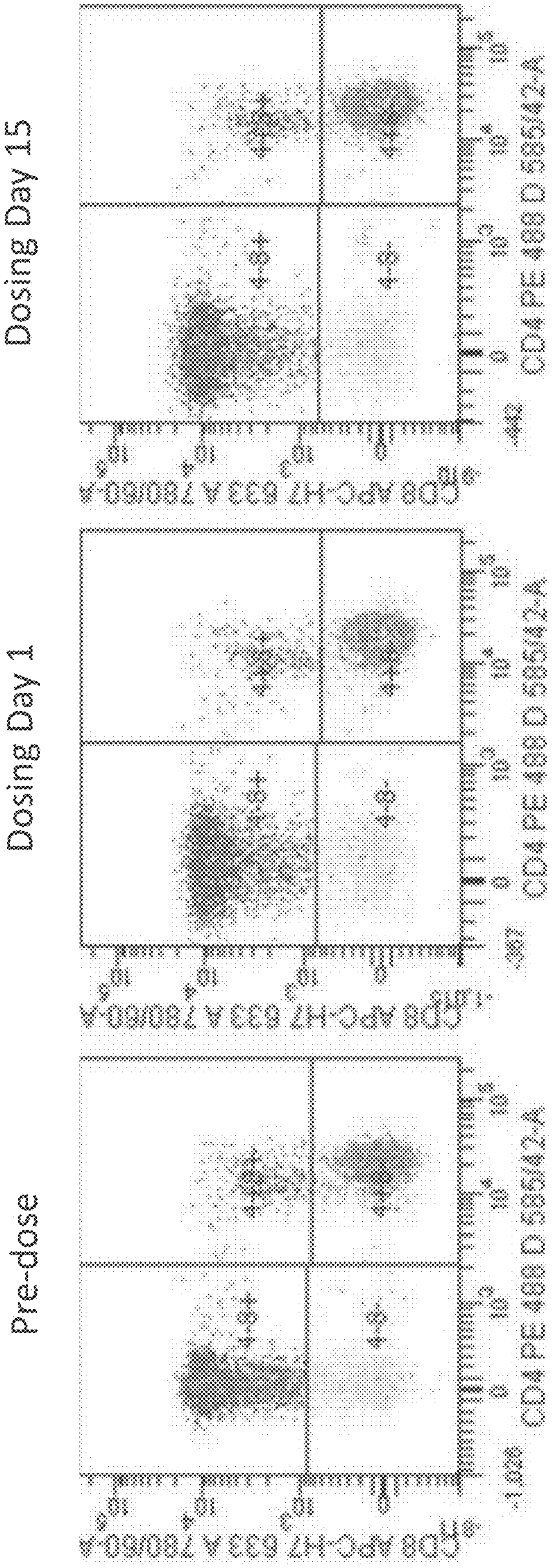
FIG. 3E provides the results of experiments that were performed to determine whether OKT8.v11-OA-LALAPG depletes $CD8^+$ T cells from circulation.

Additional experiments were performed to determine whether OKT8.v11-OA-LALAPG depletes CD8$^+$ T cells from circulation. Briefly, blood samples were obtained from cynomolgous monkeys prior to injection with 100 mg/kg OKT8.v11-OA-LALAPG, on Day 1 following injection, and on Day 15 following injection. During sample analysis, total lymphocyte populations were identified via flow cytometry using a lymphocyte gating strategy consisting of CD45 fluorescent staining and side-scatter characteristics (SSC) demarcation ($CD45^{bright}SSC^{dim}$) to delineate the lymphocyte populations. Next, B cell populations were identified through the use of fluorescently labeled anti-CD8 or fluorescently labeled anti-CD4 antibodies. As shown in FIG. 3E, no significant differences in Mean Fluorescent Intensity (MIF) for the $CD8^+$ gate over time, indicating that OKT8.v11-OA-LALAPG does not deplete $CD8^+$ T cells from circulation.

Figure 3F:
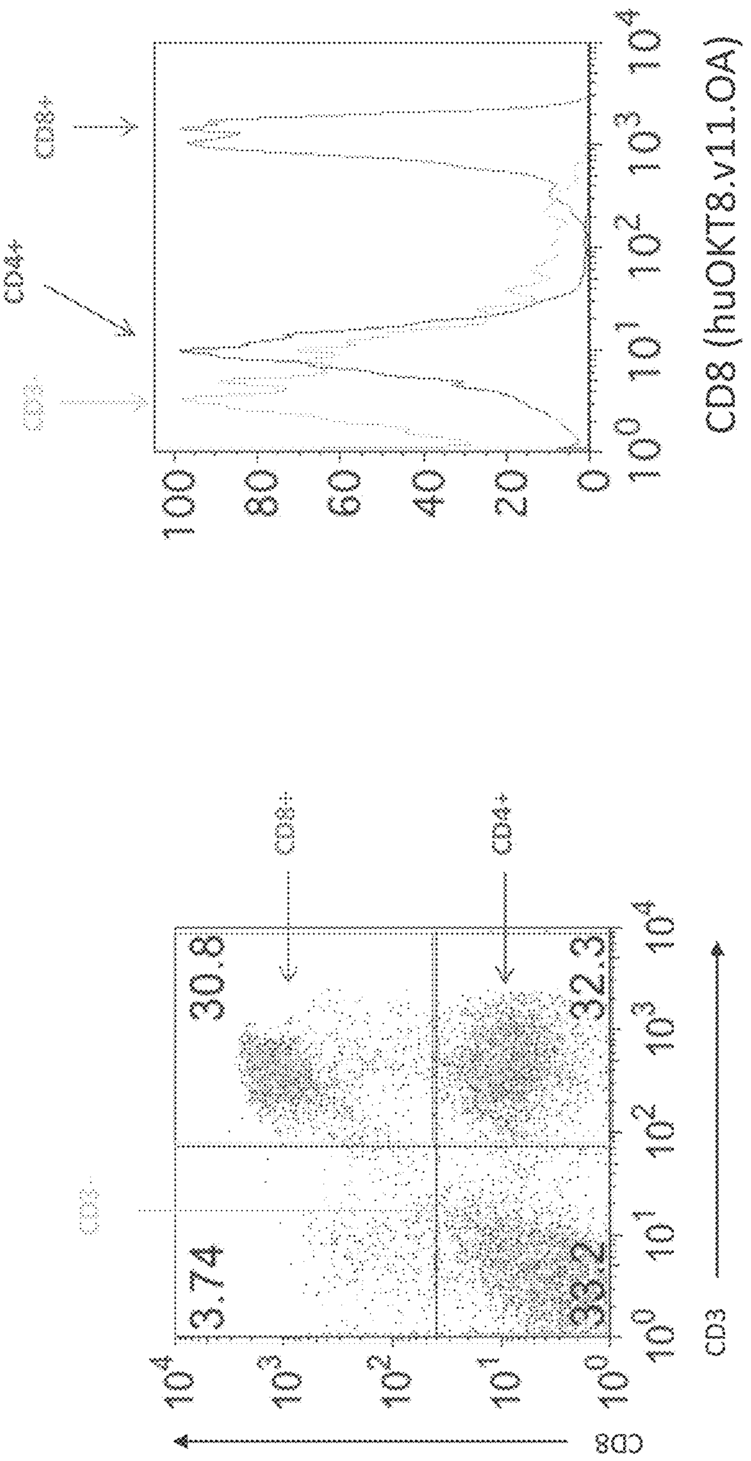
FIG. 3F provides the results of FACS experiments that were performed to determine whether OKT8.v11-OA bind $CD4^+$ T cells or $CD3^-$ T cells.

Further FACS analyses confirmed that OKT8.v11 does not bind $CD4^+$ T cells or $CD3^-$ T cells (see FIG. 3F).

Example 3: Evaluation of Various Antibody Formats for Molecular Imaging

Pilot immunoPET studies were performed using labeled anti-CD8 antibodies to evaluate the suitability of different antibody formats for molecular imaging in mice.

Two murine anti-CD8 constructs, namely $^{89}$Zr-mCD8-DANA (i.e., IgG1 format with DANA effector function mutations) or $^{89}$Zr-mCD8-$(Fab')_2$, were made using 21ED3, a hamster anti-mouse antibody. Each construct was injected into mice bearing murine CT26 colon carcinoma tumors, which are characterized by increased $CD8^+$ T cell infiltration. Tumor infiltration of $CD8^+$ T cells was not detected due to poor stability of the DANA and $(Fab')_2$ formats.

In a human CD8 model, $^{18}$F-OKT8.v11-Fab was tested following intrasplenic injection of human PBMCs into SCID.beige mice. However, no visible uptake of $^{18}$F-CD8-Fab was detected in the spleens of human PBMC-engrafted mice.

Figure 5A:
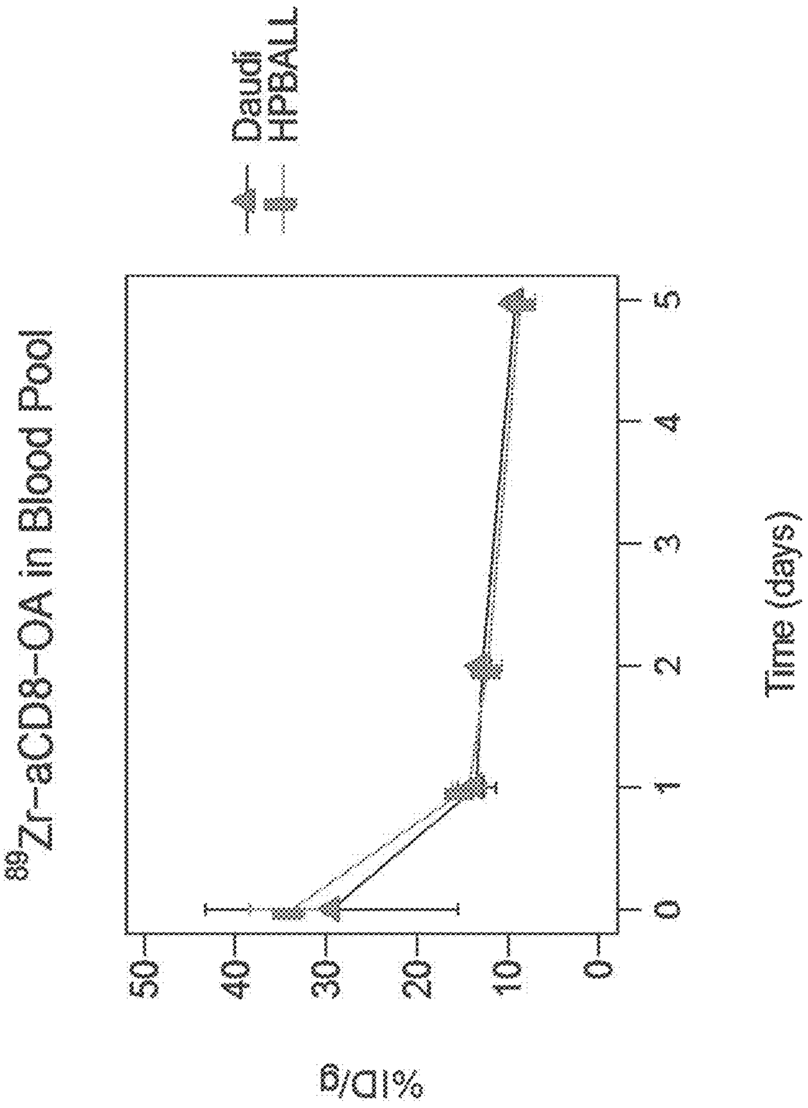
FIG. 5A shows the results of experiments that were performed to determine the amount of $^{89}$Zr-huOKT8.v1-OA that was present in the blood pool of HPB-ALL- or Daudi-xenografted mice.
Figure 5B:
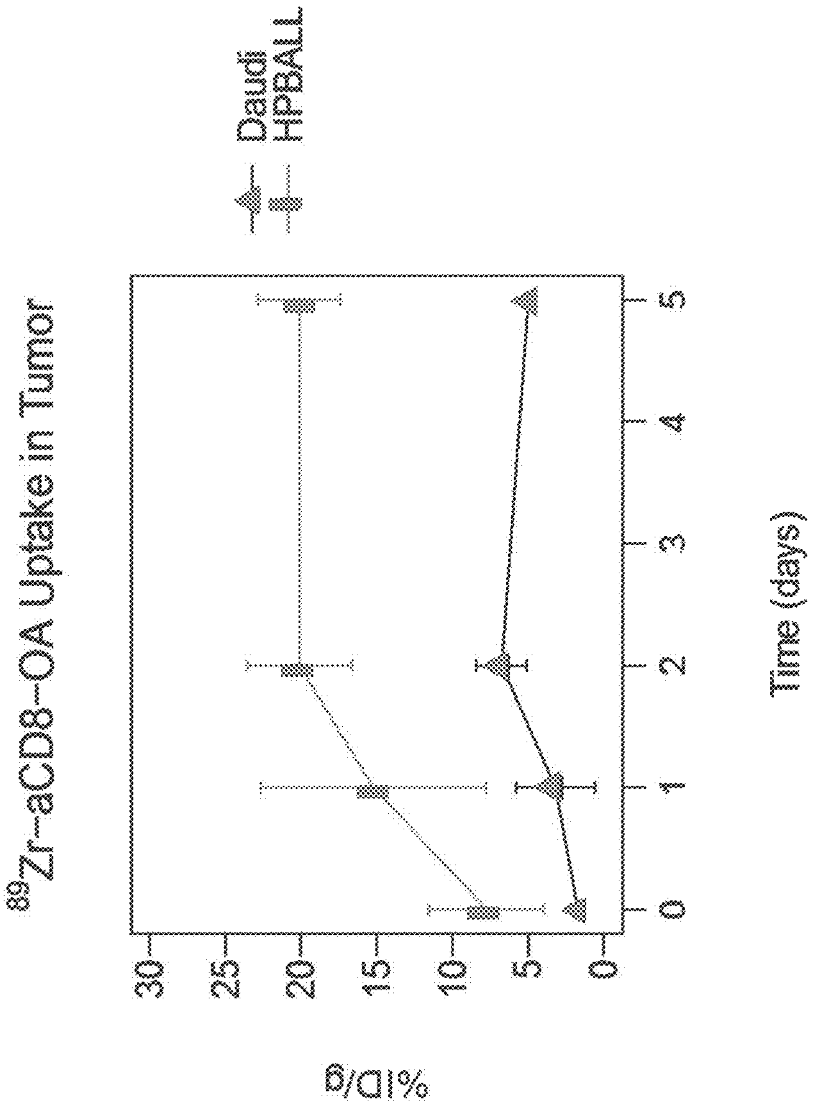
FIG. 5B shows the results of experiments that were performed to determine the amount of $^{89}$Zr-huOKT8.v1-OA that was present in the tumor tissue HPB-ALL- or Daudi-xenografted mice.

In a further human CD8 model, $^{89}$Zr-huOKT8.v1-OA (i.e., a one-armed antibody) was injected into mice bearing HPB-ALL (human T-cell leukemia) $CD8^+$ xenografted tumors or Daudi (human Burkitt's lymphoma) $CD8^-$ xenografted tumors. The mice were then monitored via PET scan at dosing, Day 1, Day 2, and Day 5 post initial dosing. FIGS. 5A and 5B show uptake of $^{89}$Zr-huOKT8.v1-OA as % initial dose per gram in tissue as a function of time in tumor tissue and heart tissue, respectively. $^{89}$Zr-huOKT8.v1-OA demonstrated CD8-dependent uptake in tumor tissue. See FIG. 5A. By contrast, minimal uptake of $^{89}$Zr-OA-CD8.v1 was observed in non-tumor tissue in either HPB-ALL xenografted mice or Daudi xenografted mice. See FIG. 5B.

Figure 4C:
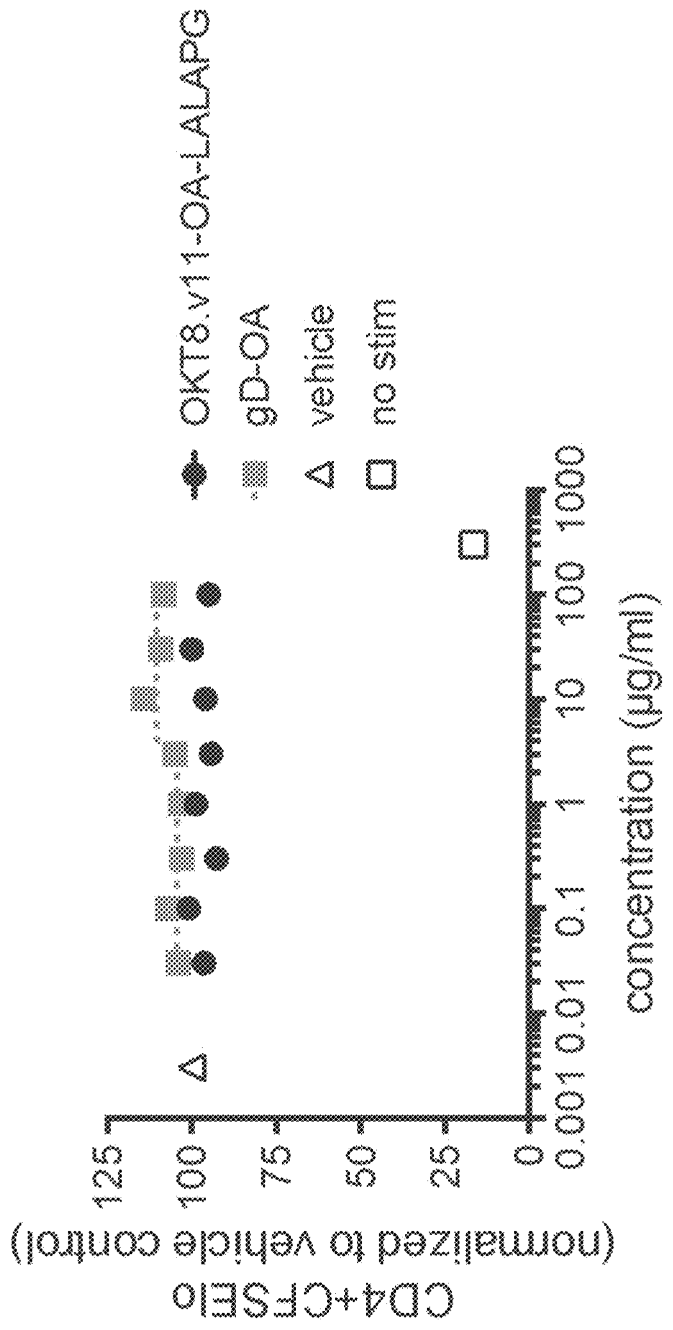
FIG. 4C provides the results of experiments that were performed to assess $CD^{4+}$ T cell proliferation in the presence of OKT8.v11-OA-LALAPG or anti-gD-OA (isotype control) following tetanus toxoid stimulation.
Figure 4D:
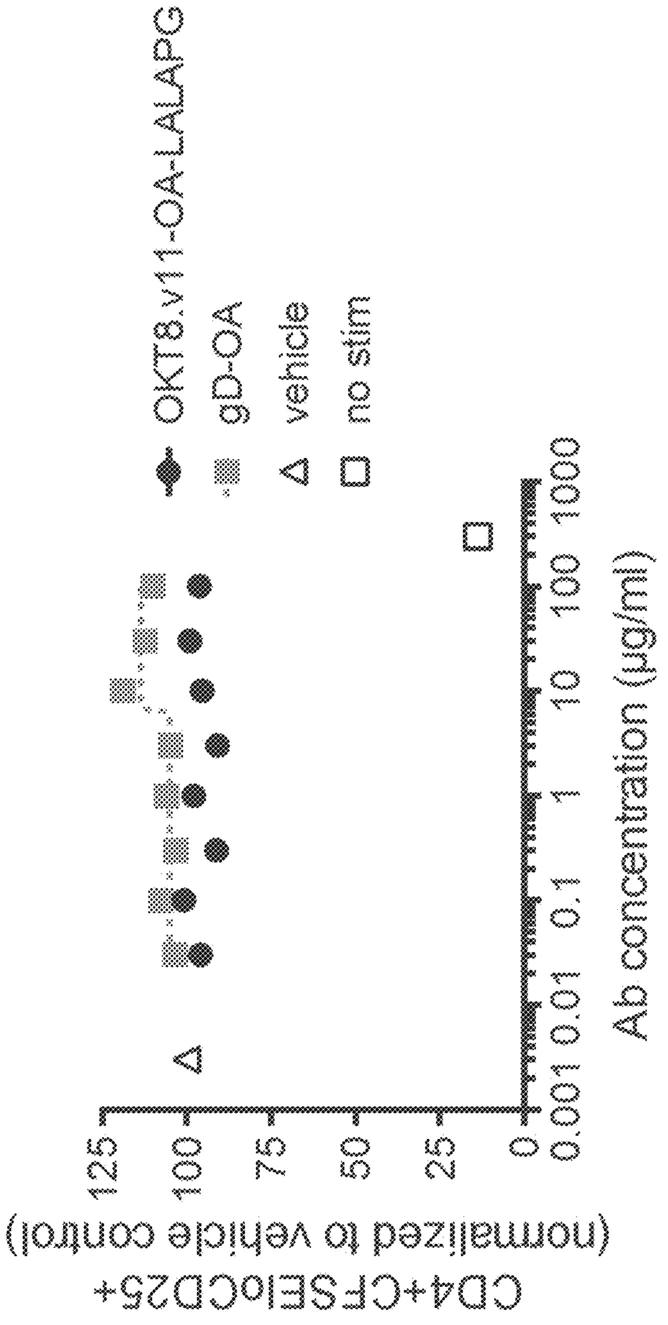
FIG. 4D provides the results of experiments that were performed to assess the level of CD25 expression in $CD^{4+}$ T cells that were incubated with OKT8.v11-OA-LALAPG or anti-gD-OA (isotype control) following tetanus toxoid stimulation.
Figure 6A:
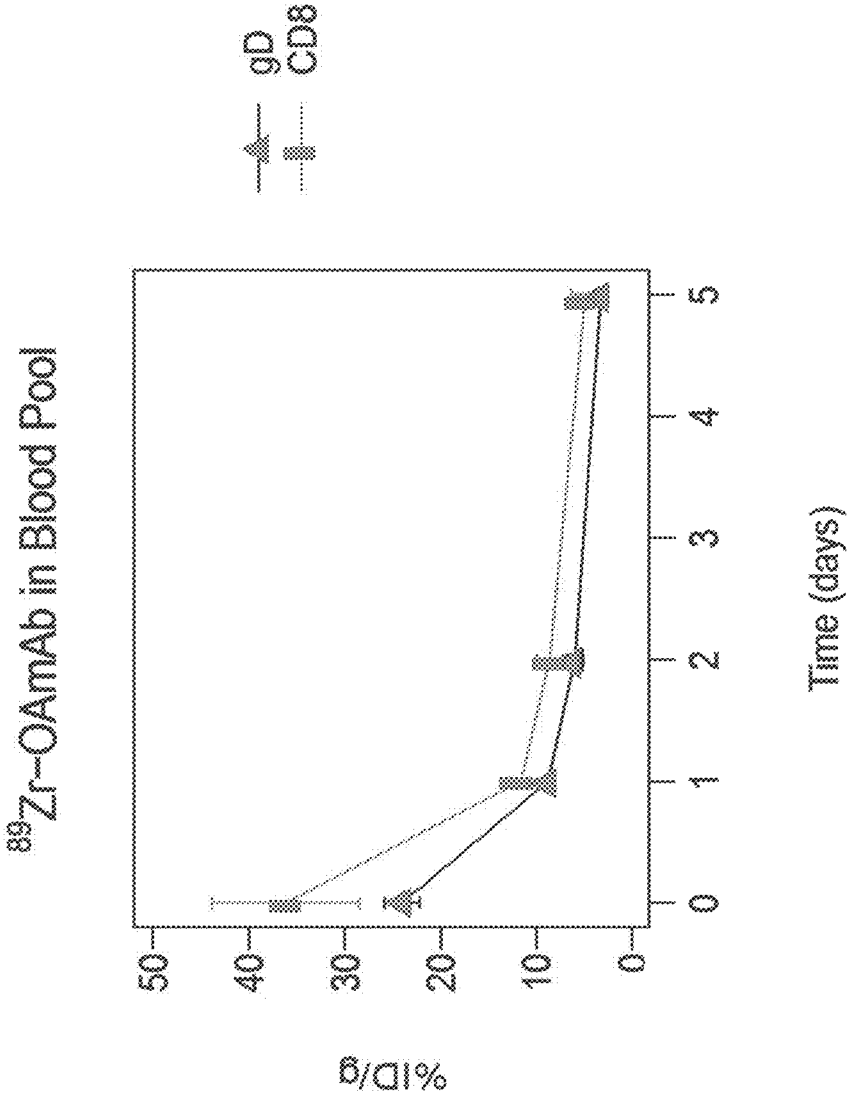
FIG. 6A shows the results of experiments that were performed to determine the amount of $^{89}$Zr-huOKT8.v1-OA or $^{89}$Zr-gD-OA in the blood pool of HPB-ALL-xenografted mice.
Figure 6B:
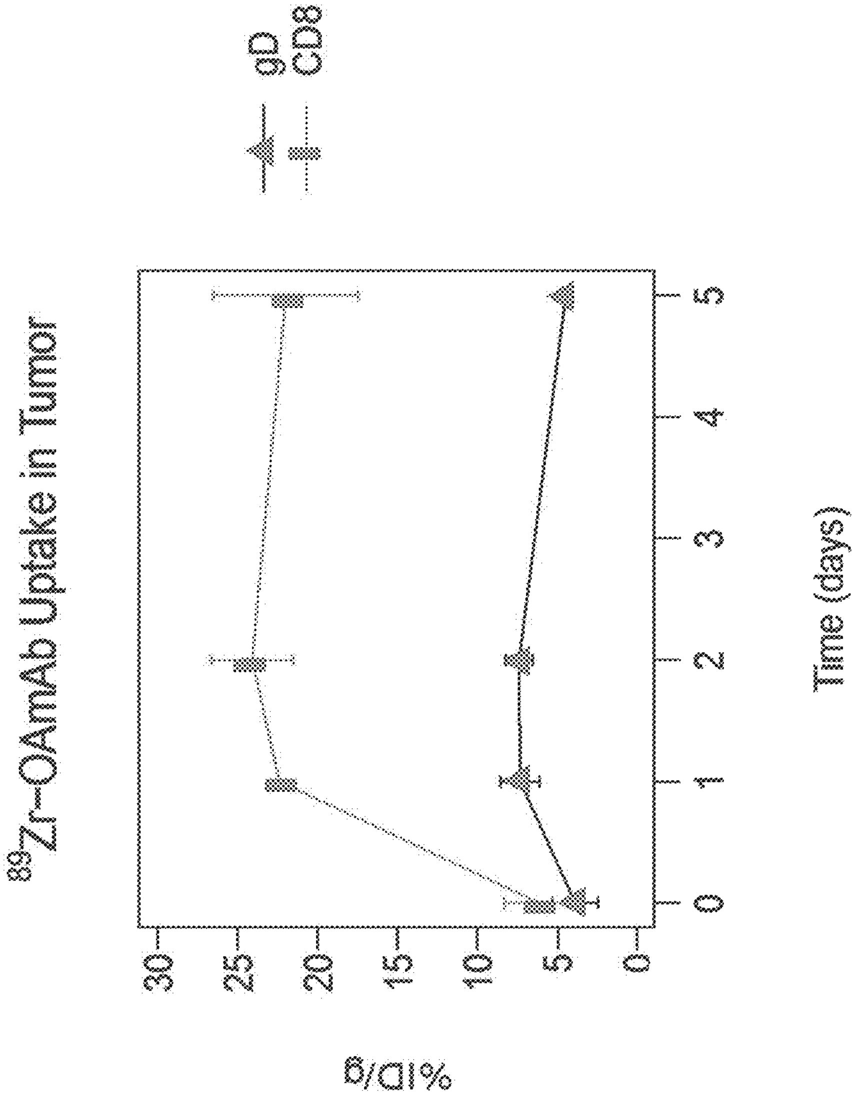
FIG. 6B shows the results of experiments that were performed to determine the amount of $^{89}$Zr-huOKT8.v1-OA or $^{89}$Zr-gD-OA that was taken up by tumor tissue in HPB-ALL-xenografted mice.
Figure 6C:
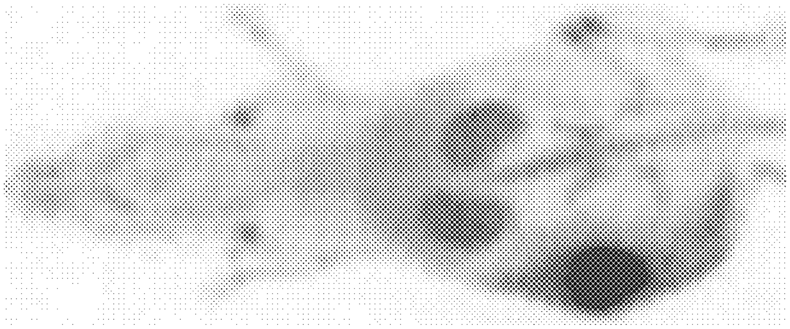
FIG. 6C shows a PET MIP of a HPB-ALL tumor xenografted mouse that was injected with $^{89}$Zr-huOKT8.v1-OA. The PET scans were performed on Day 5 post-injection.
Figure 7A:
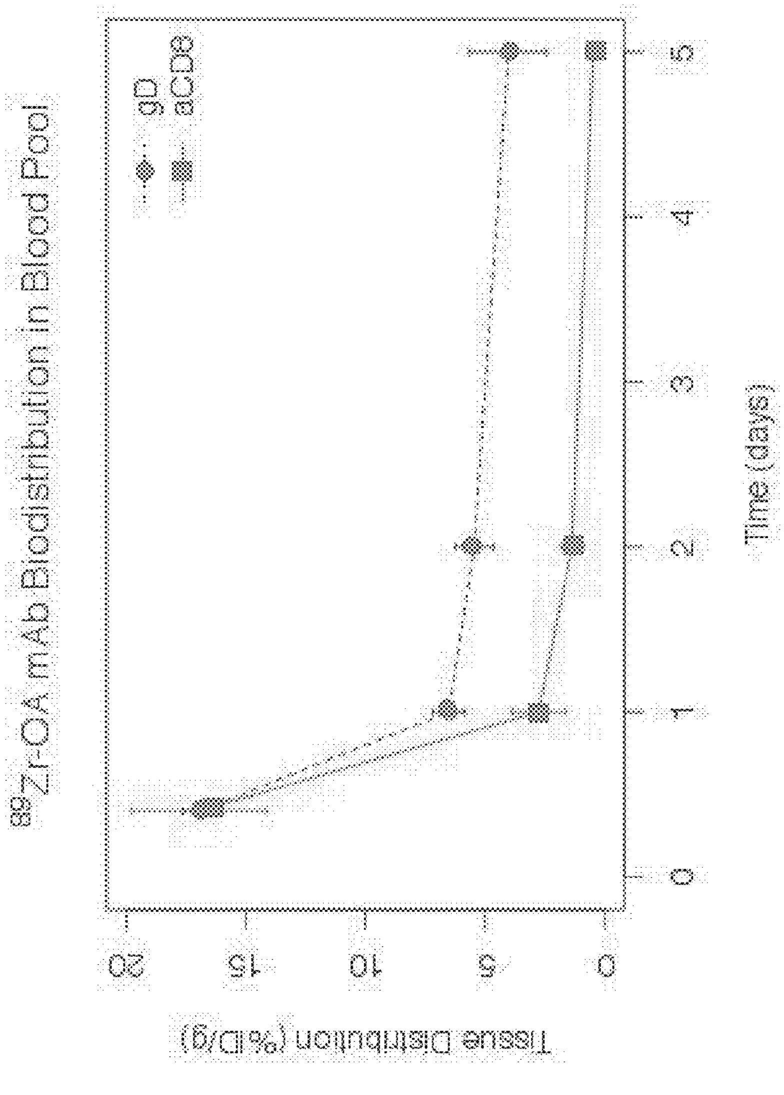
FIG. 7A shows the results of experiments that were performed to determine the amount of $^{89}$Zr-huOKT8.v9-OA or $^{89}$Zr-gD-OA in the blood pool of HPB-ALL-xenografted mice.
Figure 7B:
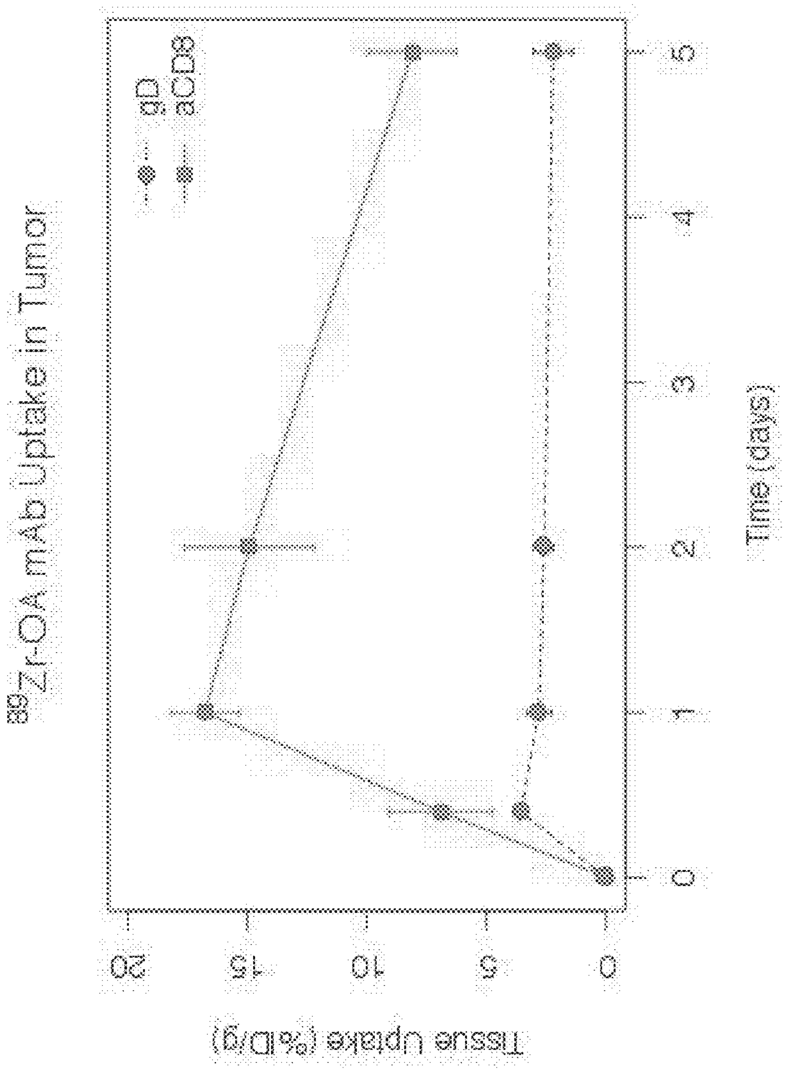
FIG. 7B shows the results of experiments that were performed to determine the amount of $^{89}$Zr-huOKT8.v1-OA or $^{89}$Zr-gD-OA that was taken up by tumor tissue in HPB-ALL-xenografted mice.

To confirm CD8-specificity of $^{89}$Zr-huOKT8.v1-OA uptake, complementary experiments were performed in HPB-ALL xenografted mice injected with $^{89}$Zr-huOKT8.v1-OA, $^{89}$Zr-huOKT8.v9-OA, or a control antibody, $^{89}$Zr-gD-OA, which targets glycoprotein D. Following injection the mice were monitored via PET scan at dosing, Day 1, Day 2, and Day 5 post initial dosing. Minimal $^{89}$Zr-huOKT8.v1-OA, $^{89}$Zr-huOKT8.v9-OA, or $^{89}$Zr-gD-OA was detected in the blood pool after two days. See FIGS. 6A and 7A, which show uptake of $^{89}$Zr-huOKT8.v1-OA, $^{89}$Zr-huOKT8.v9-OA, and $^{89}$Zr-gD-OA as % initial dose per gram in tissue as a function of time in blood. Uptake of $^{89}$Zr-huOKT8.v1-OA was observed in $CD8^+$ HPB-ALL tumor tissue, with a peak uptake of about 25%. See FIG. 6B. Comparable peak uptake was observed with $^{89}$Zr-huOKT8.v9-OA. See FIG. 7B. By contrast, only residual uptake of the control $^{89}$Zr-gD-OA was observed in HPB-ALL tumor tissue. See FIGS. 6B and 7B. Further, clearance of $^{89}$Zr-huOKT8.v1-OA and $^{89}$Zr-huOKT8.v9-OA was dominated by the kidney (see FIG. 4C for $^{89}$Zr-huOKT8.v1-OA). Unlike imaging tools that are predominantly cleared by the liver, the use of $^{89}$Zr-huOKT8.v1-OA or $^{89}$Zr-huOKT8.v9-OA would not be obscure the detection of $CD8^+$ cells in the liver or abdominal region. Further, no cross reactivity to background mouse tissues was observed (see FIG. 6C).

Figure 8A:
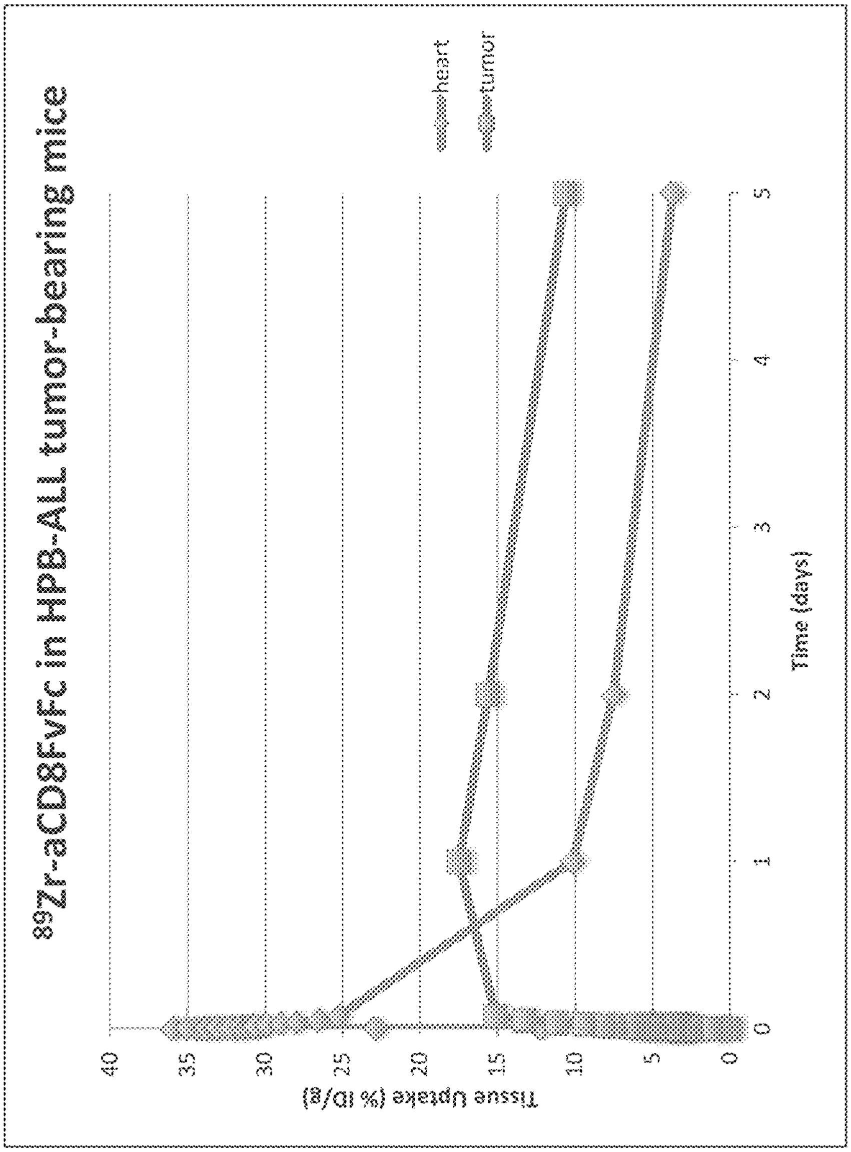
FIG. 8A shows the results of experiments that were performed to determine the amount of $^{89}$Zr-OA-CD8-FvFc present in tumor tissue and in the blood pool (heart content) in HPB-ALL-xenografted mice.
Figure 8B:
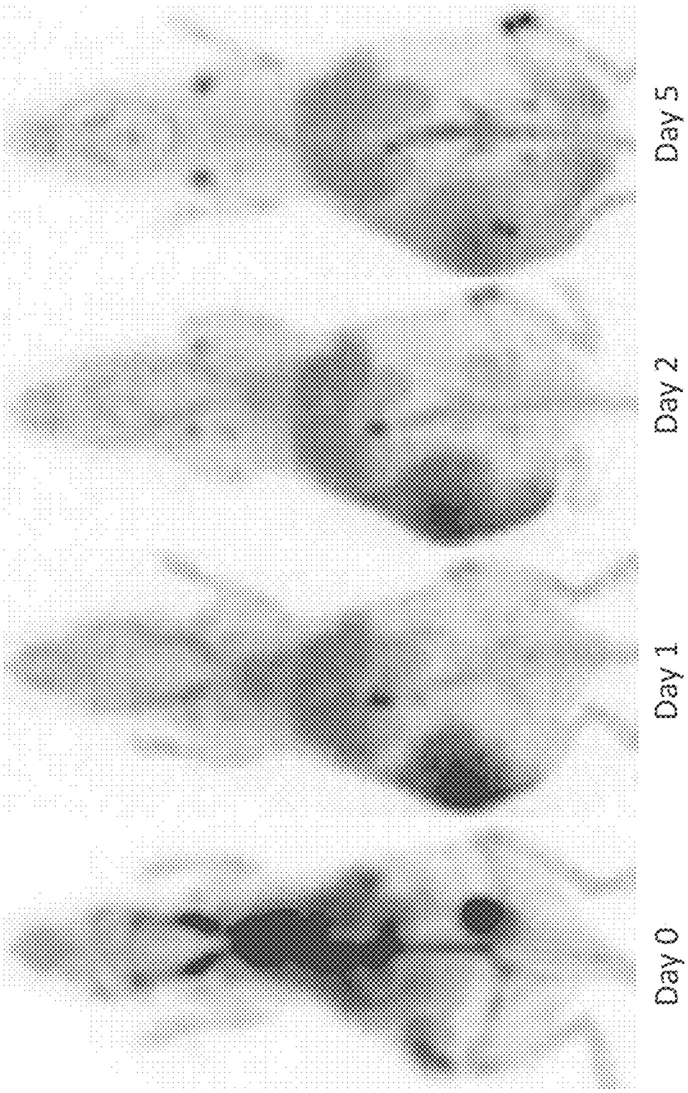
FIG. 8B shows PET MIPS of HPB-ALL tumor xenografted mice at Day 0, Day 1, Day 2, and Day 5 following injection with $^{89}$Zr-OA-CD8-FvFc.

$^{89}$Zr-OA-CD8-FvFc, i.e., a monovalent single chain Fc-Fv fusion, was also tested, as described above. $^{89}$Zr-OA-CD8-FvFc demonstrated uptake in $CD8^+$ tumor tissue, but not in heart tissue. See FIG. 8A. Peak uptake of $^{89}$Zr-OA-CD8-FvFc in tumor tissue comparable to that of $^{89}$Zr-huOKT8.v1-OA and $^{89}$Zr-huOKT8.v9-OA. However, clearance of $^{89}$Zr-OA-CD8-FvFc was dominated by the liver, rather than kidneys (see FIG. 8B), indicating that $^{89}$Zr-OA-CD8-FvFc may obscure detection of $CD8^+$ cells in the liver or abdominal region.

Example 4: Evaluation of the Sensitivity and Range of Detection of $^{89}$Zr-huOKT8.v11-19A-LALAPG in a Mouse Models As discussed above, huOKT8.v11 was reformatted as a one-armed IgG1 antibody comprising knob-in-hole mutations (i.e., T366S L358A Y407V in the "hole" heavy chain and T366W in the "knob" Fc), as well as the L234A, L235A, and P329G effector function mutations to produce huOKT8.v11-OA-LALAPG (see FIG. 1 for a schematic depiction). The sensitivity and range of detection of radiolabeled huOKT8.v11-OA-LALAPG was assessed in a series of immunoPET experiments using chimeric HPB-ALL/Daudi xenografts. Briefly, mice injected with a specified ratio of HPB-ALL cells and Daudi cells were shown to develop tumors that express CD8 at different levels, as shown Table 8:

TABLE 8

| Nomenclature for chimeric tumor | Starting Ratio of HPB-ALL/Daudi | % CD8 cells (determined via FACS) | [CD8], nM (approximate) |
|---|---|---|---|
| 100% HPB-ALL | 100/0 | ~97% | 67 ± 20 nM |
| 50% HPB-ALL | 50/50 | ~62% | 41 nM |
| 25% HPB-ALL | 25/75 | ~39% | 26 nM |
| 5% HPB-ALL | 05/95 | ~22% | 15 nM |
| 0% HPB-ALL | 0/100 | 0% | 0 nM |

Figure 9A:
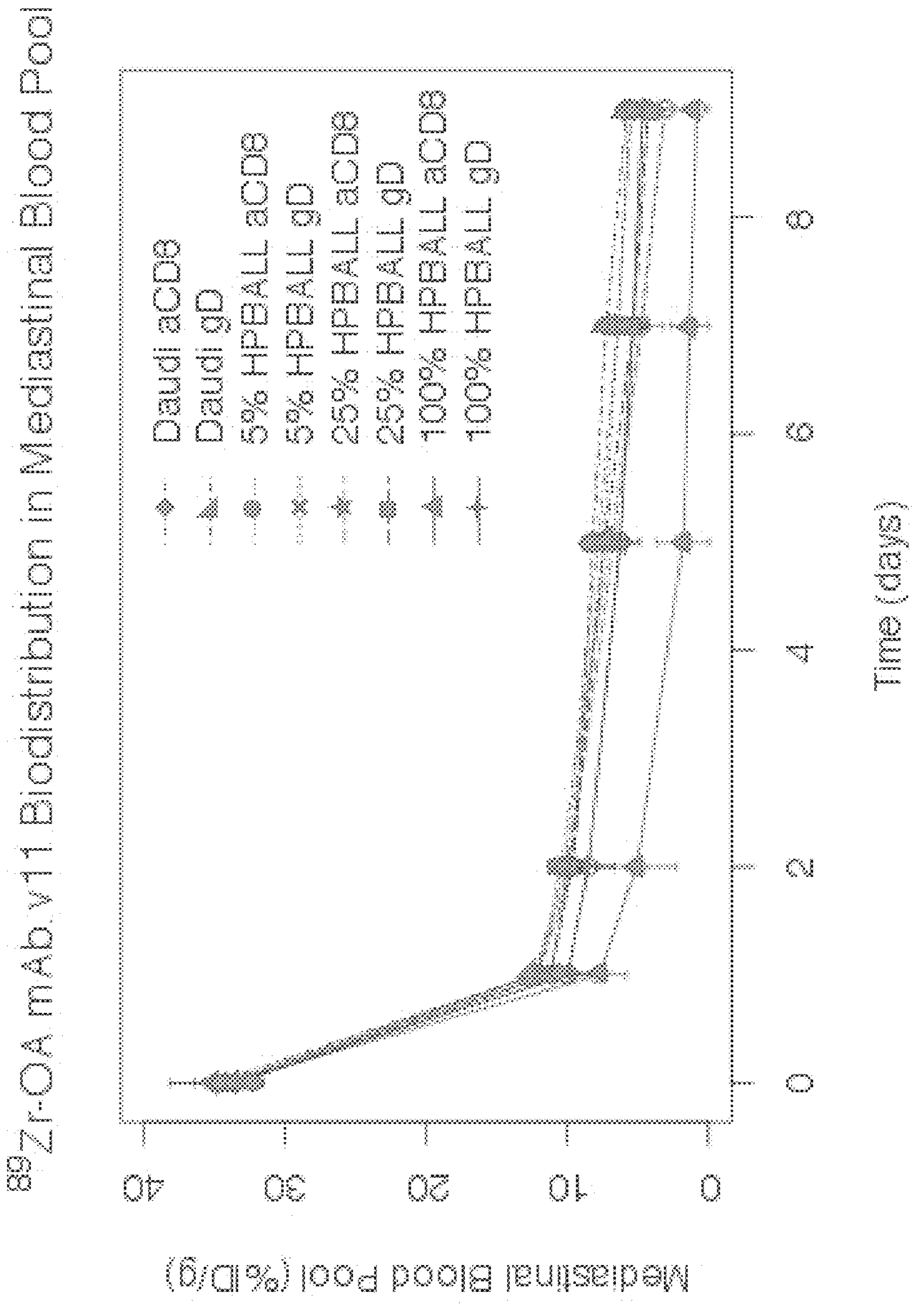
FIG. 9A shows the results of experiments that were performed to determine the amount of $^{89}$Zr-huOKT8.v11-OA or $^{89}$Zr-gD-OA in blood pools of mice bearing 100% HPB-ALL, 25% HPB-ALL, 5% HPB-ALL, or 0% HPB-ALL chimeric tumors.
Figure 9B:
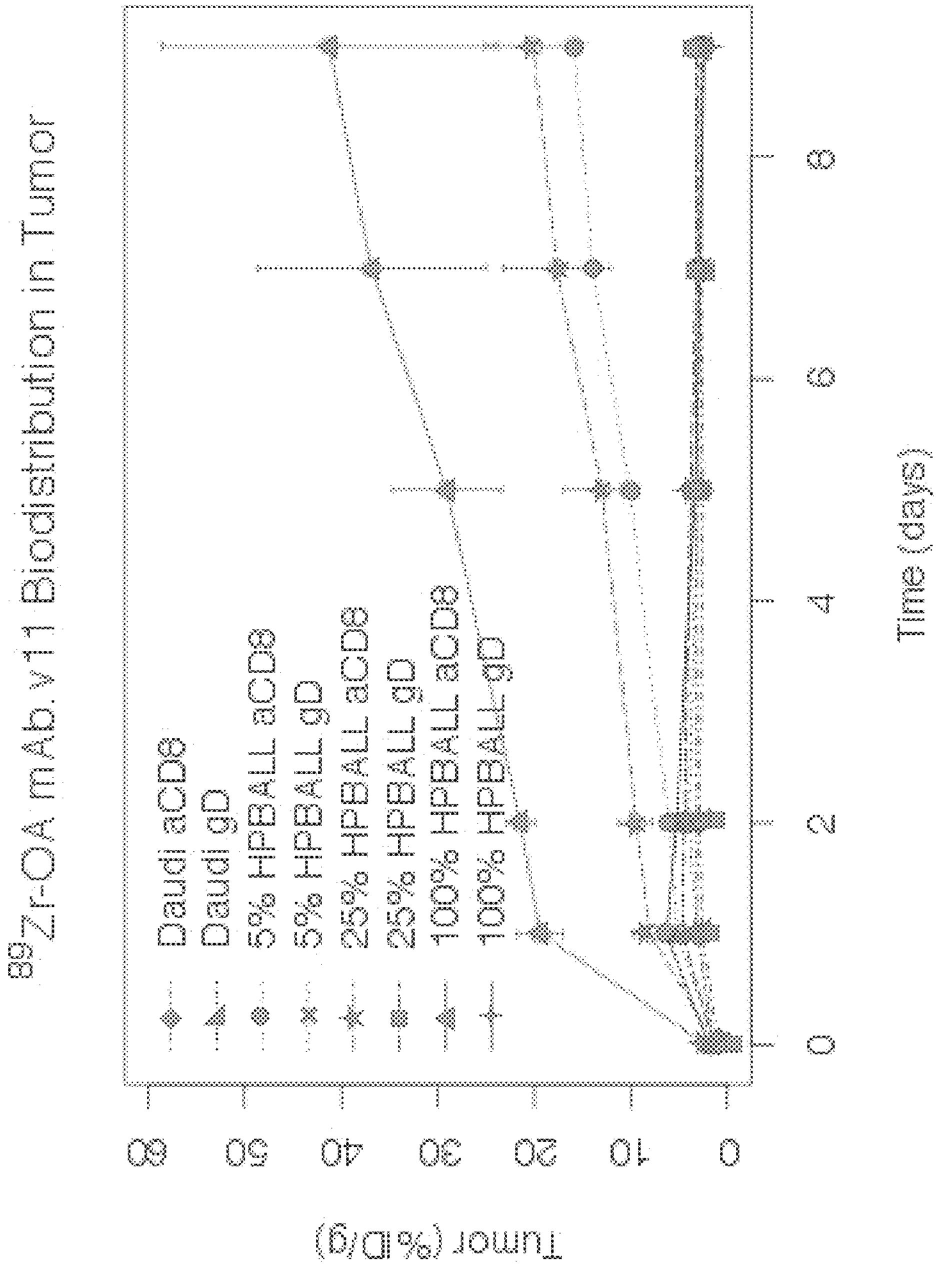
FIG. 9B shows the results of experiments that were performed to determine the amount of $^{89}$Zr-huOKT8.v11-OA or 89 Zr-gD-OA that was taken up by tumor tissue in mice bearing 100% HPB-ALL, 25% HPB-ALL, 5% HPB-ALL, or 0% HPB-ALL chimeric tumors.
Figure 9C:
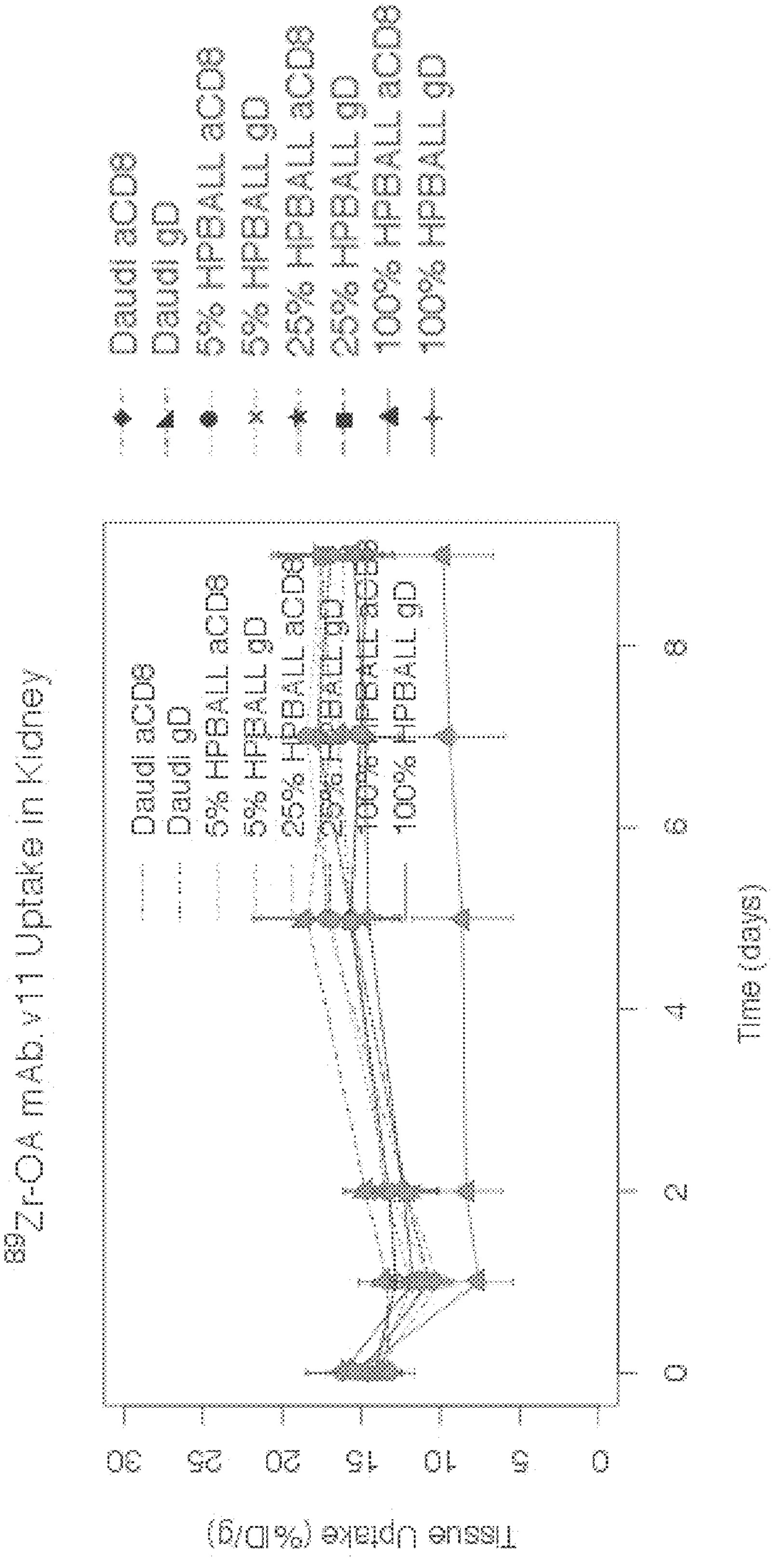
FIG. 9C shows the results of experiments that were performed to determine the amount of $^{89}$Zr-huOKT8.v11-OA or $^{89}$Zr-gD-OA that was taken up by kidney tissue in mice bearing 100% HPB-ALL, 25% HPB-ALL, 5% HPB-ALL, or 0% HPB-ALL chimeric tumors.
Figure 9D:
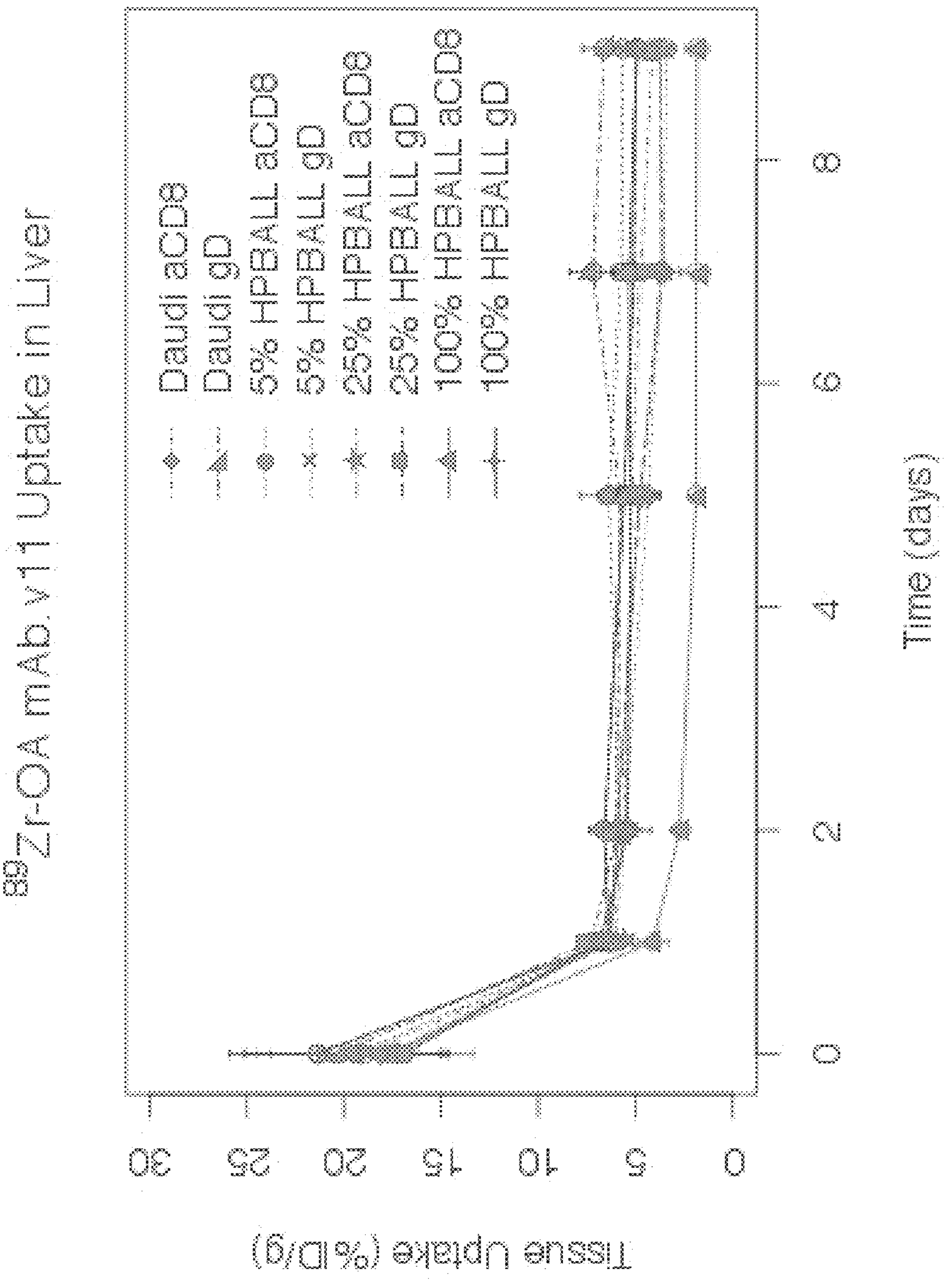
FIG. 9D shows the results of experiments that were performed to determine the amount of $^{89}$Zr-huOKT8.v11-OA or $^{89}$Zr-gD-OA that was taken up by liver tissue in mice bearing 100% HPB-ALL, 25% HPB-ALL, 5% HPB-ALL, or 0% HPB-ALL chimeric tumors.
Figure 9E:
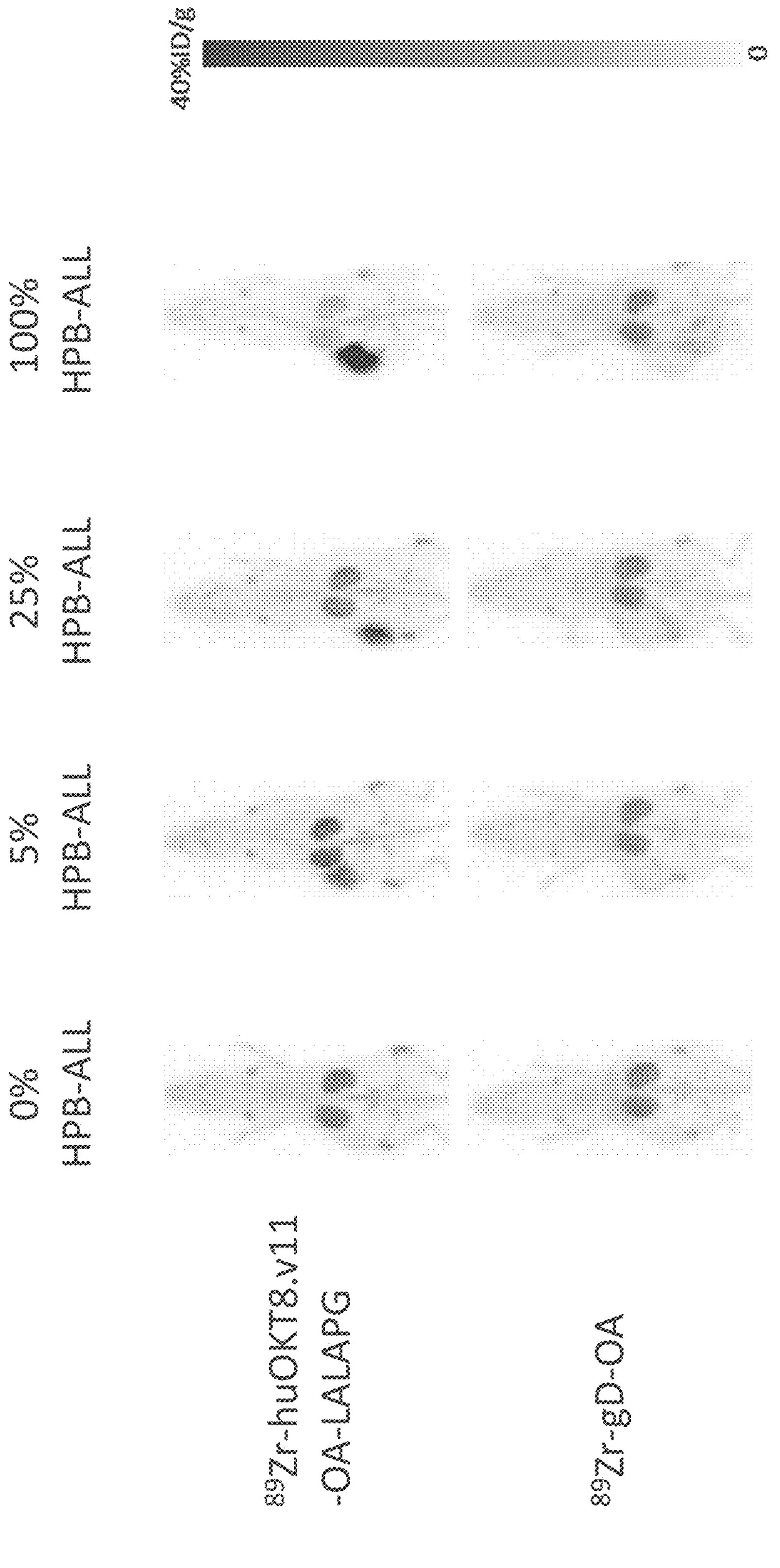
FIG. 9E provides PET images of mice bearing 100% HPB-ALL, 25% HPB-ALL, 5% HPB-ALL, or 0% HPB-ALL chimeric tumors that were injected with $^{89}$Zr-huOKT8.v11-OA-LALAPG or $^{89}$Zr-gD-OA. The PET scans were performed on Day 7 post-injection.

Mice bearing 100% HPB-ALL, 25% HPB-ALL, 5% HPB-ALL, or 0% HPB-ALL chimeric tumors (n=4/group) were injected with $^{89}$Zr-huOKT8.v11-OA-LALAPG or $^{89}$Zr-gD-OA. Following injection, the mice were monitored via PET scan at dosing, Day 1, Day 2, Day 5, Day 7, and Day 9 post initial dosing, and uptake of $^{89}$Zr-huOKT8.v11-OA-LALAPG or $^{89}$Zr-gD-OA into tumor tissue, liver tissue, kidney tissue, and in blood pools was measured. As shown in FIG. 9B, uptake of $^{89}$Zr-huOKT8.v11-OA-LALAPG into tumor tissue varied with the level of $CD8^+$ cells in the tumor tissue. Peak uptake of $^{89}$Zr-huOKT8.v11-OA-LALAPG was over 40% in 100% HPB-ALL tumors, about 20% in 25% HPB-ALL tumors, about 15% in 5% HPB-ALL tumors and 0% in 0% HPB-ALL tumors. Minimal uptake of $^{89}$Zr-gD-OA was detected in tissue of the chimeric tumors. Minimal $^{89}$Zr-huOKT8.v11-OA-LALAPG or $^{89}$Zr-gD-OA was detected in the blood of mice bearing chimeric HPB-ALL/Daudi tumors. See FIG. 9A. Moderate uptake of $^{9}$Zr-huOKT8.v11-OA-LALAPG and $^{89}$Zr-gD-OA was detected in kidney tissue of mice bearing chimeric HPB-ALL/Daudi tumors (see FIG. 9C), whereas minimal uptake of $^{89}$Zr-huOKT8.v11- and $^{89}$Zr-gD-OA was detected in liver tissue (see FIG. 9D). The results shown in FIGS. 9C and 9D indicate that clearance of $^{89}$Zr-huOKT8.v11-OA-LALAPG and $^{89}$Zr-gD-OA is dominated by the kidneys. FIG. 9E provides PET images of mice bearing 100% HPB-ALL, 25% HPB-ALL, 5% HPB-ALL, or 0% HPB-ALL chimeric tumors (n=4/group) that were injected with $^{89}$Zr-huOKT8.v11-OA-LALAPG or $^{89}$Zr-gD-OA. PET was performed on Day 7 post-injection. Taken together, the results shown in FIGS. 9A-9E demonstrate that a two-fold change in CD8 concentration can be measured using $^{89}$Zr-huOKT8.v11-OA-LALAPG.

Figure 10A:
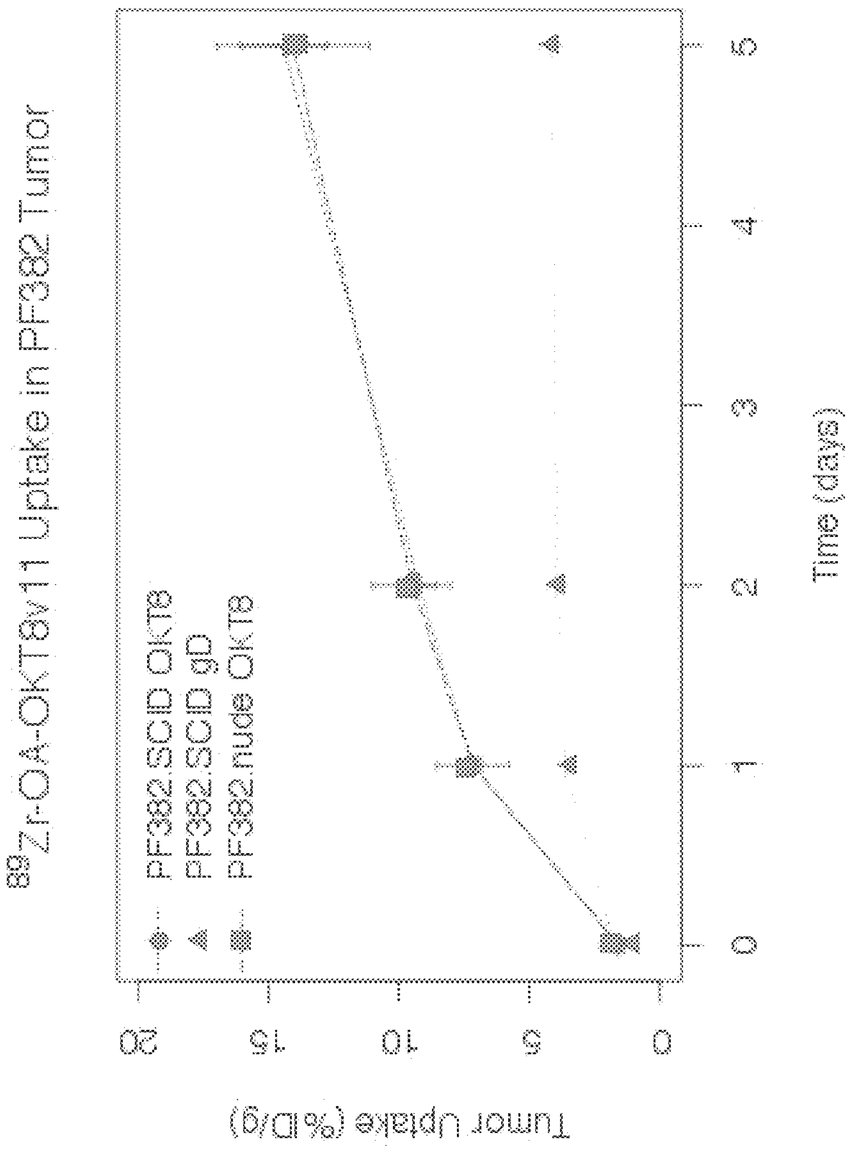
FIG. 10A shows the results of experiments that were performed to determine the amount of $^{89}$Zr-OA-CD8-FvFc that was taken up by tumor tissue in PF382-xenografted nude or SCID mice.
Figure 10B:
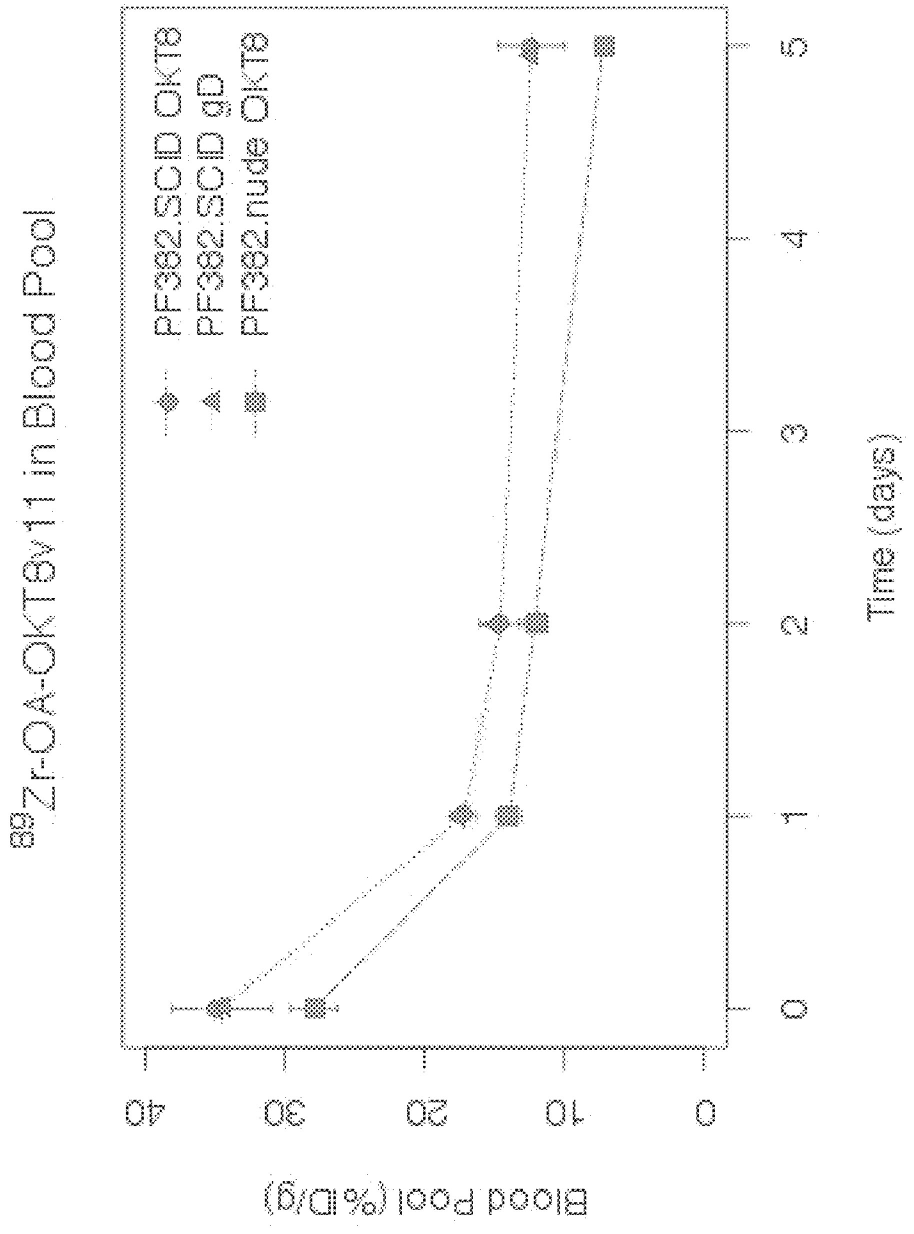
FIG. 10B shows the results of experiments that were performed to determine the amount of $^{89}$Zr-OA-CD8-FvFc in blood pools from PF382-xenografted nude or SCID mice.

Complementary experiments were performed in SCID and nude mice bearing PF382 (human T cell leukemia) xenografted tumors, which express CD8 at about 20% of the level of 100% HPB-ALL tumors. Mice (n=4/group) were injected with $^{89}$Zr-huOKT8.v11-OA-LALAPG or $^{89}$Zr-gD-OA and monitored via PET scan at dosing, Day 1, Day 2, Day 5, Day 7, and Day 9 post initial dosing. As shown in FIG. 10A, levels of $^{89}$Zr-huOKT8.v11-OA-LALAPG in PF382 tumor tissue from both SCID and nude xenografted mice increased as a function of time, with a peak uptake of ~15% at Day 5. By contrast, minimal uptake of $^{89}$Zr-gD-OA was detected in PF382 tumor tissue. Levels of $^{89}$Zr-huOKT8.v11-OA-LALAPG and $^{89}$Zr-gD-OA in blood pools decreased over time (see FIG. 10B).

Figure 11A:
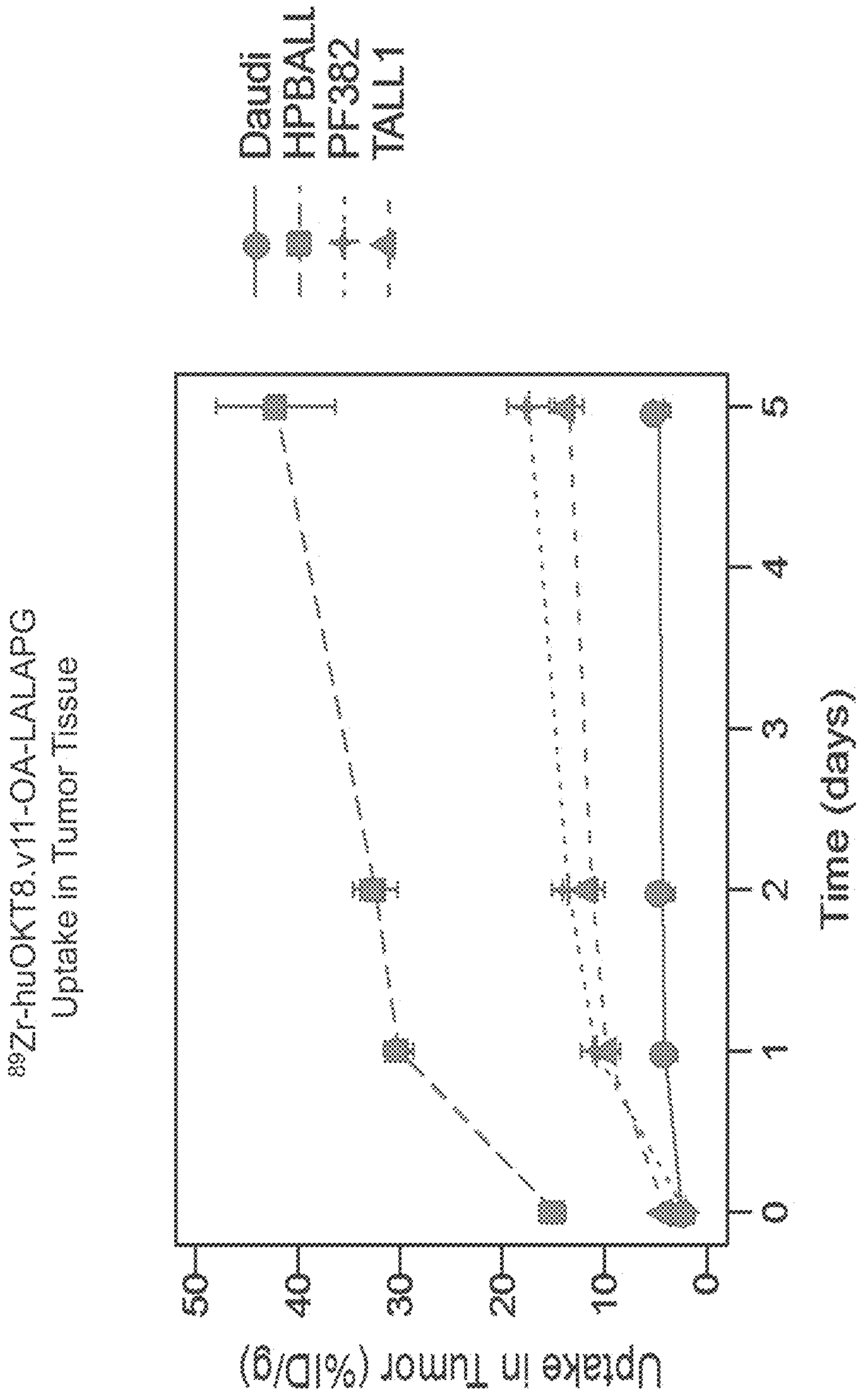
FIG. 11A provides a direct comparison of the uptake of $^{89}$Zr-huOKT8.v11-OA-LALAPG in HPB-ALL, PF382, TALL-1, and Daudi tumors in xenografted mice.
Figure 11B:
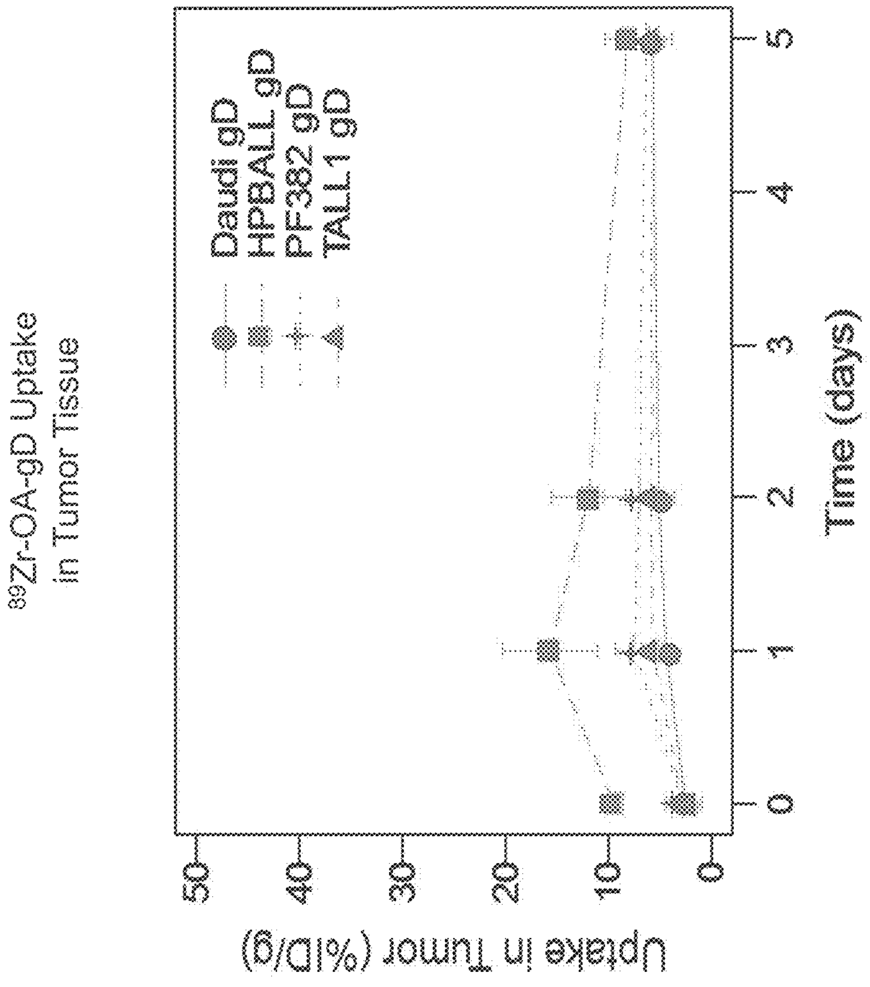
FIG. 11B provides a direct comparison of the uptake of $^{89}$Zr-gD-OA in HPB-ALL, PF382, TALL-1, and Daudi tumors in xenografted mice.
Figure 11C:
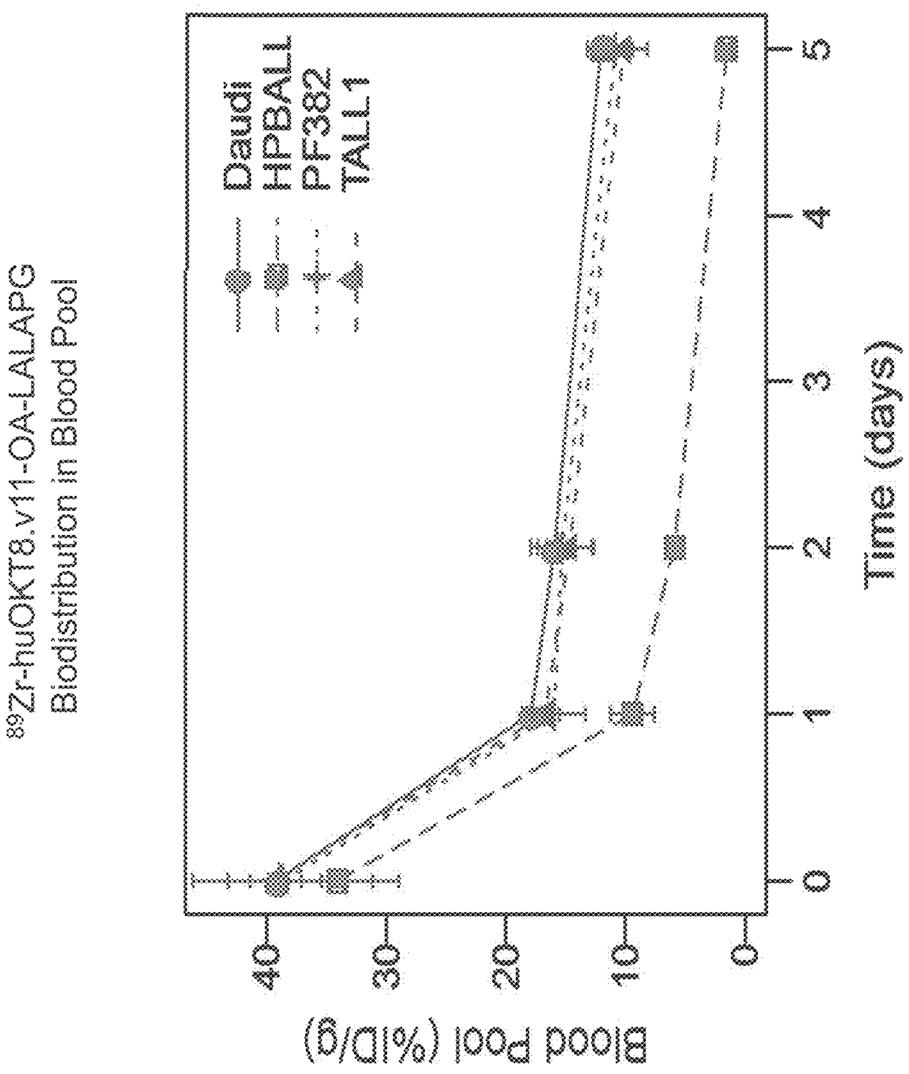
FIG. 11C provides a direct comparison of the amount of $^{89}$Zr-huOKT8.v11-OA-LALAPG in blood pools from mice bearing HPB-ALL, PF382, TALL-1, or Daudi tumors xenografts.
Figure 11D:
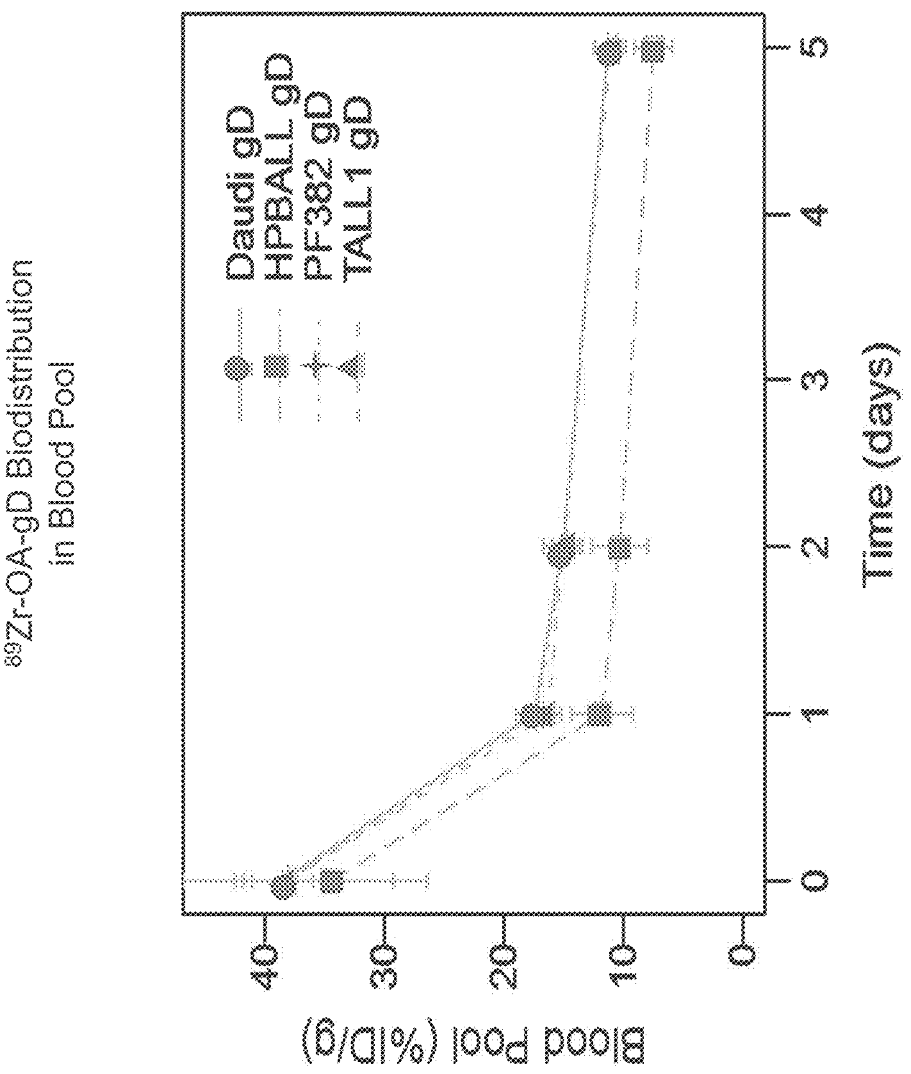
FIG. 11D provides a direct comparison of the amount of $^{89}$Zr-gD-OA in blood pools from mice bearing HPB-ALL, PF382, TALL-1, or Daudi tumors xenografts.

FIG. 11A provides a direct comparison of the uptake of $^{89}$Zr-huOKT8.v11-OA-LALAPG and $^{89}$Zr-gD-OA in HPB-ALL, PF382, TALL-1, and Daudi tumors in xenografted mice. CD8 levels in TALL-1 tumors are lower than those in PF382 tumors. Peak uptake of $^{89}$Zr-huOKT8.v11-OA-LALAPG was over 40% in HPB-ALL tumors, about 15% in PF382 tumors, about 12% in TALL-1 tumors, and less than 5% in Daudi tumors. Results of control experiments using $^{89}$Zr-gD-OA are shown in FIG. 11B. Levels of $^{89}$Zr-huOKT8.v11-OA-LALAPG and $^{89}$Zr-gD-OA in blood pools from xenografted mice were minimal and decreased over time (see FIGS. 11C and 11D).

Taken together, the results discussed above confirm that tissue CD8 concentrations can be measured with $^{89}$Zr-huOKT8.v11-OA-LALAPG.

Figure 12:
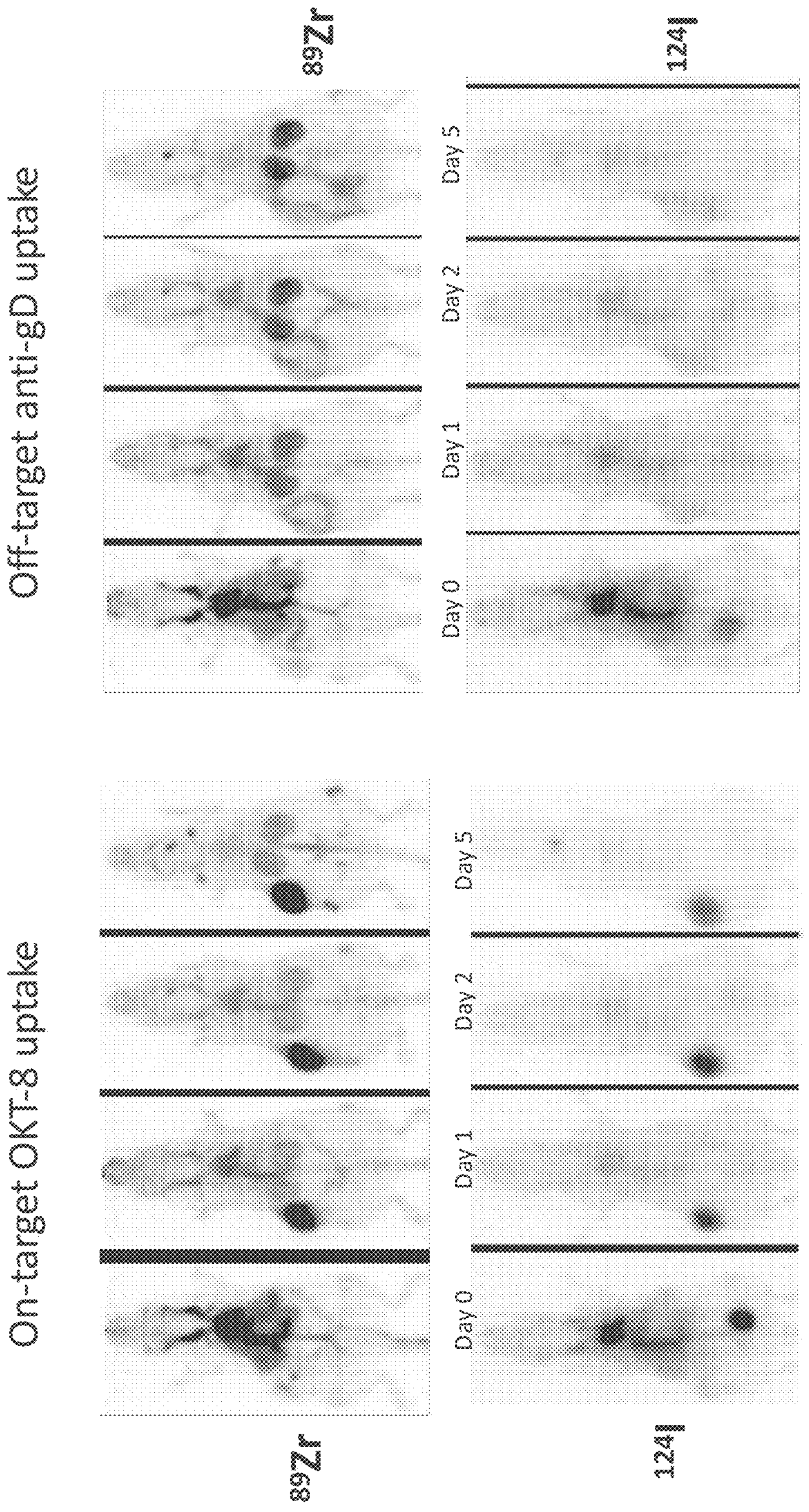
FIG. 12 shows the results of experiments that were performed to assess whether $^{89}$Zr-huOKT8.v11-OA-LALAPG or $^{124}$I-huOKT8.v11-OA-LALAPG were detectable in CD8$^{+}$ tumor tissue in HBP-ALL-xenografted mice.

Additional imaging experiments were performed on mice bearing HPB-ALL tumor xenografts using a $^{89}$Zr-labeled huOKT8.v17-based reagent or an $^{124}$I-labeled huOKT8.v17-based reagent. 3 mg/kg labeled antibody was administered to each mouse. Isotype control experiments in which HPB-ALL-xenografted mice were given 3 mg/kg $^{89}$Zr-gD or $^{124}$I-gD were performed in parallel. As shown in FIG. 12, both $^{89}$Zr-labeled huOKT8.v17 and $^{124}$I-labeled huOKT8.v17 were both detectable in $CD8^+$ tumor tissue. Less non-specific signal was observed in mice given $^{124}$I-labeled antibody.

Figure 13A:
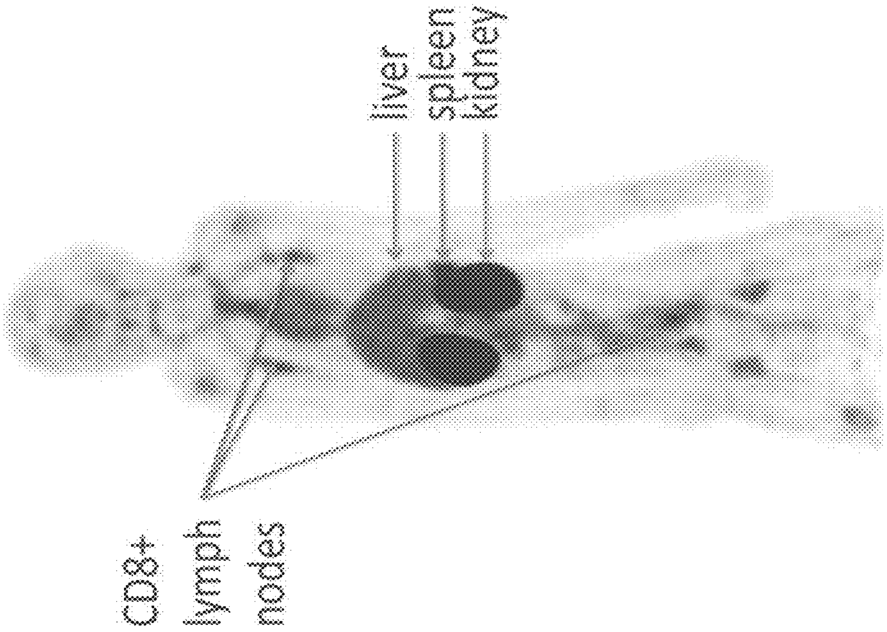
FIG. 13A shows a PET MIP image of a rhesus monkey on Day 7 post dosing with 2 mg/mg $^{89}$Zr-huOKT8.v11-OA-LALAPG.
Figure 13B:
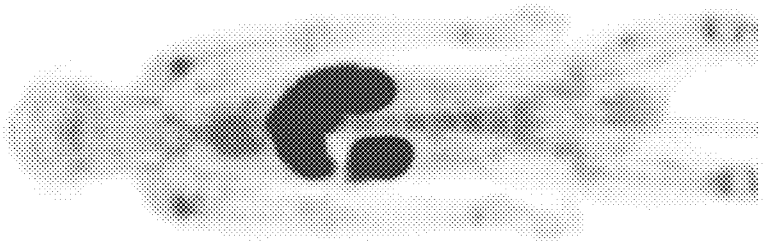
FIG. 13B shows a PET MIP image of a rhesus monkey on Day 7 post dosing with $^{89}$Zr-gD-OA.

Example 5: Molecular Imaging in Non-Human Primates with $^{89}$Zr-huOKT8.v11-OA-LALAPG Imaging experiments were performed with $^{89}$Zr-huOKT8.v11-OA-LALAPG in a rhesus monkey to determine whether uptake could be detected in tissues that are normally CD8-rich. A rhesus monkey (5 kg) was injected with 10 mg $^{89}$Zr-huOKT8.v11-OA-LALAPG containing a 1 mCi radiation dose. FIG. 13A shows a PET MIP image on Day 7 post initial dosing of 2 mg/kg. CD8-rich lymph nodes, spleen, and thymus can be visualized clearly. Clearance of $^{89}$Zr-huOKT8.v11-OA-LALAPG to the liver and kidney are also visible. By contrast, CD8-rich tissues are not visible in a PET MIP image on Day 5 following injection with $^{89}$Zr-gD-OA. (See FIG. 13B). Only clearance to the liver and kidneys can be seen.

Additional tissue distribution imaging experiments also performed in cynomolgous monkey, as summarized in Table 9, to find a dynamic range for imaging sensitivity.

TABLE 9

| Group | Number of Males | Test Material | Dose Level (mg/kg) | Dose Volume (mL) | Imaging PET/CT (hours) |
|---|---|---|---|---|---|
| 1 | 2 | $^{89}$Zr-huOKT8.v11-OA-LALAPG | 0.052 | 5 | 0, 24, 72, 120 |
| 2 | 2 | $^{89}$Zr-huOKT8.v11-OA-LALAPG | 0.23 | 5 | 0, 24, 72, 120 |
| 3 | 2 | $^{89}$Zr-gD-OA | 0.3 | 5 | 0, 24, 72, 120 |

Figure 14A:
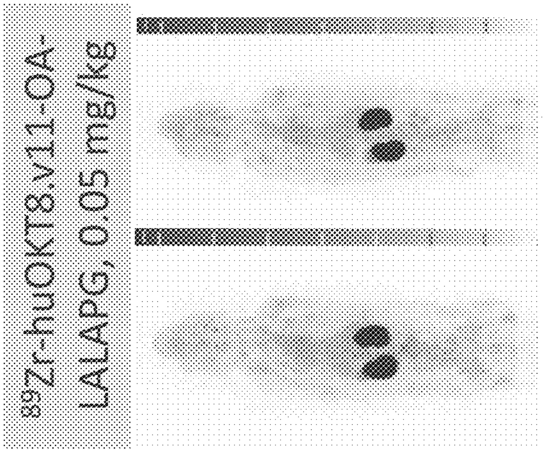
FIG. 14A provides a PET MIP image of a cynomolgous monkey on Day 5 post dosing with 0.05 mg/kg $^{89}$Zr-huOKT8.v11-OA-LALAPG.
Figure 14B:
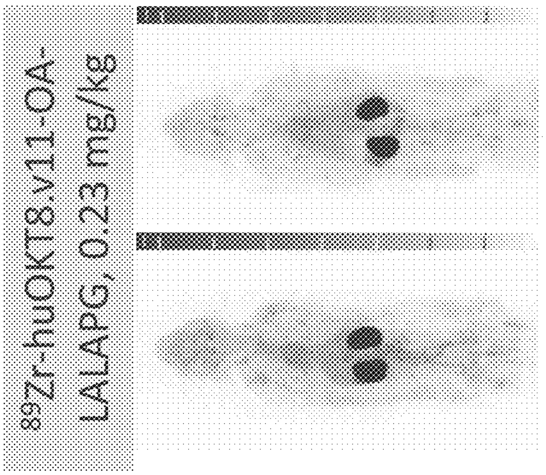
FIG. 14B shows a PET MIP image of a cynomolgous monkey on Day 5 post dosing with 0.23 mg/kg $^{89}$Zr-huOKT8.v11-OA-LALAPG.
Figure 14C:
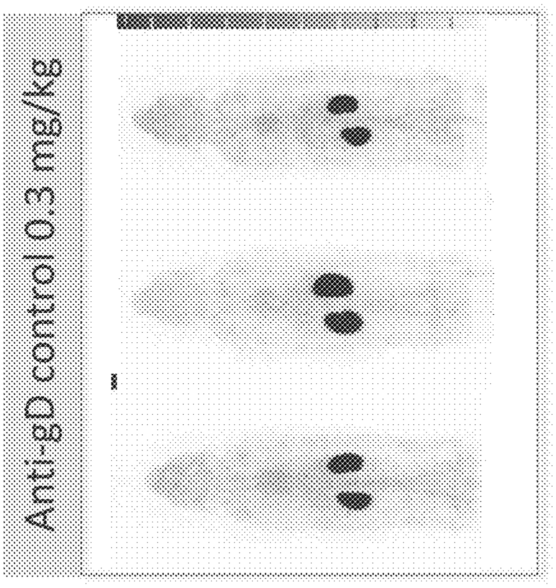
FIG. 14C shows a PET MIP image of a cynomolgous monkey on Day 3 post dosing with 0.33 mg/kg $^{89}$Zr-gD-OA.

PET MIP images on Day 5 post initial dosing for 0.05 mg/kg $^{89}$Zr-huOKT8.v11-OA-LALAPG, 0.23 mg/kg $^{89}$Zr-huOKT8.v11-OA-LALAPG, and $^{89}$Zr-gD-OA are provided in FIGS. 14A, 14B, and 14C, respectively. CD8-rich lymph nodes and spleen can be visualized using at the nominal doses of $^{89}$Zr-huOKT8.v11-OA-LALAPG used in FIGS. 14A and 14B. Such CD8-rich tissues are not visible in monkeys injected with 0.3 mg/kg $^{89}$Zr-gD-OA (see FIG. 14C).

Example 6: Pharmacokinetic and Toxicokinetic Analyses in Mice and Non-Human Primates Pharmacokinetic studies of huOKT8.v1-OA-LALAPG, huOKT8.v9-OA-LALAPG, and huOKT8.v11-OA-LALAPG were performed in mice. As shown in Table 10, Cmax, AUCinf, CL, half-life, and Vss were similar for all three variants.

TABLE 10

| Variant | Cmax (μg/ml) | AUCinf (day · μg/ml) | CL (mL/day/kg) | $t_{1/2}$ (day) | Vss (mL/kg) |
|---|---|---|---|---|---|
| huOKT8.v1-OA-LALAPG | 41.7 | 128 | 23.5 | 6.03 | 188 |
| huOKT8.v9-OA-LALAPG | 42.2 | 157 | 19.1 | 6.44 | 164 |
| huOKT8.v11-OA-LALAPG | 38.9 | 142 | 21.2 | 7.73 | 200 |

The results of further pharmacokinetic studies performed in cynomolgous monkeys are provided in Table 11 below:

TABLE 11

| Group | No. Males | Test material | Dose (mg/kg) | Cmax (μg/mL) | CL (mL/day/kg) | $t_{1/2}$ (day) | $V_1$ (mL/kg) |
|---|---|---|---|---|---|---|---|
| 1 | 2 | $^{89}$Zr-huOKT8.v11-OA-LALAPG | 0.05 (n = 2) | 1.1-1.4 | 14-16 | 2.61-3.35 | 60-62 |

TABLE 11-continued

| Group | No. Males | Test material | Dose (mg/kg) | Cmax (μg/mL) | CL (mL/day/kg) | $t_{1/2}$ (day) | $V_1$ (mL/kg) |
|---|---|---|---|---|---|---|---|
| 2 | 2 | $^{89}$Zr-huOKT8.v11-OA-LALAPG | 0.23 (n = 2) | 4.7-5.1 | 17 | 1.79-3.25 | 55-71 |
| 3 | 2 | $^{89}$Zr-huOKT8.v11-OA-LALAPG | 1 (n = 2) | 24-26 | 16 | 2.84-4.23 | 69-75 |

$^{89}$Zr-huOKT8.v11-OA-LALAPG demonstrated linear pharmacokinetics over a dose range of 0.05 mg/kg to 1 mg/kg. CL was ~15 mL/day/kg. No cytokine plasma level changes were observed.

Next, experiments were performed to evaluate the toxicity and toxicokinetics of unlabeled huOKT8.v11-OA-LALAPG (i.e., huOKT8.v11-OA-LALAPG comprising N-succinyl-desferrioxamine linkers) in cynomolgous monkeys. Unlabeled huOKT8.v11-OA-LALAPG was administered to the monkeys once on Days 1 and 15 via slow bolus intravenous injection at the dose levels and dose concentrations shown in Table 12:

TABLE 12

| Group | Number of Animals | | Dose Level* | Dose** concentration |
|---|---|---|---|---|
| | Male | Female | (mg/kg/dose) | (mg/mL) |
| Vehicle Control | 3 | 3 | 0 | 0 |
| LOW huOKT8.v11-OA-LALAPG | 3 | 3 | 30 | 6 |
| HIGH*** huOKT8.v11-OA-LALAPG | 3 | 3 | 100 | 20 |

*Animals were dosed at a volume of 5 mL/kg on Study Days 1 and 15 of the dosing phase for a total of two doses.

**Test article dose concentrations were based on nominal concentration of the test article as supplied (20 mg/mL).

***High doses were necessary to cover required safety factor (10×) and affinity compensation (13×).

huOKT8.v11-OA-LALAPG was well tolerated at concentrations of up to 100 mg/kg (i.e., the highest dose tested), indicating that the no observed effect level (NOAEL) is at least 100 mg/kg/dose. No effects of any of the safety endpoints measured were observed. Ten of the twelve monkeys dosed with huOKT8.v11-OA-LALAPG were positive for anti-drug antibodies (ADA).

Example 7: Human Pharmacokinetic Prediction and Safety Factor Estimates huOKT8.v11-OA-LALAPG is predicted to have a CL of ~6.3 mL/day/kg and a half-life of 10.4 days in humans, based on predictions from cynomolgous pharmacokinetic parameters by species-invariate time method with a fixed exponent of 0.85 for CL and 1.0 for volume of distribution. The predictions are based on an assumed body weight of ~70 kg for humans and ~3.0 kg for cynomolgous monkeys.

Additional predicted pharmacokinetic metrics for huOKT8.v11-OA-LALAPG in humans are provided in Table 13 below:

TABLE 13

| Proposed Dose Level | Proposed Dose (mg) | Proposed Dose (mg/kg) | Single-Dose Safety Factor Estimates HED* | Dose** | Cmax*** | AUC§ |
|---|---|---|---|---|---|---|
| Starting Dose | 1 | 0.014 | 2304 | 7143 | 7882 | 4664 |
| | 5 | 0.07 | 461 | 1429 | 1562 | 933 |
| Highest Dose | 20 | 0.28 | 115 | 357 | 392 | 233 |

NOAEL cyno = 100 mg/kg

*HED (mg/kg) = NHP dose/conversion factor of 3.1; thus $SP_{HED}$ = HED/$Dose_{human}$

**$SP_{dose}$ = $Dose_{cyno}$/$Dose_{human}$

***$SF_{Cmax}$ = $C_{max, cyno}$/$C_{max, human}$

§$SF_{AUC}$ = $AUC_{eyno}$/$AUC_{human}$

The predictions in Table 12 are based on cynomolgus monkey TK data in Example 6 using the species-invariant time method with an exponent of 0.85. The predictions are based on an assumed body weight of ~70 kg for humans and ~3.0 kg for cynomolgous monkeys. The dose and dose regimen for cynomolgous monkey=100 mg/kg; Q2W; the human dose regimen=Q3W. The safety factor estimates cover required safety factor (10×) and affinity compensation (13×).

Example 8: Methods of using CD8 Imaging for Microbiome Research and Immune Phernotype Identification An anti-CD8 antibody or other CD8 imaging moiety (e.g., described herein) can be used to assess tumor and lymph node infiltration by $CD8^+$ cells. Such imaging is used to identify immune phenotypes that underlie microbiome signatures predictive of patient prognosis and/or response to cancer immunotherapy.

Furthermore, the anti-CD8 antibodies or other CD8 imaging moiety (e.g., described herein) can be used to identify microbiome signatures that are associated with particular whole-body patterns in the biodistribution of $CD8^+$ T-cells. Such imaging is used to determine the prevalence of $CD8^+$ T-cells in tumors and other lymph nodes, for example. Such imaging is used to select the most robust microbiome biomarkers, even when the direct associations with outcome are noisy or weak.

Resident gut bacteria may affect patient responses to cancer immunotherapy. See, e.g., Gopalakrishnan et al. (2018) *Science.* 359(6371): 97-103. Accordingly, identifying key microbial strains associated with patient responsiveness to cancer immunotherapy may be useful for identifying appropriate treatment regimens for cancer patients. The anti-CD8 antibodies or other CD8 imaging moieties (e.g., as described herein) may be used to identify the microbiome profile(s) (e.g., gut flora composition(s)) that correlate with patient responsiveness to immunotherapy (e.g., an immunotherapy discussed herein).

Briefly, gut microbiome samples (e.g., fecal samples) are acquired from cancer patients who are to undergo immunotherapy (e.g., an immunotherapy described elsewhere herein). An anti-CD8 antibody or other CD8 imaging moiety (e.g., as described herein) is administered to each of the patients prior to their undergoing cancer immunotherapy, and tumor and lymph node infiltration by $CD8^+$ cells is assessed in each patient. Next, the patients each receive cancer immunotherapy (e.g., an immunotherapy described herein). The anti-CD8 antibody or other CD8 imaging moiety (e.g., as described herein) is administered to the patients again following the cancer immunotherapy, and tumor and lymph node infiltration by $CD8^+$ cells is assessed a second time in each patient. The level of CD8 infiltration in the patient's tumor(s) and lymph nodes following immunotherapy is assessed, and each patient's microbiome profile (e.g., the types of microbes, as well as the abundance of each type of microbe, present in the gut microbiome sample) is determined. The key microbial strains present in the gut microbiome samples of the patients who demonstrate $CD8^+$ T cell infiltration to the tumor(s) and lymph nodes are identified.

Following the identification of key microbial strains in patients who have $CD8^+$ T cell infiltration to the lymph nodes and/or tumor, a microbiome drug comprising the key microbial strains is made from donor stool obtained from such patients. The microbiome drug is administered to patients who do not demonstrate $CD8^+$ T cell infiltration into the lymph nodes or tumor. Alternatively, a FMT (fecal microbiota transplant) procedure is performed on patients who do not demonstrate $CD8^+$ T cell infiltration into the lymph nodes and/or tumor using donor stool collected from patients who demonstrate $CD8^+$ T cell infiltration to the lymph nodes and/or tumor. In certain embodiments, the FMT or microbiome drug transforms a patient who does not exhibit $CD8^+$ infiltration into the lymph nodes and/or tumor upon cancer immunotherapy into a patient who does respond to cancer immunotherapy.

In certain embodiments, CD8 imaging is performed on the patient who does not exhibit $CD8^+$ infiltration into the lymph nodes and/or tumor prior to FMT or prior to administration of the microbiome drug. Following FMT or administration of the microbiome drug, the patient receives immunotherapy. Following immunotherapy, imaging is performed on the patient in order to determine if the FMT or the microbiome drug results in increased $CD8^+$ infiltration into the lymph nodes and/or tumor. In certain embodiments, if increased $CD8^+$ infiltration is observed in response to the cancer immunotherapy treatment after FMT or other microbiome drug, then the FMT or other microbiome drug is considered to have been successful.

The CD8 imaging agent used in conjunction with microbiome research and discovery can be any anti-CD8 antibody disclosed herein (e.g., huOKT8v.1, huOKT8v.9, huOKT8v.10, huOKT8v.11, huOKT8v.12, huOKT8v.15, and huOKT8v.17).

In certain embodiments, the cancer immunotherapy is a checkpoint inhibitor. In certain embodiments, the cancer immunotherapy is a T-cell targeting therapy. In certain embodiments, the T-cell targeting therapy is a T-cell bispecific, trispecific, or multispecific antibody or antigen binding fragment thereof. In certain embodiments, the cancer immunotherapy is a NK cell targeting therapy. In certain embodiments, the NK cell targeting therapy is a bispecific, trispecific, or multispecific antibody or an antigen binding fragment thereof.

In certain embodiments, CD8 imaging using an anti-CD8 antibody or other CD8 imaging moiety (e.g., as described herein) can be used to assess tumor and lymph node $CD8^+$ infiltration before, during, and after administration of a checkpoint inhibitor or an immune modulating molecule, such as a CD16 or CD3 targeting moiety. Such imaging is used to determine microbiome biomarkers that are associated with efficacy of a checkpoint inhibitor or an immune modulating molecule, such as a CD16 or CD3 targeting moiety.

The checkpoint inhibitor as used in this example can be any checkpoint inhibitor. In certain embodiments, the checkpoint inhibitor is an anti-PD1 or an anti-PDL1 antibody. In certain embodiments, the checkpoint inhibitor is atezolizumab (Tecentriq®).

The immune modulating molecules can be any molecule that affects CD8 cell proliferation and infiltration. Examples include T-cell bispecific molecules such as antibodies that bind CD3 and a tumor associated antigen and molecules that bind CD16 and a tumor associated antigen.

Example 9: Methods of Using CD8 Imaging for Determining the Efficacy of Cancer Immunotherapies An anti-CD8 antibody or other CD8 imaging moiety (e.g., described herein) is used to assess tumor and lymph node infiltration by $CD8^+$ cells. Such imaging is used to identify immune phenotypes that are predictive of patient prognosis and/or response to cancer immunotherapy. Such imaging is used to determine the prevalence of $CD8^+$ T-cells in tumors and other lymph nodes, for example. Such imaging is used to select cancer immunotherapy agents or combination cancer agents that include one or more cancer immunotherapy agents.

In all embodiments disclosed herein, the cancer immunotherapy is, for example, any anti-PD1 agent or anti-PDL1 agent disclosed herein, such as monoclonal antibodies to treat cancer, bi-specific antibodies that bind to T cells and to a tumor associated protein, bi-specific antibodies that bind to NK cells and to a tumor associated protein, CAR-T cell therapies, non-specific cancer immunotherapies and adjuvants, and immune checkpoint inhibitors. Bispecific antibodies that bind to T cells and to a tumor associated protein include, for example anti-CD3 bispecific antibodies. Bispecific antibodies that bind to NK cells and to a tumor associated protein include, for example, anti-CD16 (FcgammaRIII) bispecific antibodies, anti-CD16A bispecific antibodies, anti-CD56 bispecific antibodies, anti-$NK_D46$ bispecific antibodies, and any other NK-cell binding bispecific antibodies.

In certain embodiments, CD8 imaging using an anti-CD8 antibody or other CD8 imaging moiety (e.g., as described herein) can be used for the treatment, diagnosis, prognosis, companion diagnostic, and monitoring the progression/remission of cancer as described herein.

The Examples are offered for illustrative purposes only, and are not intended to limit the scope of the present invention in any way. Indeed, various modifications in addition to those shown and described herein will become apparent to those skilled in the art from the foregoing description and fall within the scope of the appended claims.

The invention claimed is:

1. One or more nucleic acid(s) encoding an anti-CD8 antibody that binds human CD8 and does not stimulate or inhibit the activation of CD8+ T cells, wherein the antibody is a monovalent antibody comprising an antibody heavy chain comprising a first Fc domain, an antibody light chain, and a second Fc domain, wherein the antibody heavy chain pairs with the antibody light chain, and wherein the first Fc domain and the second Fc domain form a dimer, wherein the first Fc domain comprises a cavity, and wherein the second Fc domain comprises a protuberance which is positionable in the cavity in the first Fc domain or wherein the second Fc domain comprises a cavity, and wherein the first Fc domain comprises a protuberance which is positionable in the cavity in the second Fc domain, and wherein the anti-CD8 antibody comprises:

(a) a heavy chain variable domain set forth in SEQ ID NO: 14; and a light chain variable domain set forth in SEQ ID NO: 15

(b) a heavy chain variable domain comprising (1) a CDR-H1 comprising the amino acid sequence set forth in SEQ ID NO: 9; (2) a CDR-H2 comprising the amino acid sequence set forth in SEQ ID NO: 10; and (3) a CDR-H3 comprising the amino acid sequence set forth in SEQ ID NO: 12; and a light chain variable domain comprising (1) a CDR-L1 comprising the amino acid sequence set forth in SEQ ID NO: 1; (2) a CDR-L2 comprising the amino acid sequence set forth in SEQ ID NO: 3; and (3) a CDR-L3 comprising the amino acid sequence set forth in SEQ ID NO: 5;

(c) a heavy chain variable domain comprising (1) a CDR-H1 comprising the amino acid sequence set forth in SEQ ID NO: 9; (2) a CDR-H2 comprising the amino acid sequence set forth in SEQ ID NO: 10; and (3) a CDR-H3 comprising the amino acid sequence set forth in SEQ ID NO: 12; and a light chain variable domain comprising (1) a CDR-L1 comprising the amino acid sequence set forth in SEQ ID NO: 1; (2) a CDR-L2 comprising the amino acid sequence set forth in SEQ ID NO: 3; and (3) a CDR-L3 comprising the amino acid sequence set forth in SEQ ID NO: 6;

(d) a heavy chain variable domain comprising (1) a CDR-H1 comprising the amino acid sequence set forth in SEQ ID NO: 9; (2) a CDR-H2 comprising the amino acid sequence set forth in SEQ ID NO: 10; and (3) a CDR-H3 comprising the amino acid sequence set forth in SEQ ID NO: 12; and a light chain variable domain comprising (1) a CDR-L1 comprising the amino acid sequence set forth in SEQ ID NO: 1; (2) a CDR-L2 comprising the amino acid sequence set forth in SEQ ID NO: 3; and (3) a CDR-L3 comprising the amino acid sequence set forth in SEQ ID NO: 7;

(e) a heavy chain variable domain comprising (1) a CDR-H1 comprising the amino acid sequence set forth in SEQ ID NO: 9; (2) a CDR-H2 comprising the amino acid sequence set forth in SEQ ID NO: 10; and (3) a CDR-H3 comprising the amino acid sequence set forth in SEQ ID NO: 12; and a light chain variable domain comprising (1) a CDR-L1 comprising the amino acid sequence set forth in SEQ ID NO: 1; (2) a CDR-L2 comprising the amino acid sequence set forth in SEQ ID NO: 3; and (3) a CDR-L3 comprising the amino acid sequence set forth in SEQ ID NO: 8;

(f) a heavy chain variable domain comprising (1) a CDR-H1 comprising the amino acid sequence set forth in SEQ ID NO: 9; (2) a CDR-H2 comprising the amino acid sequence set forth in SEQ ID NO: 11; and (3) a CDR-H3 comprising the amino acid sequence set forth in SEQ ID NO: 13; and a light chain variable domain comprising (1) a CDR-L1 comprising the amino acid sequence set forth in SEQ ID NO: 1; (2) a CDR-L2 comprising the amino acid sequence set forth in SEQ ID NO: 3; and (3) a CDR-L3 comprising the amino acid sequence set forth in SEQ ID NO: 8; or (g) a heavy chain variable domain comprising (1) a CDR-H1 comprising the amino acid sequence set forth in SEQ ID NO: 9; (2) a CDR-H2 comprising the amino acid sequence set forth in SEQ ID NO: 10; and (3) a CDR-H3 comprising the amino acid sequence set forth in SEQ ID NO: 12; and a light chain variable domain comprising (1) a CDR-L1 comprising the amino acid sequence set forth in SEQ ID NO: 2; (2) a CDR-L2 comprising the amino acid sequence set forth in SEQ ID NO: 3; and (3) a CDR-L3 comprising the amino acid sequence set forth in SEQ ID NO: 8.

2. An expression vector comprising the one or more nucleic acid(s) of claim 1.

3. A host cell comprising the one or more nucleic acid(s) of claim 1.

4. A method of making an anti-CD8 antibody, the method comprising: a) culturing the host cell of claim 3 under conditions where the antibody is produced; and b) recovering the anti-CD8 antibody produced by the host cell.

5. The method of claim 4, wherein the host cell is a eukaryotic cell.

6. The method of claim 5, wherein the eukaryotic cell is a CHO cell.

7. The method of claim 4, wherein the host cell is a prokaryotic cell.

8. The method of claim 7, wherein the prokaryotic cell is an *E. coli* cell.

9. The one or more nucleic acid(s) of claim 1, wherein the anti-CD8 antibody:

(a) does not induce $CD8^+$ T cell proliferation;
(b) does not induce IFN-γ production by $CD8^+$ T cells;
(c) does not bind $CD4^+$ T cells;
(d) does not bind CD3 cells; and
(e) does not deplete $CD8^+$ T cells from circulation.

10. The one or more nucleic acid(s) of claim 1, wherein the antibody is a chimeric antibody or a humanized antibody.

11. The one or more nucleic acid(s) of claim 1, wherein:

(a) the first Fc domain comprises T366S, L368A, and Y407V mutations, wherein the second Fc domain comprises a T366W mutation, and wherein the amino acid residues are numbered according to the EU numbering system; or (b) wherein the first Fc domain comprises a T366W mutation, wherein the second domain comprises T366S, L368A, and Y407V mutations, and wherein the amino acid residues are numbered according to the EU numbering system.

12. The one or more nucleic acid(s) of claim 1, wherein the anti-CD8 antibody comprises a human IgG constant region.

13. The one or more nucleic acid(s) of claim 12, wherein the IgG antibody is an IgG1 antibody.

14. The one or more nucleic acid(s) of claim 1, wherein the first and second Fc domains comprise L234A and L235A mutations and/or a P329G mutation, wherein amino acid residues are numbered according to the EU numbering system.

15. The one or more nucleic acid(s) of claim 1, wherein the anti-CD8 antibody:

(a) binds to human CD8 with a $K_D$ of less than about 10 nM;
(b) binds to cynomolgus CD8 with a $K_D$ of less than about 200 nM; and
(c) binds to rhesus CD8 with a $K_D$ of less than about 200 nM.

16. The one or more nucleic acid(s) of claim 1, wherein the anti-CD8 antibody does not bind mouse CD8 or rat CD8.

17. One or more nucleic acid(s) encoding an anti-CD8 antibody that binds human CD8 and does not stimulate or inhibit the activation of $CD8^+$ T cells, wherein the antibody is a monovalent antibody comprising an antibody heavy chain comprising a first Fc domain, an antibody light chain, and a second Fc domain, wherein the antibody heavy chain pairs with the antibody light chain, and wherein the first Fc domain and the second Fc domain form a dimer, wherein the first Fc domain comprises a cavity, and wherein the second Fc domain comprises a protuberance which is positionable in the cavity in the first Fc domain or wherein the second Fc domain comprises a cavity, and wherein the first Fc domain comprises a protuberance which is positionable in the cavity in the second Fc domain, and wherein the anti-CD8 antibody comprises:

(a) a heavy chain variable domain set forth in SEQ ID NO: 16; and a light chain variable domain set forth in SEQ ID NO: 17;

(b) a heavy chain variable domain set forth in SEQ ID NO: 18; and a light chain variable domain set forth in SEQ ID NO: 19;

(c) a heavy chain variable domain set forth in SEQ ID NO: 20; and a light chain variable domain set forth in SEQ ID NO: 21;

(d) a heavy chain variable domain set forth in SEQ ID NO: 22; and a light chain variable domain set forth in SEQ ID NO: 23;

(e) a heavy chain variable domain set forth in SEQ ID NO: 24; and a light chain variable domain set forth in SEQ ID NO: 25; or (f) a heavy chain variable domain set forth in SEQ ID NO: 26; and a light chain variable domain set forth in SEQ ID NO: 27.

18. An expression vector comprising the one or more nucleic acid(s) of claim 17.

19. A host cell comprising the one or more nucleic acid(s) of claim 17.

20. A method of making an anti-CD8 antibody, the method comprising: a) culturing the host cell of claim 19 under conditions where the antibody is produced; and b) recovering the anti-CD8 antibody produced by the host cell.

* * * * *

SEQUENCE LISTING

```
Sequence total quantity: 33
SEQ ID NO: 1            moltype = AA  length = 5
FEATURE                 Location/Qualifiers
REGION                  1..5
                        note = Synthetic Construct
source                  1..5
                        mol_type = protein
                        organism = synthetic construct
SEQUENCE: 1
SISQY                                                                5

SEQ ID NO: 2            moltype = AA  length = 5
FEATURE                 Location/Qualifiers
REGION                  1..5
                        note = Synthetic Construct
source                  1..5
                        mol_type = protein
                        organism = synthetic construct
SEQUENCE: 2
SISKY                                                                5

SEQ ID NO: 3            moltype = AA  length = 6
FEATURE                 Location/Qualifiers
REGION                  1..6
                        note = Synthetic Construct
source                  1..6
                        mol_type = protein
                        organism = synthetic construct
SEQUENCE: 3
SGSTLQ                                                               6

SEQ ID NO: 4            moltype = AA  length = 6
FEATURE                 Location/Qualifiers
REGION                  1..6
                        note = Synthetic Construct
source                  1..6
                        mol_type = protein
                        organism = synthetic construct
SEQUENCE: 4
HNENPL                                                               6

SEQ ID NO: 5            moltype = AA  length = 6
FEATURE                 Location/Qualifiers
REGION                  1..6
                        note = Synthetic Construct
source                  1..6
                        mol_type = protein
                        organism = synthetic construct
SEQUENCE: 5
HNEFPV                                                               6

SEQ ID NO: 6            moltype = AA  length = 6
FEATURE                 Location/Qualifiers
REGION                  1..6
                        note = Synthetic Construct
source                  1..6
                        mol_type = protein
                        organism = synthetic construct
SEQUENCE: 6
HNEFPP                                                               6

SEQ ID NO: 7            moltype = AA  length = 6
FEATURE                 Location/Qualifiers
REGION                  1..6
                        note = Synthetic Construct
source                  1..6
                        mol_type = protein
                        organism = synthetic construct
SEQUENCE: 7
VNEFPP                                                               6

SEQ ID NO: 8            moltype = AA  length = 6
FEATURE                 Location/Qualifiers
REGION                  1..6
                        note = Synthetic Construct
source                  1..6
                        mol_type = protein
                        organism = synthetic construct
```

```
SEQUENCE: 8
VNEFPV                                                              6

SEQ ID NO: 9            moltype = AA  length = 10
FEATURE                 Location/Qualifiers
REGION                  1..10
                        note = Synthetic Construct
source                  1..10
                        mol_type = protein
                        organism = synthetic construct
SEQUENCE: 9
GFNIKDTYIH                                                          10

SEQ ID NO: 10           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 10
RIDPANDNTL YASKFQG                                                  17

SEQ ID NO: 11           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 11
RIDPANDNTL YARKFQG                                                  17

SEQ ID NO: 12           moltype = AA  length = 11
FEATURE                 Location/Qualifiers
REGION                  1..11
                        note = Synthetic Construct
source                  1..11
                        mol_type = protein
                        organism = synthetic construct
SEQUENCE: 12
GRGYGYYVFD H                                                        11

SEQ ID NO: 13           moltype = AA  length = 11
FEATURE                 Location/Qualifiers
REGION                  1..11
                        note = Synthetic Construct
source                  1..11
                        mol_type = protein
                        organism = synthetic construct
SEQUENCE: 13
TRGYGYYVFD T                                                        11

SEQ ID NO: 14           moltype = AA  length = 118
FEATURE                 Location/Qualifiers
REGION                  1..118
                        note = Synthetic Construct
source                  1..118
                        mol_type = protein
                        organism = synthetic construct
SEQUENCE: 14
EVQLVQSGAE VKKPGASVKV SCKASGFNIK DTYIHWVRQA PGQGLEWIGR IDPANDNTLY  60
ASKFQGRATI TADTSTSTAY LELSSLRSED TAVYYCGRGY GYYVFDHWGQ GTLVTVSS    118

SEQ ID NO: 15           moltype = AA  length = 107
FEATURE                 Location/Qualifiers
REGION                  1..107
                        note = Synthetic Construct
source                  1..107
                        mol_type = protein
                        organism = synthetic construct
SEQUENCE: 15
DVQITQSPSS LSASVGDRVT ITCRTSRSIS QYLAWYQEKP GKTNKLLIYS GSTLQSGIPS  60
RFSGSGSGTD FTLTISSLQP EDFATYYCQQ HNENPLTFGQ GTKVEIK                107

SEQ ID NO: 16           moltype = AA  length = 226
FEATURE                 Location/Qualifiers
REGION                  1..226
                        note = Synthetic Construct
```

```
source                  1..226
                        mol_type = protein
                        organism = synthetic construct
SEQUENCE: 16
EVQLVQSGAE VKKPGASVKV SCKASGFNIK DTYIHWVRQA PGQGLEWIGR IDPANDNTLY  60
ASKFQGRATI TADTSTSTAY LELSSLRSED TAVYYCGRGY GYYVFDHWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHT                 226

SEQ ID NO: 17           moltype = AA  length = 214
FEATURE                 Location/Qualifiers
REGION                  1..214
                        note = Synthetic Construct
source                  1..214
                        mol_type = protein
                        organism = synthetic construct
SEQUENCE: 17
DVQITQSPSS LSASVGDRVT ITCRTSRSIS QYLAWYQEKP GKTNKLLIYS GSTLQSGIPS  60
RFSGSGSGTD FTLTISSLQP EDFATYYCQQ HNEFPVTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 18           moltype = AA  length = 226
FEATURE                 Location/Qualifiers
REGION                  1..226
                        note = Synthetic Construct
source                  1..226
                        mol_type = protein
                        organism = synthetic construct
SEQUENCE: 18
EVQLVQSGAE VKKPGASVKV SCKASGFNIK DTYIHWVRQA PGQGLEWIGR IDPANDNTLY  60
ASKFQGRATI TADTSTSTAY LELSSLRSED TAVYYCGRGY GYYVFDHWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHT                 226

SEQ ID NO: 19           moltype = AA  length = 214
FEATURE                 Location/Qualifiers
REGION                  1..214
                        note = Synthetic Construct
source                  1..214
                        mol_type = protein
                        organism = synthetic construct
SEQUENCE: 19
DVQITQSPSS LSASVGDRVT ITCRTSRSIS QYLAWYQEKP GKTNKLLIYS GSTLQSGIPS  60
RFSGSGSGTD FTLTISSLQP EDFATYYCQQ HNEFPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 20           moltype = AA  length = 226
FEATURE                 Location/Qualifiers
REGION                  1..226
                        note = Synthetic Construct
source                  1..226
                        mol_type = protein
                        organism = synthetic construct
SEQUENCE: 20
EVQLVQSGAE VKKPGASVKV SCKASGFNIK DTYIHWVRQA PGQGLEWIGR IDPANDNTLY  60
ASKFQGRATI TADTSTSTAY LELSSLRSED TAVYYCGRGY GYYVFDHWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHT                 226

SEQ ID NO: 21           moltype = AA  length = 214
FEATURE                 Location/Qualifiers
REGION                  1..214
                        note = Synthetic Construct
source                  1..214
                        mol_type = protein
                        organism = synthetic construct
SEQUENCE: 21
DVQITQSPSS LSASVGDRVT ITCRTSRSIS QYLAWYQEKP GKTNKLLIYS GSTLQSGIPS  60
RFSGSGSGTD FTLTISSLQP EDFATYYCQQ VNEFPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 22           moltype = AA  length = 118
FEATURE                 Location/Qualifiers
REGION                  1..118
                        note = Synthetic Construct
source                  1..118
```

```
                        mol_type = protein
                        organism = synthetic construct
SEQUENCE: 22
EVQLVQSGAE VKKPGASVKV SCKASGFNIK DTYIHWVRQA PGQGLEWIGR IDPANDNTLY  60
ASKFQGRATI TADTSTSTAY LELSSLRSED TAVYYCGRGY GYYVFDHWGQ GTLVTVSS    118

SEQ ID NO: 23           moltype = AA  length = 107
FEATURE                 Location/Qualifiers
REGION                  1..107
                        note = Synthetic Construct
source                  1..107
                        mol_type = protein
                        organism = synthetic construct
SEQUENCE: 23
DVQITQSPSS LSASVGDRVT ITCRTSRSIS QYLAWYQEKP GKTNKLLIYS GSTLQSGIPS  60
RFSGSGSGTD FTLTISSLQP EDFATYYCQQ VNEFPVTFGQ GTKVEIK                107

SEQ ID NO: 24           moltype = AA  length = 226
FEATURE                 Location/Qualifiers
REGION                  1..226
                        note = Synthetic Construct
source                  1..226
                        mol_type = protein
                        organism = synthetic construct
SEQUENCE: 24
EVQLVQSGAE VKKPGASVKV SCKASGFNIK DTYIHWVRQA PGQGLEWIGR IDPANDNTLY  60
ARKFQGRATI TADTSTSTAY LELSSLRSED TAVYYCTRGY GYYVFDTWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHT                 226

SEQ ID NO: 25           moltype = AA  length = 214
FEATURE                 Location/Qualifiers
REGION                  1..214
                        note = Synthetic Construct
source                  1..214
                        mol_type = protein
                        organism = synthetic construct
SEQUENCE: 25
DVQITQSPSS LSASVGDRVT ITCRTSRSIS QYLAWYQEKP GKTNKLLIYS GSTLQSGIPS  60
RFSGSGSGTD FTLTISSLQP EDFATYYCQQ VNEFPVTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 26           moltype = AA  length = 226
FEATURE                 Location/Qualifiers
REGION                  1..226
                        note = Synthetic Construct
source                  1..226
                        mol_type = protein
                        organism = synthetic construct
SEQUENCE: 26
EVQLVQSGAE VKKPGASVKV SCKASGFNIK DTYIHWVRQA PGQGLEWIGR IDPANDNTLY  60
ASKFQGRATI TADTSTSTAY LELSSLRSED TAVYYCGRGY GYYVFDHWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHT                 226

SEQ ID NO: 27           moltype = AA  length = 214
FEATURE                 Location/Qualifiers
REGION                  1..214
                        note = Synthetic Construct
source                  1..214
                        mol_type = protein
                        organism = synthetic construct
SEQUENCE: 27
DVQITQSPSS LSASVGDRVT ITCRTSRSIS KYLAWYQEKP GKTNKLLIYS GSTLQSGIPS  60
RFSGSGSGTD FTLTISSLQP EDFATYYCQQ VNEFPVTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 28           moltype = AA  length = 448
FEATURE                 Location/Qualifiers
REGION                  1..448
                        note = Synthetic Construct
source                  1..448
                        mol_type = protein
                        organism = synthetic construct
SEQUENCE: 28
EVQLVQSGAE VKKPGASVKV SCKASGFNIK DTYIHWVRQA PGQGLEWIGR IDPANDNTLY  60
ASKFQGRATI TADTSTSTAY LELSSLRSED TAVYYCGRGY GYYVFDHWGQ GTLVTVSSAS  120
```

```
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALG APIEKTISKA KGQPREPQVY TLPPSREEMT  360
KNQVSLSCAV KGFYPSDIAV EWESNGQPEN NYKTTPPVLD SDGSFFLVSK LTVDKSRWQQ  420
GNVFSCSVMH EALHNHYTQK SLSLSPGK                                    448

SEQ ID NO: 29          moltype = AA  length = 214
FEATURE                Location/Qualifiers
REGION                 1..214
                       note = Synthetic Construct
source                 1..214
                       mol_type = protein
                       organism = synthetic construct
SEQUENCE: 29
DVQITQSPSS LSASVGDRVT ITCRTSRSIS QYLAWYQEKP GKTNKLLIYS GSTLQSGIPS  60
RFSGSGSGTD FTLTISSLQP EDFATYYCQQ VNEFPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 30          moltype = AA  length = 227
FEATURE                Location/Qualifiers
REGION                 1..227
                       note = Synthetic Construct
source                 1..227
                       mol_type = protein
                       organism = synthetic construct
SEQUENCE: 30
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALGA PIEKTISKAK  120
GQPREPQVYT LPPSREEMTK NQVSLWCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 31          moltype = AA  length = 276
FEATURE                Location/Qualifiers
source                 1..276
                       mol_type = protein
                       organism = Macaca mulatta
SEQUENCE: 31
MRNQAPGRPK GATSPPPLPT GSRAPPVAPE LRAEPRPGER VMAPPVTALL LPLVLLLHAA  60
RPNQFRVSPL GRTWNLGETV ELKCQVLLSN PTSGCSWLFQ PRGTAARPTF LLYLSQNKPK  120
AAEGLDTQRF SGKRLGDTFV LTLRDFRQEN EGYYFCSALS NSIMYFSHFV PVFLPAKPTT  180
TPAPRSPTPA PTTASQPLSL RPEACRPAAG GSVNTRGLDF ACDIYIWAPL AGACGVLLLS  240
LVITLYCNHR NRRRVCKCPR PVVKSGGKPS LSDRYV                            276

SEQ ID NO: 32          moltype = AA  length = 276
FEATURE                Location/Qualifiers
source                 1..276
                       mol_type = protein
                       organism = Macaca fascicularis
SEQUENCE: 32
MRNQAPGRPK GATSPPPLPT GSRAPPVAPE LRAEPRPGER VMAPPVTALL LPLVLLLHAA  60
RPNQFRVSPL GRTWNLGETV ELKCQVLLSN PTSGCSWLFQ PRGTAARPTF LLYLSQNKPK  120
AAEGLDTQRF SGKRLGDTFV LTLRDFRQEN EGYYFCSALS NSIMYFSHFV PVFLPAKPTT  180
TPAPRPPTPA PTTASQPLSL RPEACRPAAG GSVNTRGLDF ACDIYIWAPL AGACGVLLLS  240
LVITLYCNHR NRRRVCKCPR PVVKSGGKPS LSDRYV                            276

SEQ ID NO: 33          moltype = AA  length = 234
FEATURE                Location/Qualifiers
source                 1..234
                       mol_type = protein
                       organism = Homo sapiens
SEQUENCE: 33
MALPVTALLL PLALLLHAAR PSQFRVSPLD RTWNLGETVE LKCQVLLSNP TSGCSWLFQP  60
RGAAASPTFL LYLSQNKPKA AEGLDTQRFS GKRLGDTFVL TLSDFRRENE GYYFCSALSN  120
SIMYFSHFVP VFLPAKPTTT PAPRPPTPAP TIASQPLSLR PEACRPAAGG AVHTRGLDFA  180
CDIYIWAPLA GTCGVLLLSL VITLYCNHRN RRRVCKCPRP VVKSGDKPSL SARY        234
```